US008481504B2

(12) United States Patent
Rabinovsky et al.

(10) Patent No.: US 8,481,504 B2
(45) Date of Patent: Jul. 9, 2013

(54) INSULIN-LIKE GROWTH FACTOR (IGF-I) PLASMID-MEDIATED SUPPLEMENTATION FOR THERAPEUTIC APPLICATIONS

(75) Inventors: Eric D. Rabinovsky, Houston, TX (US); Ruxandra Draghia-Akli, Houston, TX (US)

(73) Assignee: VGX Pharmaceuticals, Inc., Blue Bell, PA (US)

( * ) Notice: Subject to any disclaimer, the term of this patent is extended or adjusted under 35 U.S.C. 154(b) by 0 days.

(21) Appl. No.: 10/798,896

(22) Filed: Mar. 11, 2004

(65) Prior Publication Data

US 2005/0238624 A1 Oct. 27, 2005

Related U.S. Application Data

(60) Provisional application No. 60/454,079, filed on Mar. 12, 2003.

(51) Int. Cl.
*A61K 48/00* (2006.01)
*A01N 63/00* (2006.01)

(52) U.S. Cl.
USPC ...................................... 514/44 R; 424/93.21

(58) Field of Classification Search
USPC ........................................ 424/93.2; 514/44 R
See application file for complete search history.

(56) References Cited

U.S. PATENT DOCUMENTS

| | | | |
|---|---|---|---|
| 4,683,202 A | 7/1987 | Mullis | |
| 4,956,288 A | 9/1990 | Barsoum | |
| 5,298,422 A | 3/1994 | Schwartz | |
| 5,374,544 A | 12/1994 | Schwartz | |
| 5,384,253 A | 1/1995 | Krzyzek | |
| 5,439,440 A | 8/1995 | Hofmann | |
| 5,702,384 A | 12/1997 | Umeyama | |
| 5,704,908 A | 1/1998 | Hofmann | |
| 5,756,264 A | 5/1998 | Schwartz | |
| 5,925,564 A | 7/1999 | Schwartz | |
| 5,925,565 A | 7/1999 | Berlioz | |
| 5,928,906 A | 7/1999 | Koster | |
| 5,935,819 A | 8/1999 | Eichner | |
| 5,955,365 A | 9/1999 | Szoka | |
| 5,994,300 A | 11/1999 | Bayne et al. | |
| 6,121,246 A * | 9/2000 | Isner ............................... | 514/44 |
| 6,150,168 A | 11/2000 | Woo | |
| 6,177,554 B1 | 1/2001 | Woo | |
| 2003/0018984 A1 | 1/2003 | Coleman et al. | |

OTHER PUBLICATIONS

Laron, Journal of Clinical Pathology: Molecular Pathology, 54:311-316, 2001.*
Van Obberghen et al, Eurpopean Journal of Clinical Investigation, 31:966-977, 2001.*
Milner et al, Biochemistry Journal, 308:865-871, 1995.*
van Deutekom et al. Mol. Med. Today, 214-220, May 1998.*
"Myopathy" from Wikipedia, accessed online at www.en.wikipedia.com, on Mar. 10, 2009.*
"Neuromuscular Disease" from Wikipedia, accessed online at www.en.wikipedia.com, on Mar. 10, 2009.*
Gonçalves. Cardiovascular Res., 45: 294-302, 2000.*
Nicosia et al. American J. of Pathology, 145(5): 1023-1029, 1994.*
Aihara, H. and J. Miyazaki. 1998. Gene transfer into muscle by electroporation in vivo. Nat. Biotechnol. 16:867-870.
Akeno, N., J. Robins, M. Zhang, M. F. Czyzyk-Krzeska, and T. L. Clemens. 2002. Induction of vascular endothelial growth factor by IGF-I in osteoblast-like cells is mediated by the PI3K signaling pathway through the hypoxia-inducible factor-2alpha. Endocrinology 143:420-425.
Alila, H., M. Coleman, H. Nitta, M. French, K. Anwer, Q. Liu, T. Meyer, J. Wang, R. Mumper, D. Oubari, S. Long, J. Nordstrom, and A. Rolland. 1997. Expression of biologically active human insulin-like growth factor-I following intramuscular injection of a formulated plasmid in rats. Hum. Gene Ther. 8:1785-1795.
Almendro, N., T. Bellon, C. Rius, P. Lastres, C. Langa, A. Corbi, and C. Bernabeu. 1996. Cloning of the human platelet endothelial cell adhesion molecule-1 promoter and its tissue-specific expression. Structural and functional characterization. J. Immunol. 157:5411-5421.
Andres, V. and K. Walsh. 1996. Myogenin expression, cell cycle withdrawal, and phenotypic differentiation are temporally separable events that precede cell fusion upon myogenesis. J Cell Biol. 132:657-666.
Aratani, Y., R. Okazaki, and H. Koyama. 1992. End extension repair of introduced targeting vectors mediated by homologous recombination in mammalian cells. Nucleic Acids Res. 20:4795-4801.
Arthur, W. T., R. B. Vernon, E. H. Sage, and M. J. Reed. 1998. Growth factors reverse the impaired sprouting of microvessels from aged mice. Microvasc. Res. 55:260-270.
Bagust, A., P. K. Hopkinson, L. Maslove, and C. J. Currie. 2002. The projected health care burden of Type 2 diabetes in the UK from 2000 to 2060. Diabet. Med. 19 Suppl 4:1-5.:1-5.
Barton-Davis, E. R., D. I. Shoturma, A. Musaro, N. Rosenthal, and H. L Sweeney. 1998. Viral mediated expression of insulin-like growth factor I blocks the aging-related loss of skeletal muscle function [In Process Citation]. Proc. Natl. Acad. Sci. U. S. A. 95:15603-15607.
Beckman, J.A., Creager, M.A., Libby, P., 2002. Diabetes and atherosclerosis: epidemiology, pathophysiology, and management. JAMA 287, 2570-2581.

(Continued)

Primary Examiner — Thaian N Ton
(74) Attorney, Agent, or Firm — Thomas Kim

(57) ABSTRACT

Composition and method for stimulating angiogenesis, stimulating myogenesis, upregulating angiogenic factors and angiopoietins, and treating the muscular and vascular complications of diabetes. Overall, the embodiments of the invention can be accomplished by delivering a heterologous nucleic acid sequence encoding insulin-like growth factor I ("IGF-I") or a functional biological equivalent thereof into the cells of the subject and allowing expression of the encoded gene to occur while the modified cells are within the subject. The nucleic acid sequence maybe delivered by a vector system including a synthetic myogenic promoter and a 3' untranslated region. The preferred method to deliver the constitutive or inducible nucleic acid encoding sequences of IGF-I or the functional biological equivalents thereof is directly into the cells of the subject by the process of in vivo electroporation.

12 Claims, 13 Drawing Sheets

OTHER PUBLICATIONS

Bermont, L., F. Lamielle, S. Fauconnet, H. Esumi, A. Weisz, and G. L. Adessi. 2000. Regulation of vascular endothelial growth factor expression by insulin-like growth factor-I in endometrial adenocarcinoma cells. Int. J Cancer 85:117-123.

Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.

Boshart, M., F. Weber, G. Jahn, K. Dorsch-Hasler, B. Fleckenstein, and W. Schaffner. 1985. A very strong enhancer is located upstream of an immediate early gene of human cytomegalovirus. Cell 41:521-530.

Buerke, M., T. Murohara, C. Skurk, C. Nuss, K. Tomaselli, and A. M. Lefer. 1995. Cardioprotective effect of insulin-like growth factor I in myocardial ischemia followed by reperfusion. Proc. Natl. Acad. Sci. U. S. A 92:8031-8035.

Carbonelli, D. L., E. Corley, M. Seigelchifer, and J. Zorzopulos. 1999. A plasmid vector for isolation of strong promoters in *Escherichia coli*. FEMS Microbiol. Lett. 177:75-82.

Caroni, P., C. Schneider, M. C. Kiefer, and J. Zapf. 1994. Role of muscle insulin-like growth factors in nerve sprouting: suppression of terminal sprouting in paralyzed muscle by IGF-binding protein 4. J. Cell Biol. 125:893-902.

Castellon, R., H. K. Hamdi, I. Sacerio, A. M. Aoki, M. C. Kenney, and A. V. Ljubimov. 2002. Effects of angiogenic growth factor combinations on retinal endothelial cells. Exp. Eye Res. 74:523-535.

Chandler, S. D., A. Mayeda, J. M. Yeakley, A. R. Krainer, and X. D. Fu. 1997. RNA splicing specificity determined by the coordinated action of RNA recognition motifs in SR proteins. Proc. Natl. Acad. Sci. U. S. A 94:3596-3601.

Cheng, H. L., A. Randolph, D. Yee, P. Delafontaine, G. Tennekoon, and E. L. Feldman. 1996. Characterization of insulin-like growth factor-I and its receptor and binding proteins in transected nerves and cultured Schwann cells. J. Neurochem. 66:525-536.

Cocea, L. 1997. Duplication of a region in the multiple cloning site of a plasmid vector to enhance cloning-mediated addition of restriction sites to a DNA fragment. Biotechniques 23:814-816.

Coleman, M. E., F. DeMayo, K. C. Yin, H. M. Lee, R. Geske, C. Montgomery, and R. J. Schwartz. 1995. Myogenic vector expression of insulin-like growth factor I stimulates muscle cell differentiation and myofiber hypertrophy in transgenic mice. J. Biol. Chem. 270:12109-12116.

Criqui,M.H., 2001. Peripheral arterial disease—epidemiological aspects. Vasc. Med. 6, 3-7.

Currie, C. J., C. L Morgan, and J. R. Peters. 1998. The epidemiology and cost of inpatient care for peripheral vascular disease, infection, neuropathy, and ulceration in diabetes. Diabetes Care 21:42-48.

Dai, B., H. Wu, E. Holthuizen, and P. Singh. 2001. Identification of a novel cis element required for cell density-dependent down-regulation of insulin-like growth factor-2 P3 promoter activity in Caco2 cells. J. Biol. Chem. 276:6937-6944.

Danko, I. and J. A. Wolff. 1994. Direct gene transfer into muscle. [Review]. Vaccine 12:1499-1502.

Darquet, A. M., B. Cameron, P. Wils, D. Scherman, and J. Crouzet. 1997. A new DNA vehicle for nonviral gene delivery: supercoiled minicircle. Gene Ther. 4:1341-1349.

Darquet, A. M., R. Rangara, P. Kreiss, B. Schwartz, S. Naimi, P. Delaere, J. Crouzet, and D. Scherman. 1999. Minicircle: an improved DNA molecule for in vitro and in vivo gene transfer. Gene Ther. 6:209-219.

Davis, H. L., R. G. Whalen, and B. A. Demeneix. 1993. Direct gene transfer into skeletal muscle in vivo: factors affecting efficiency of transfer and stability of expression. Human Gene Therapy 4:151-159.

Davis, S., N. Papadopoulos, T. H. Aldrich, P. C. Maisonpierre, T. Huang, L. Kovac, A. Xu, R. Leidich, E. Radziejewska, A. Rafique, J. Goldberg, V. Jain, K. Bailey, M. Karow, J. Fandl, S. J. Samuelsson, E. Ioffe, J. S. Rudge, T. J. Daly, C. Radziejewski, and G. D. Yancopoulos. 2003. Angiopoietins have distinct modular domains essential for receptor binding, dimerization and superclustering. Nat. Struct. Biol. 10:38-44.

De Luca, A., S. Pierno, C. Camerino, D. Cocchi, and D. C. Camerino. 1999. Higher content of insulin-like growth factor-I in dystrophic mdx mouse: potential role in the spontaneous regeneration through an electrophysiological investigation of muscle function. Neuromuscul. Disord. 9:11-18.

Dolnik, V., M. Novotny, and J. Chmelik. 1993. Electromigration behavior of poly-(L-glutamate) conformers in concentrated polyacrylamide gels. Biopolymers 33:1299-1306.

Donath, M. Y., M. A. Gosteli-Peter, C. Hauri, E. R. Froesch, and J. Zapf. 1997. Insulin-like growth factor-I stimulates myofibrillar genes and modulates atrial natriuretic factor mRNA in rat heart. Eur. J. Endocrinol. 137:309-315.

Donath, M. Y., G. Sutsch, X. W. Yan, B. Piva, H. P. Brunner, Y. Glatz, J. Zapf, F. Follath, E. R. Froesch, and W. Kiowski. 1998. Acute cardiovascular effects of insulin-like growth factor I in patients with chronic heart failure. J. Clin. Endocrinol. Metab 83:3177-3183.

Donath, M. Y., J. Zapf, M. Eppenberger-Eberhardt, E. R. Froesch, and H. M. Eppenberger. 1994. Insulin-like growth factor I stimulates myofibril development and decreases smooth muscle alpha-actin of adult cardiomyocytes. Proc. Natl. Acad. Sci. U. S. A 91:1686-1690.

Dorsch-Hasler, K., G. M. Keil, F. Weber, M. Jasin, W. Schaffner, and U. H. Koszinowski. 1985. A long and complex enhancer activates transcription of the gene coding for the highly abundant immediate early mRNA in murine cytomegalovirus. Proc. Natl. Acad. Sci. U. S. A 82:8325-8329.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., A. S. Khan, K. K. Cummings, D. Parghi, R. H. Carpenter, and P. A. Brown. 2002a. Electrical Enhancement of Formulated Plasmid Delivery in Animals. Technology in Cancer Research & Treatment 1:365-371.

Draghia-Akli, R., P. B. Malone, L. A. Hill, K. M. Ellis, R. J. Schwartz, and J. L. Nordstrom. 2002. Enhanced animal growth via ligand-regulated GHRH myogenic-injectable vectors. FASEB J. 16:426-428.

Feener, E. P. and G. L. King. 1997. Vascular dysfunction in diabetes mellitus. Lancet 350 Suppl 1 :S19-13.:S19-13.

Fewell, J. G., F. MacLaughlin, V. Mehta, M. Gondo, F. Nicol, E. Wilson, and L. C. Smith. 2001. Gene therapy for the treatment of hemophilia B using PINC-formulated plasmid delivered to muscle with electroporation. Mol. Ther. 3:574-583.

Fiorelli, G., L. Formigli, O. S. Zecchi, F. Gori, A. Falchetti, A. Morelli, A. Tanini, S. Benvenuti, and M. L. Brandi. 1996. Characterization and function of the receptor for IGF-I in human preosteoclastic cells. Bone 18:269-276.

Fiorelli, G., C. Orlando, S. Benvenuti, F. Franceschelli, S. Bianchi, P. Pioli, A. Tanini, M. Serio, F. Bartucci, and M. L. Brandi. 1994. Characterization, regulation, and function of specific cell membrane receptors for insulin-like growth factor I on bone endothelial cells. J Bone Miner. Res. 9:329-337.

Flamme, I., G. Breier, and W. Risau. 1995. Vascular endothelial growth factor (VEGF) and VEGF receptor 2 (flk-1) are expressed during vasculogenesis and vascular differentiation in the quail embryo. Dev. Biol. 169:699-712.

Florini, J. R., D. Z. Ewton, K. A. Magri, and F. J. Mangiacapra. 1993. IGFs and muscle differentiation. Adv. Exp. Med. Biol. 343:319-26:319-326.

Florini, J. R., K. A. Magri, D. Z. Ewton, P. L. James, K. Grindstaff, and P. S. Rotwein. 1991. "Spontaneous" differentiation of skeletal myoblasts is dependent upon autocrine secretion of insulin-like growth factor-II. J. Biol. Chem. 266:15917-15923.

Folkman, J. and M. Klagsbrun. 1987. Angiogenic factors. Science 235:442-447.

Fowler, B., Jamrozik, K., Norman, P., Allen, Y., 2002. Prevalence of peripheral arterial disease: persistence of excess risk in former smokers. Aust. N. Z. J Public Health 26, 219-224.

Fryer, A. D. and D. B. Jacoby. 1993. Effect of inflammatory cell mediators on M2 muscarinic receptors in the lungs. Life Sci. 52:529-536.

Gehl, J., T. Skovsgaard, and L. M. Mir. 1998. Enhancement of cytotoxicity by electropermeabilization: an improved method for screening drugs. Anticancer Drugs 9:319-325.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

German, M., S. Ashcroft, K. Docherty, H. Edlund, T. Edlund, S. Goodison, H. Imura, G. Kennedy, O. Madsen, D. Melloul, and . 1995. The insulin gene promoter. A simplified nomenclature. Diabetes 44:1002-1004.

Glazner, G. W., A. E. Morrison, and D. N. Ishii. 1994. Elevated insulin-like growth factor (IGF) gene expression in sciatic nerves during IGF-supported nerve regeneration. Brain Res. Mol. Brain Res. 25:265-272.

Goad, D. L., J. Rubin, H. Wang, A. H. Tashjian, Jr., and C. Patterson. 1996. Enhanced expression of vascular endothelial growth factor in human SaOS-2 osteoblast-like cells and murine osteoblasts induced by insulin-like growth factor I. Endocrinology 137:2262-2268.

Goldspink, G. 1999. Changes in muscle mass and phenotype and the expression of autocrine and systemic growth factors by muscle in response to stretch and overload. J. Anat. 194:323-334.

Heller, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Herzog, R. W., J. D. Mount, V. R. Arruda, K. A. High, and C. D. Lothrop, Jr. 2001. Muscle-directed gene transfer and transient immune suppression result in sustained partial correction of canine hemophilia B caused by a null mutation. Mol. Ther. 4:192-200.

Horlick, R. A. and P. A. Benfield. 1989. The upstream muscle-specific enhancer of the rat muscle creatine kinase gene is composed of multiple elements. Mol. Cell Biol. 9:2396-2413.

Horvath, K. A., J. Doukas, C. Y. Lu, N. Belkind, R. Greene, G. F. Pierce, and D. A. Fullerton. 2002. Myocardial functional recovery after fibroblast growth factor 2 gene therapy as assessed by echocardiography and magnetic resonance imaging. Ann. Thorac. Surg. 74:481-486.

Hsu, H. H., M. M. Zdanowicz, V. R. Agarwal, and P. W. Speiser. 1997. Expression of myogenic regulatory factors in normal and dystrophic mice: effects of IGF-1 treatment. Biochem. Mol. Med. 60:142-148.

Inouye, C., P. Remondelli, M. Karin, and S. Elledge. 1994. Isolation of a cDNA encoding a metal response element binding protein using a novel expression cloning procedure: the one hybrid system. DNA Cell Biol. 13:731-742.

Inouye, S., A. Nakazawa, and T. Nakazawa. 1985. Determination of the transcription initiation site and identification of the protein product of the regulatory gene xylR for xyl operons on the TOL plasmid. J. Bacteriol. 163:863-869.

Ito, H., M. Hiroe, Y. Hirata, M. Tsujino, S. Adachi, M. Shichiri, A. Koike, A. Nogami, and F. Marumo. 1993. Insulin-like growth factor-I induces hypertrophy with enhanced expression of muscle specific genes in cultured rat cardiomyocytes. Circulation 87:1715-1721.

Jabri, N., D. S. Schalch, S. L. Schwartz, J. S. Fischer, M. S. Kipnes, B. J. Radnik, N. J. Turman, V. S. Marcsisin, and H. P. Guler. 1994. Adverse effects of recombinant human insulin-like growth factor I in obese insulin-resistant type II diabetic patients. Diabetes 43:369-374.

Jaynes, J. B., J. E. Johnson, J. N. Buskin, C. L Gartside, and S. D. Hauschka. 1988. The muscle creatine kinase gene is regulated by multiple upstream elements, including a muscle-specific enhancer. Mol. Cell Biol. 8:62-70.

Jeschke, M. G., R. E. Barrow, H. K. Hawkins, K. Yang, R. L. Hayes, B. J. Lichtenbelt, J. R. Perez-Polo, and D. N. Herndon. 1999. IGF-I gene transfer in thermally injured rats. Gene Ther. 6:1015-1020.

Kardami, E. 1990. Stimulation and inhibition of cardiac myocyte proliferation in vitro. Mol. Cell Biochem. 92:129-135.

Kasemkijwattana, C., J. Menetrey, G. Somogyl, M. S. Moreland, F. H. Fu, B. Buranapanitkit, S. C. Watkins, and J. Huard. 1998. Development of approaches to improve the healing following muscle contusion. Cell Transplant. 7:585-598.

Kawamoto, T., K. Makino, H. Niwa, H. Sugiyama, S. Kimura, M. Amemura, A. Nakata, and T. Kakunaga. 1988. Identification of the human beta-actin enhancer and its binding factor. Mol. Cell Biol. 8:267-272.

Kawamoto, T., K. Makino, S. Orita, A. Nakata, and T. Kakunaga. 1989. DNA bending and binding factors of the human beta-actin promoter. Nucleic Acids Res. 17:523-537.

Klamut, H. J., L. O. Bosnoyan-Collins, R. G. Worton, P. N. Ray, and H. L Davis. 1996. Identification of a transcriptional enhancer within muscle intron 1 of the human dystrophin gene. Hum. Mol. Genet. 5:1599-1606.

Klamut, H. J., S. B. Gangopadhyay, R. G. Worton, and P. N. Ray. 1990. Molecular and functional analysis of the muscle-specific promoter region of the Duchenne muscular dystrophy gene. Mol. Cell Biol. 10:193-205.

Kraus, J., M. Woltje, N. Schonwetter, and V. Hollt. 1998. Alternative promoter usage and tissue specific expression of the mouse somatostatin receptor 2 gene. FEBS Lett. 428:165-170.

Lareyre, J. J., T. Z. Thomas, W. L. Zheng, S. Kasper, D. E. Ong, M. C. Orgebin-Crist, and R. J. Matusik. 1999. A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274:8282-8290.

Larsen, P. R., J. W. Harney, and D. D. Moore. 1986. Sequences required for cell-type specific thyroid hormone regulation of rat growth hormone promoter activity. J. Biol. Chem. 261:14373-14376.

Lee, S. H., W. Wang, S. Yajima, P. A. Jose, and M. M. Mouradian. 1997. Tissue-specific promoter usage in The D1A dopamine receptor gene in brain and kidney. DNA Cell Biol. 16:1267-1275.

Lesbordes, J. C., T. Bordet, G. Haase, L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11:1615-1625.

Lescaudron, L., E. Peltekian, J. Fontaine-Perus, D. Paulin, M. Zampieri, L. Garcia, and E. Parrish. 1999. Blood borne macrophages are essential for the triggering of muscle regeneration following muscle transplant. Neuromuscul. Disord. 9:72-80.

Leung, D. W., G. Cachianes, W. J. Kuang, D. V. Goeddel, and N. Ferrara. 1989. Vascular endothelial growth factor is a secreted angiogenic mitogen. Science 246:1306-1309.

Levenson, V. V., E. D. Transue, and I. B. Roninson. 1998. Internal ribosomal entry site-containing retroviral vectors with green fluorescent protein and drug resistance markers. Hum. Gene Ther. 9:1233-1236.

Li, C., S. Ke, Q. P. Wu, W. Tansey, N. Hunter, L. M. Buchmiller, L. Mites, C. Chamsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Lin, H., K. E. Yutzey, and S. F. Konieczny. 1991. Muscle-specific expression of the troponin I gene requires interactions between helix-loop-helix muscle regulatory factors and ubiquitous transcription factors. Mol. Cell Biol. 11:267-280.

Liu, Y., H. Li, K. Tanaka, N. Tsumaki, and Y. Yamada. 2000. Identification of an enhancer sequence within the first intron required for cartilage-specific transcription of the alpha2(XI) collagen gene. J. Biol. Chem. 275:12712-12718.

Lombardi, G., A. Colao, A. Cuocolo, S. Longobardi, C. Di Somma, F. Orio, B. Merola, E. Nicolai, and M. Salvatore. 1997. Cardiological aspects of growth hormone and insulin-like growth factor-I. J. Pediatr. Endocrinol. Metab 10:553-560.

Lucas, M. L., L. Heller, D. Coppola, and R. Heller. 2002. IL-12 plasmid delivery by in vivo electroporation for the successful treatment of established subcutaneous B16.F10 melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Maccoll, G. S., G. Goldspink, and P. M. Bouloux. 1999. Using skeletal muscle as an artificial endocrine tissue. J. Endocrinol. 162:1-9.

Macejak, D. G. and P. Sarnow. 1991. Internal initiation of translation mediated by the 5' leader of a cellular mRNA. Nature 353:90-94.

Matsubara, H., Y. Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

Matsuo, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

McNally, M. A., J. S. Lebkowski, T. B. Okarma, and L. B. Lerch. 1988. Optimizing electroporation parameters for a variety of human hematopoietic cell lines. Biotechniques 6:882-886.

Meigs, J. B., M. G. Larson, R. B. D'Agostino, D. Levy, M. E. Clouse, D. M. Nathan, P. W. Wilson, and C. J. O'Donnell. 2002. Coronary artery calcification in type 2 diabetes and insulin resistance: the framingham offspring study. Diabetes Care 25:1313-1319.

Meigs, J. B., D. E. Singer, L. M. Sullivan, K. A. Dukes, R. B. D'Agostino, D. M. Nathan, E. H. Wagner, S. H. Kaplan, and S. Greenfield. 1997. Metabolic control and prevalent cardiovascular disease in non-insulin-dependent diabetes mellitus (NIDDM): The NIDDM Patient Outcome Research Team. Am. J Med. 102:38-47.

Menetrey, J., C. Kasemkijwattana, C. S. Day, P. Bosch, M. Vogt, F. H. Fu, M. S. Moreland, and J. Huard. 2000. Growth factors improve muscle healing in vivo. J. Bone Joint Surg. Br. 82:131-137.

Miele, C., J. J. Rochford, N. Filippa, S. Giorgetti-Peraldi, and E. Van Obberghen. 2000. Insulin and insulin-like growth factor-I induce vascular endothelial growth factor mRNA expression via different signaling pathways. J Biol. Chem. 275:21695-21702.

Miklavcic, D., K. Beravs, D. Semrov, M. Cemazar, F. Demsar, and G. Sersa. 1998. The importance of electric field distribution for effective in vivo electroporation of tissues. Biophys. J 74:2152-2158.

Montarras, D., J. Chelly, E. Bober, H. Arnold, M. O. Ott, F. Gros, and C. Pinset. 1991. Developmental patterns in the expression of Myf5, MyoD, myogenin, and MRF4 during myogenesis. New Biol. 3:592-600.

Mumper, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., S. Arakawa, K. Fukazawa, Y. Fujiwara, T. Yoshida, R. Sasaki, S. Masuda, and H. M. Park. 2001. In vivo gene electroporation in skeletal muscle with special reference to the duration of gene expression. Int. J Mol. Med. 7:37-42.

Nairn, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Narum, D. L., S. Kumar, W. O. Rogers, S. R. Fuhrmann, H. Liang, M. Oakley, A. Taye, B. K. Sim, and S. L. Hoffman. 2001. Codon optimization of gene fragments encoding *Plasmodium falciparum* merzoite proteins enhances DNA vaccine protein expression and immunogenicity in mice. Infect. Immun. 69:7250-7253.

Neumann, E., M. Schaefer-Ridder, Y. Wang, and P. H. Hofschneider. 1982. Gene transfer into mouse lyoma cells by electroporation in high electric fields. EMBO J. 1:841-845.

Nomoto, S., Y. Tatematsu, T. Takahashi, and H. Osada. 1999. Cloning and characterization of the alternative promoter regions of the human LIMK2 gene responsible for alternative transcripts with tissue-specific expression. Gene 236:259-271.

Ohlsson, H., S. Thor, and T. Edlund. 1991. Novel insulin promoter- and enhancer-binding proteins that discriminate between pancreatic alpha- and beta-cells. Mol. Endocrinol. 5:897-904.

Otanim Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Pech, M., C. D. Rao, K. C. Robbins, and S. A. Aaronson. 1989. Functional identification of regulatory elements within the promoter region of platelet-derived growth factor 2. Mol. Cell Biol. 9:396-405.

Pelletier, J. and N. Sonenberg. 1988. Internal initiation of translation of eukaryotic mRNA directed by a sequence derived from poliovirus RNA. Nature 334:320-325.

Peters, K. G. 1998. Vascular endothelial growth factor and the angiopoietins: working together to build a better blood vessel. Circ. Res. 83:342-343.

Pinkert, C. A., D. M. Ornitz, R. L. Brinster, and R. D. Palmiter. 1987. An albumin enhancer located 10 kb upstream functions along with its promoter to direct efficient, liver-specific expression in transgenic mice. Genes Dev. 1:268-276.

Potter, H., L. Weir, and P. Leder. 1984. Enhancer-dependent expression of human kappa immunoglobulin genes introduced into mouse pre-B lymphocytes by electroporation. Proc. Natl. Acad. Sci. U. S. A 81:7161-7165.

Prentice, H., R. A. Kloner, T. Prigozy, T. Christensen, L. Newman, Y. Li, and L. Kedes. 1994. Tissue restricted gene expression assayed by direct DNA injection into cardiac and skeletal muscle. Journal of Molecular & Cellular Cardiology 26:1393-1401.

Punglia, R. S., M. Lu, J. Hsu, M. Kuroki, M. J. Tolentino, K. Keough, A. P. Levy, N. S. Levy, M. A. Goldberg, R. J. D'Amato, and A. P. Adamis. 1997. Regulation of vascular endothelial growth factor expression by insulin-like growth factor I. Diabetes 46:1619-1626.

Rabinovsky, E D., E. Gelir, S. Gelir, H. Lui, M. Kattash, F. J. DeMayo, S. M. Shenaq, and R. J. Schwartz. 2003. Targeted expression of IGF-I transgene to skeletal muscle accelerates muscle and motor neuron regeneration. FASEB J 17:53-55.

Rantanen, J., T. Hurme, R. Lukka, J. Heino, and H. Kalimo. 1995. Satellite cell proliferation and the expression of myogenin and desmin in regenerating skeletal muscle: evidence for two different populations of satellite cells. Lab Invest 72:341-347.

Reinmuth, N., F. Fan, W. Liu, A. A. Parikh, O. Stoeltzing, Y. D. Jung, C. D. Bucana, R. Radinsky, G. E. Gallick, and L. M. Ellis. 2002. Impact of insulin-like growth receptor-I function on angiogenesis, growth, and metastasis of colon cancer. Lab Invest 82:1377-1389.

Reiss, K., W. Cheng, A. Ferber, J. Kajstura, P. Li, B. Li, G. Olivetti, C. J. Homey, R. Baserga, and P. Anversa. 1996. Overexpression of insulin-like growth factor-1 in the heart is coupled with myocyte proliferation in transgenic mice. Proc. Natl. Acad. Sci. U. S. A 93:8630-8635.

Reiss, K., J. Kajstura, X. Zhang, P. Li, E. Szoke, G. Olivetti, and P. Anversa. 1994. Acute myocardial infarction leads to upregulation of the IGF-1 autocrine system, DNA replication, and nuclear mitotic division in the remaining viable cardiac myocytes. Exp. Cell Res. 213:463-472.

Rivard, A., M. Silver, D. Chen, M. Kearney, M. Magner, B. Annex, K. Peters, and J. M. Isner. 1999. Rescue of diabetes-related impairment of angiogenesis by intramuscular gene therapy with adeno-VEGF. Am. J Pathol. 154:355-363.

Shigematsu, S., K. Yamauchi, K. Nakajima, S. Iijima, T. Aizawa, and K. Hashizume. 1999. IGF-1 regulates migration and angiogenesis of human endothelial cells. Endocr. J 46 Suppl:S59-62.:S59-S62.

Silvestre,J.S., Levy,B.I., 2002. Angiogenesis therapy in ischemic disease. Arch. Mal Coeur Vaiss. 95, 189-196.

Sjogren, K., J. O. Jansson, O. G. Isaksson, and C. Ohlsson. 2002. A transgenic model to determine the physiological role of liver-derived insulin-like growth factor I. Minerva Endocrinol. 27:299-311.

Sjogren, K., J. L. Liu, K. Blad, S. Skrtic, O. Vidal, V. Wallenius, D. LeRoith, J. Tornell, O. G. Isaksson, J. O. Jansson, and C. Ohlsson. 1999. Liver-derived insulin-like growth factor I (IGF-I) is the principal source of IGF-I in blood but is not required for postnatal body growth in mice. Proc. Natl. Acad. Sci. U. S. A 96:7088-7092.

Skroch, P., C. Buchman, and M. Karin. 1993. Regulation of human and yeast metallothionein gene transcription by heavy metal ions. Prog. Clin. Biol. Res. 380:113-28.:113-128.

Smith, L. C. and J. L. Nordstrom. 2000. Advances in plasmid gene delivery and expression in skeletal muscle. Curr. Opin. Mol. Ther. 2:150-154.

Song, S., J. Embury, P. J. Laipis, K. I. Berns, J. M. Crawford, and T. R. Flotte. 2001. Stable therapeutic serum levels of human alpha-1 antitrypsin (AAT) after portal vein injection of recombinant adeno-associated virus (rAAV) vectors. Gene Ther. 8:1299-1306.

Soubrier, F., B. Cameron, B. Manse, S. Somarriba, C. Dubertret, G. Jaslin, G. Jung, C. L. Caer, D. Dang, J. M. Mouvault, D. Scherman, J. F. Mayaux, and J. Crouzet. 1999. pCOR: a new design of plasmid vectors for nonviral gene therapy. Gene Ther. 6:1482-1488.

Spoerri, P. E., E. A. Ellis, R. W. Tarnuzzer, and M. B. Grant. 1998. Insulin-like growth factor: receptor and binding proteins in human retinal endothelial cell cultures of diabetic and non-diabetic origin. Growth Horm. IGF. Res. 8:125-132.

Terada, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J Kidney Dis. 38:S50-S53.

Toneguzzo, F., A. Keating, S. Glynn, and K. McDonald. 1988. Electric field-mediated gene transfer: characterization of DNA transfer and patterns of integration in lymphoid cells. Nucleic Acids Res. 16:5515-5532.

Tripathy, S. K., E. C. Svensson, H. B. Black, E. Goldwasser, M. Margalith, Hobart, PM, and J. M. Leiden. 1996. Long-term expression of erythropoietin in the systemic circulation of mice after intramuscular injection of a plasmid DNA vector. Proc. Natl. Acad. Sci. USA 93:10876-10880.

Tronche, F., A. Rollier, I. Bach, M. C. Weiss, and M. Yaniv. 1989. The rat albumin promoter: cooperation with upstream elements is required when binding of APF/HNFI to the proximal element is partially impaired by mutation or bacterial methylation. Mol. Cell Biol. 9:4759-4766.

Tronche, F., A. Rollier, P. Herbomel, I. Bach, S. Cereghini, M. Weiss, and M. Yaniv. 1990. Anatomy of the rat albumin promoter. Mol. Biol. Med. 7:173-185.

Trudel, M. and F. Costantini. 1987. A 3' enhancer contributes to the stage-specific expression of the human beta-globin gene. Genes Dev. 1:954-961.

Tsumaki, N., T. Kimura, K. Tanaka, J. H. Kimura, T. Ochi, and Y. Yamada. 1998. Modular arrangement of cartilage- and neural tissue-specific cis-elements in the mouse alpha2(XI) collagen promoter. J. Biol. Chem. 273:22861-22864.

Tsurumi, Y., S. Takeshita, D. Chen, M. Kearney, S. T. Rossow, J. Passeri, J. R. Horowitz, J. F. Symes, and J. M. Isner. 1996. Direct intramuscular gene transfer of naked DNA encoding vascular endothelial growth factor augments collateral development and tissue perfusion [see comments]. Circulation 94:3281-3290.

Tur-Kaspa, R., L Teicher, B. J. Levine, A. I. Skoultchi, and D. A. Shafritz. 1986. Use of electroporation to introduce biologically active foreign genes into primary rat hepatocytes. Mol. Cell Biol. 6:716-718.

Vance, M. L. 1990. Growth-hormone-releasing hormone. [Review] [52 refs]. Clinical Chemistry 36:415-420.

Vandenburgh, H. H., P. Karlisch, J. Shansky, and R. Feldstein. 1991. Insulin and IGF-I induce pronounced hypertrophy of skeletal myofibers in tissue culture. Am. J. Physiol. 260:C475-C484.

Veikkola, T., M. Karkkainen, L. Claesson-Welsh, and K. Alitalo. 2000. Regulation of angiogenesis via vascular endothelial growth factor receptors. Cancer Res. 60:203-212.

Vilquin, J. T., P. F. Kennel, M. Patumeau-Jouas, P. Chapdelaine, N. Boissel, P. Delaere, J. P. Tremblay, D. Scherman, M. Y. Fiszman, and K. Schwartz. 2001. Electrotransfer of naked DNA in the skeletal muscles of animal models of muscular dystrophies. Gene Ther. 8:1097-1107.

Walsh, M. F., M. Barazi, G. Pete, R. Muniyappa, J. C. Dunbar, and J. R. Sowers. 1996. Insulin-like growth factor I diminishes in vivo and in vitro vascular contractility: role of vascular nitric oxide. Endocrinology 137:1798-1803.

Wang, L., W. Ma, R. Markovich, J. W. Chen, and P. H. Wang. 1998a. Regulation of cardiomyocyte apoptotic signaling by insulin-like growth factor I. Circ. Res. 83:516-522.

Wang, L, W. Ma, R. Markovich, W. L. Lee, and P. H. Wang. 1998b. Insulin-like growth factor I modulates induction of apoptotic signaling in H9C2 cardiac muscle cells. Endocrinology 139:1354-1360.

Wells, K. E., J. Maule, R. Kingston, K. Foster, J. McMahon, E. Damien, A. Poole, and D. J. Wells. 1997. Immune responses, not promoter inactivation, are responsible for decreased long-term expression following plasmid gene transfer into skeletal muscle. FEBS Lett. 407:164-168.

Wolff, J. A., R. W. Malone, P. Williams, W. Chong, G. Acsadi, A. Jani, Felgner, and PL. 1990. Direct gene transfer into mouse muscle in vivo. Science 247:1465-1468.

Wu, H. K., J. A. Squire, Q. Song, and R. Weksberg. 1997. Promoter-dependent tissue-specific expressive nature of imprinting gene, insulin-like growth factor II, in human tissues. Biochem. Biophys. Res. Commun. 233:221-226.

Wu, Y., S. Yakar, L. Zhao, L. Hennighausen, and D. LeRoith. 2002. Circulating insulin-like growth factor-I levels regulate colon cancer growth and metastasis. Cancer Res. 62:1030-1035.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

Yasui, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J. Mol. Med. 8:489-494.

Yin, D. and J. G. Tang. 2001. Gene therapy for streptozotocin-induced diabetic mice by electroporational transfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

Yutzey, K. E. and S. F. Konieczny. 1992. Different E-box regulatory sequences are functionally distinct when placed within the context of the troponin 1 enhancer. Nucleic Acids Res. 20:5105-5113.

Zhao-Emonet, J. C., O. Boyer, J. L Cohen, and D. Klatzmann. 1998. Deletional and mutational analyses of the human CD4 gene promoter: characterization of a minimal tissue-specific promoter. Biochem Biophys. Acta 1442:109-119.

Zhuang, H. X., C. K. Snyder, S. F. Pu, and D. N. Ishii. 1996. Insulin-like growth factors reverse or arrest diabetic neuropathy: effects on hyperalgesia and impaired nerve regeneration in rats. Exp. Neurol. 140:198-205.

Rabinovsky E. D., Draghia-Akli R., Insulin-Like Growth Factor I Plasmid Therapy Promotes in vivo Angiogenesis. Molecular Therapy vol. 9, No. 1, p. 46-54 (2004).

International Search Report, International Application No. PCT/US 04/007295, Aug. 8, 2004.

European Patent Office, International Search Report and Written Opinion, dated Jan. 12, 2005.

* cited by examiner

Northern blot analysis of IGF-I expression 3 weeks after injection of 5 μg of either SIS II construct or pSP-IGF-I-sk3' construct into tibialis anterior muscle of adult mice

SEQUENCE LISTING

<160> NUMBER OF SEQ ID NOS: 9

<210> SEQ ID NO 1
<211> LENGTH: 5423
<212> TYPE: DNA
<213> ORGANISM: artificial sequence
<220> FEATURE:
<223> OTHER INFORMATION: Nucleic acid sequence for the pAV2001 plasmid.

<400> SEQUENCE: 1

| | | | | | |
|---|---|---|---|---|---|
| ccaccgcggt | ggcggccgtc | cgccctcggc | accatcctca | cgacacccaa | atatggcgac | 60 |
| gggtgaggaa | tggtggggag | ttattttag | agcggtgagg | aaggtgggca | ggcagcaggt | 120 |
| gttggcgctc | taaaaataac | tcccgggagt | tatttttaga | gcggaggaat | ggtgacacc | 180 |
| caaatatggc | gacggttcct | cacccgtcgc | catatttggg | tgtccgccct | cggccggggc | 240 |
| cgcattcctg | ggggccgggc | ggtgctcccg | cccgcctcga | taaaaggctc | cggggccggc | 300 |
| ggcggcccac | gagctacccg | gaggagcggg | aggcgccaag | ctctagaact | agtggatccc | 360 |
| aaggcccaac | tccccgaacc | actcagggtc | ctgtggacag | ctcacctagc | tgccatggga | 420 |
| aaaatcagca | gtcttccaac | ccaattattt | aagtgctgct | tttgtgattt | cttgaaggtg | 480 |
| aagatgcaca | ccatgtcctc | ctcgcatctc | ttctacctgg | cgctgtgcct | gctcaccttc | 540 |
| accagctctg | ccacggctgg | accggagacg | ctctgcgggg | ctgagctggt | ggatgctctt | 600 |
| cagttcgtgt | gtggagacag | gggcttttat | ttcaacaagc | ccacagggta | tggctccagc | 660 |
| agtcggaggg | cgcctcagac | aggtatcgtg | gatgagtgct | gcttccggag | ctgtgatcta | 720 |
| aggaggctgg | agatgtattg | cgcacccctc | aagcctgcca | agtcagctcg | ctctgtccgt | 780 |
| gcccagcgcc | acaccgacat | gcccaagacc | cagaaggaag | tacatttgaa | gaacgcaagt | 840 |
| agagggagtg | caggaaacaa | gaactacagg | atgtaggaag | accctcctga | ggagtgaaga | 900 |
| gtgacatgcc | accgcaggat | cccccgggct | gcaggaattc | gatggcccat | ccattgtcca | 960 |
| ccgtaaatgc | ttctaaacat | gtttacatga | tcactttgcc | aaccacactc | aggatgacaa | 1020 |
| tcttgtaggt | tccaggctgc | tgaggacctc | caccagccat | gcaactttct | attttgtaac | 1080 |
| aatttctggt | tactgttgct | gcaaagctcc | atgtgacaca | gtgtatgtaa | agtgtacata | 1140 |
| aattaattta | ttttacctcg | ttttgtttgt | ttttaaaacc | aatgccctgt | ggaaggaaac | 1200 |
| ataaaacttc | aagaagcatt | aaatcatcag | tcattctgtc | acacccctaa | tgcagttgtt | 1260 |
| tctgtcatca | tttccctggg | ctcttccatc | tctcgctgac | ctgggactgg | gtgctggggc | 1320 |
| tgggagcagg | ggttggggct | ctccagggag | agatggcatg | gggagagtga | tgggatactg | 1380 |
| ctgggggggg | gggactcacc | ctgctgtggg | ctgcaggaag | cccattggtg | cagagagcag | 1440 |
| cctgggatgc | ccatgacacg | gcacccact | gcaccgtgtt | tctcccatgc | ccagtaggga | 1500 |
| aagggttacg | agcgccgttc | attctcagct | tgtgaaggat | tttgttgggc | tcagcctgcc | 1560 |
| agagcagtag | ccaggcatgc | ctgtgcagct | ccgagctgtg | atggacagag | gcaaggctgc | 1620 |
| agctgaggcc | agtggtggg | cacaggttaa | attaagagct | ttccactcca | cttatggaaa | 1680 |
| gccctcctgc | actcaccctg | tccctgggc | tgggggcagc | cagggccact | tcctcacccc | 1740 |
| acctgacaca | caaggctttg | cctgcacagc | caggacctcc | tgtggccaca | gactcttata | 1800 |
| gattcgctgt | gccctaggag | accagggggc | tttccctgcc | tggccttctg | gccccggcga | 1860 |
| cactgcagga | gctgccctat | ctgcctcctc | ttagatggtc | ctgcaggaa | ggctgcactt | 1920 |
| ggcttggggc | tgatccatat | taccactgca | gtagggacag | cactgctgga | agaaaagatg | 1980 |

```
attttcaact gaacttacta tccaggcagg ttattgcttt attgtgatgg tgctaagagt    2040
gcgttctttc tcactgtaat gattttgccc tcatgtgtga atacactttc caataacagc    2100
acagcctcca aagggaattt ctgcaggaag agacagtacc tggtgtggga agtccctgtg    2160
cagccctatg tgcttcaagc tgaatggctg ggactggctg ggagagcagg atcacatcct    2220
ttcttaaaaa gacaaacaga aggtagtgtg tgaccttgct gtatttacta tttacgcgtt    2280
gttgttcagt ggcacatacc tcaacgggga tatggagagc tatttcccca accctcgctg    2340
ctggaccctg atctggggtt ttcctgtagc ttaagcggtg ccaactgctt aagtgattgt    2400
agaatcagta aggctggaaa agaccacaga tcattaagtc caactgtcag ccccatcccc    2460
accgcgccca ctgtcactca gtgccacatc cacgcatttc ttgaacatct ccagggacag    2520
tgactccacc cgtcaccagc tgtgcttcag agcaggcagg gtgacagtct cagtgccagt    2580
tgcatcctgc tgaagagctt aacagtgcag tttaacaacg gactgatttg ttgatgtggt    2640
tgctgaatca gtacgttgag atgtcactaa acttttttgga gattaatttc aggatggaac    2700
acattcttaa ccctgaaacc agcctttgat ttgggcttgg catttgcaga atttgcagga    2760
aaagattgtt tgggaacaga tgaatggaat ttccaccaaa cagaaaatta acacttacac    2820
cagtttgagt ctggtcttcg ttcgatattt cttaagaatc tcatcatcct ccctgctctt    2880
ggaccagtgc tgctgacagg aggtggagga tcatcagggt cagcatcctc agcatctagg    2940
gatgtgcact atgtgtgatg gtgacacttt agagaactgc tttgattccc cagggctttc    3000
cctctcttcc atgcagggct cactatcagc cctgaaagtc caactttctg aacttccagc    3060
accgtctgct cctggtaggc tgttccatag aggccacagg gactgtagcc aggcatgacc    3120
ttttcccagc cgtgctctga atccagcact ggtggctggg aggcagctct ggtcctgggg    3180
tgctgcagtg agccagggaa caagctcagc ttttgttccc tttagtgagg gttaatttcg    3240
agcttggcgt aatcatggtc atagctgttt cctgtgtgaa attgttatcc gctcacaatt    3300
ccacacaaca tacgagccgg aagcataaag tgtaaagcct ggggtgccta atgagtgagc    3360
taactcacat taattgcgtt gcgctcactg cccgctttcc agtcgggaaa cctgtcgtgc    3420
cagctgcatt aatgaatcgg ccaacgcgcg gggagaggcg gtttgcgtat tgggcgctct    3480
tccgcttcct cgctcactga ctcgctgcgc tcggtcgttc ggctgcggcg agcggtatca    3540
gctcactcaa aggcggtaat acggttatcc acagaatcag gggataacgc aggaaagaac    3600
atgtgagcaa aaggccagca aaaggccagg aaccgtaaaa aggccgcgtt gctggcgttt    3660
ttccataggc tccgcccccc tgacgagcat cacaaaaatc gacgctcaag tcagaggtgg    3720
cgaaacccga caggactata agataccagg cgtttccccc tggaagctcc ctcgtgcgc    3780
tctcctgttc cgaccctgcc gcttaccgga tacctgtccg cctttctccc ttcgggaagc    3840
gtggcgcttt ctcatagctc acgctgtagg tatctcagtt cggtgtaggt cgttcgctcc    3900
aagctgggct gtgtgcacga accccccgtt cagcccgacc gctgcgcctt atccggtaac    3960
tatcgtcttg agtccaaccc ggtaagacac gacttatcgc cactggcagc agccactggt    4020
aacaggatta gcagagcgag gtatgtaggc ggtgctacag agttcttgaa gtggtggcct    4080
aactacggct acactagaag aacagtattt ggtatctgcg ctctgctgaa gccagttacc    4140
ttcggaaaaa gagttggtag ctcttgatcc ggcaaacaaa ccaccgctgg tagcggtggt    4200
ttttttgttt gcaagcagca gattacgcgc agaaaaaaag gatctcaaga agatcctttg    4260
atcttttcta cggggtctga cgctcagaag aactcgtcaa gaaggcgata aaggcgatg    4320
cgctgcgaat cgggagcggc gataccgtaa agcacgagga agcggtcagc ccattcgccg    4380
```

```
ccaagctctt cagcaatatc acgggtagcc aacgctatgt cctgatagcg gtccgccaca    4440
cccagccggc cacagtcgat gaatccagaa aagcggccat tttccaccat gatattcggc    4500
aagcaggcat cgccatgggt cacgacgaga tcctcgccgt cgggcatgcg cgccttgagc    4560
ctggcgaaca gttcggctgg cgcgagcccc tgatgctctt cgtccagatc atcctgatcg    4620
acaagaccgg cttccatccg agtacgtgct cgctcgatgc gatgtttcgc ttggtggtcg    4680
aatgggcagg tagccggatc aagcgtatgc agccgccgca ttgcatcagc catgatggat    4740
actttctcgg caggagcaag gtgagatgac aggagatcct gccccggcac ttcgcccaat    4800
agcagccagt cccttcccgc ttcagtgaca acgtcgagca cagctgcgca aggaacgccc    4860
gtcgtggcca gccacgatag ccgcgctgcc tcgtcctgca gttcattcag gcaccggac    4920 aggtcggtct tgacaaaaag aaccgggcgc ccctgcgctg acagccggaa cacggcggca    4980
tcagagcagc cgattgtctg ttgtgcccag tcatagccga atagcctctc cacccaagcg    5040
gccggagaac ctgcgtgcaa tccatcttgt tcaatcatgc gaaacgatcc tcatcctgtc    5100
tcttgatcag atcttgatcc cctgcgccat cagatccttg gcggcaagaa agccatccag    5160
tttactttgc agggcttccc aaccttacca gagggcgccc cagctggcaa ttccggttcg    5220
cttgctgtcc ataaaaccgc ccagtctagc aactgttggg aagggcgatc ggtgcgggcc    5280
tcttcgctat tacgccagct ggcgaaaggg ggatgtgctg caaggcgatt aagttgggta    5340
acgccagggt tttcccagtc acgacgttgt aaaacgacgg ccagtgaatt gtaatacgac    5400
tcactatagg gcgaattgga gct                                            5423

<210> SEQ ID NO 2
<211> LENGTH: 3803
<212> TYPE: DNA
<213> ORGANISM: artificial sequence
<220> FEATURE:
<223> OTHER INFORMATION: Nucleic acid sequence for the pAV2002 plasmid.

<400> SEQUENCE: 2
ccaccgcggt ggcggccgtc cgccctcggc accatcctca cgacacccaa atatggcgac      60
gggtgaggaa tggtggggag ttattttttag agcggtgagg aaggtgggca ggcagcaggt    120
gttggcgctc taaaataac tcccgggagt tattttttaga gcggaggaat ggtggacacc     180
caaatatggc gacggttcct caccgtcgc catatttggg tgtccgccct cggccggggc     240
cgcattcctg ggggccgggc ggtgctcccg cccgcctcga taaaaggctc cggggccggc    300
ggcggcccac gagctacccg gaggagcggg aggcgccaag ctctagaact agtggatccc    360
aaggcccaac tccccgaacc actcagggtc ctgtggacag ctcacctagc tgccatggga    420
aaaatcagca gtcttccaac ccaattattt aagtgctgct tttgtgattt cttgaaggtg    480
aagatgcaca ccatgtcctc ctcgcatctc ttctacctgg cgctgtgcct gctcaccttc    540
accagctctg ccacggctgg accggagacg ctctgcgggg ctgagctggt ggatgctctt    600
cagttcgtgt gtggagacag gggcttttat ttcaacaagc ccacagggta tggctccagc    660
agtcggaggg cgcctcagac aggtatcgtg atgagtgct gcttccggag ctgtgatcta    720
aggaggctgg agatgtattg cgcaccctc aagcctgcca gtcagctcg ctctgtccgt    780 gcccagcgcc acaccgacat gcccaagacc cagaaggaag tacatttgaa gaacgcaagt    840
agagggagtg caggaaacaa gaactacagg atgtaggaag accctcctga ggagtgaaga    900 gtgcatgcc accgcaggat cagccttatc gggtggcatc cctgtgaccc ctccccagtg    960
cctctcctgg ccctggaagt tgccactcca gtgcccacca gccttgtcct aataaaatta   1020
```

```
agttgcatca ttttgtctga ctaggtgtcc ttctataata ttatggggtg gagggggggtg    1080 gtatggagca agggggcaagt tgggaagaca acctgtaggg cctgcggggt ctattgggaa    1140
ccaagctgga gtgcagtggc acaatcttgg ctcactgcaa tctccgcctc ctgggttcaa    1200
gcgattctcc tgcctcagcc tcccgagttg ttgggattcc aggcatgcat gaccaggctc    1260
agctaatttt tgttttttg gtagagacgg ggtttcacca tattggccag gctggtctcc    1320
aactcctaat ctcaggtgat ctacccacct tggcctccca aattgctggg attacaggcg    1380
tgaaccactg ctcccttccc tgtccttctg attttaaaat aactatacca gcaggaggac    1440
gtccagacac agcataggct acctggccat gcccaaccgg tgggacattt gagttgcttg    1500
cttggcactg tcctctcatg cgttgggtcc actcagtaga tgcctgttga attcgatacc    1560
gtcgacctcg agggggggcc cggtaccagc ttttgttccc tttagtgagg gttaatttcg    1620
agcttggcgt aatcatggtc atagctgttt cctgtgtgaa attgttatcc gctcacaatt    1680
ccacacaaca tacgagccgg aagcataaag tgtaaagcct ggggtgccta atgagtgagc    1740
taactcacat taattgcgtt gcgctcactg cccgctttcc agtcgggaaa cctgtcgtgc    1800
cagctgcatt aatgaatcgg ccaacgcgcg gggagaggcg gtttgcgtat tgggcgctct    1860
tccgcttcct cgctcactga ctcgctgcgc tcggtcgttc ggctgcggcg agcggtatca    1920
gctcactcaa aggcggtaat acggttatcc acagaatcag gggataacgc aggaaagaac    1980
atgtgagcaa aaggccagca aaaggccagg aaccgtaaaa aggccgcgtt gctggcgttt    2040
ttccataggc tccgcccccc tgacgagcat cacaaaaatc gacgctcaag tcagaggtgg    2100
cgaaacccga caggactata aagataccag gcgtttcccc ctggaagctc cctcgtgcgc    2160
tctcctgttc cgaccctgcc gcttaccgga tacctgtccg cctttctccc ttcgggaagc    2220
gtggcgcttt ctcatagctc acgctgtagg tatctcagtt cggtgtaggt cgttcgctcc    2280
aagctgggct gtgtgcacga accccccgtt cagcccgacc gctgcgcctt atccggtaac    2340
tatcgtcttg agtccaaccc ggtaagacac gacttatcgc cactggcagc agccactggt    2400
aacaggatta gcagagcgag gtatgtaggc ggtgctacag agttcttgaa gtggtggcct    2460
aactacggct acactagaag aacagtattt ggtatctgcg ctctgctgaa gccagttacc    2520
ttcggaaaaa gagttggtag ctcttgatcc ggcaaacaaa ccaccgctgg tagcggtggt    2580 tttttttgttt gcaagcagca gattacgcgc agaaaaaaag gatctcaaga agatcctttg    2640
atcttttcta cggggtctga cgctcagaag aactcgtcaa gaaggcgata aaggcgatg    2700 cgctgcgaat cgggagcggc gataccgtaa agcacgagga gcggtcagc ccattcgccg    2760 ccaagctctt cagcaatatc acgggtagcc aacgctatgt cctgatagcg gtccgccaca    2820
cccagccggc cacagtcgat gaatccagaa agcggccat tttccaccat gatattcggc    2880
aagcaggcat cgccatgggt cacgacgaga tcctcgccgt cgggcatgcg cgccttgagc    2940
ctggcgaaca gttcggctgg cgcgagcccc tgatgctctt cgtccagatc atcctgatcg    3000
acaagaccgg cttccatccg agtacgtgct cgctcgatgc gatgtttcgc ttggtggtcg    3060
aatgggcagg tagccggatc aagcgtatgc agccgccgca ttgcatcagc catgatggat    3120
actttctcgg caggagcaag gtgagatgac aggagatcct gccccggcac ttcgcccaat    3180
agcagccagt cccttcccgc ttcagtgaca acgtcgagca cagctgcgca aggaacgccc    3240
gtcgtggcca gccacgatag ccgcgctgcc tcgtcctgca gttcattcag ggcaccggac    3300
aggtcggtct tgacaaaaag aaccgggcgc cctgcgctg acagccggaa cacgcggca    3360 tcagagcagc cgattgtctg ttgtgcccag tcatagccga atagcctctc cacccaagcg    3420
```

```
gccggagaac ctgcgtgcaa tccatcttgt tcaatcatgc gaaacgatcc tcatcctgtc    3480
tcttgatcag atcttgatcc cctgcgccat cagatccttg gcggcaagaa agccatccag    3540
tttactttgc agggcttccc aaccttacca gagggcgccc cagctggcaa ttccggttcg    3600
cttgctgtcc ataaaaccgc ccagtctagc aactgttggg aagggcgatc ggtgcgggcc    3660
tcttcgctat tacgccagct ggcgaaaggg ggatgtgctg caaggcgatt aagttgggta    3720
acgccagggt tttcccagtc acgacgttgt aaaacgacgg ccagtgaatt gtaatacgac    3780
tcactatagg gcgaattgga gct                                            3803
```

```
<210> SEQ ID NO 3
<211> LENGTH: 323
<212> TYPE: DNA
<213> ORGANISM: artificial sequence
<220> FEATURE:
<223> OTHER INFORMATION: This is a synthetic promoter SPc5-12

<400> SEQUENCE: 3
cggccgtccg ccctcggcac catcctcacg acacccaaat atggcgacgg gtgaggaatg     60
gtggggagtt atttttagag cggtgaggaa ggtgggcagg cagcaggtgt tggcgctcta    120
aaaataactc ccgggagtta tttttagagc ggaggaatgg tggacaccca aatatggcga    180
cggttcctca cccgtcgcca tatttgggtg tccgccctcg gccggggccg cattcctggg    240
ggccgggcgg tgctcccgcc cgcctcgata aaaggctccg gggccggcgg cggcccacga    300
gctacccgga ggagcgggag gcg                                            323
```

```
<210> SEQ ID NO 4
<211> LENGTH: 153
<212> TYPE: PRT
<213> ORGANISM: artificial sequence
<220> FEATURE:
<223> OTHER INFORMATION: This is an IGF-I amino acid sequence.

<400> SEQUENCE: 4

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
                100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
        130                 135                 140

Ser Ala Gly Asn Lys Asn Tyr Arg Met
145                 150
```

```
<210> SEQ ID NO 5
<211> LENGTH: 2237
<212> TYPE: DNA
```

<213> ORGANISM: artificial sequence
<220> FEATURE:
<223> OTHER INFORMATION: Nucleotide sequence for the skeletal alpha
      actin 3' end.

<400> SEQUENCE: 5

```
ggaattcgat ggcccatcca ttgtccaccg taaatgcttc taaacatgtt tacatgatca      60
ctttgccaac cacactcagg atgacaatct tgtaggttcc aggctgctga ggacctccac     120
cagccatgca actttctatt tgtaacaat tctggttac tgttgctgca aagctccatg      180
tgacacagtg tatgtaaagt gtacataaat taatttattt tacctcgttt tgtttgtttt     240
taaaaccaat gccctgtgga aggaaacata aaacttcaag aagcattaaa tcatcagtca     300
ttctgtcaca cccctaatgc agttgtttct gtcatcattt ccctgggctc ttccatctct     360
cgctgacctg ggactgggtg ctgggctgg gagcaggggt tggggctctc cagggagaga      420
tggcatgggg agagtgatgg gatactgctg gggggggggg actcaccctg ctgtgggctg     480
caggaagccc attggtgcag agagcagcct gggatgccca tgacacgggc acccactgca     540
ccgtgtttct cccatgccca gtagggaaag ggttacgagc gccgttcatt ctcagcttgt     600
gaaggatttt gttgggctca gcctgccaga gcagtagcca ggcatgcctg tgcagctccg     660
agctgtgatg gacagaggca aggctgcagc tgaggccagg tggtgggcac aggttaaatt     720
aagagctttc cactccactt atggaaagcc ctcctgcact caccctgtcc ctggggctgg     780
gggcagccag ggccacttcc tcaccccacc tgacacacaa ggctttgcct gcacagccag     840
gacctcctgt ggccacagac tcttatagat tcgctgtgcc ctaggagacc aggggcttt     900 ccctgcctgg ccttctggcc ccggcgacac tgcaggagct gccctatctg cctcctctta     960
gatggtcctg gcaggaaggc tgcacttggc ttggggctga tccatattac cactgcagta    1020
gggacagcac tgctggaaga aaagatgatt ttcaactgaa cttactatcc aggcaggtta    1080
ttgctttatt gtgatggtgc taagagtgcg ttctttctca ctgtaatgat tttgccctca    1140
tgtgtgaata cactttccaa taacagcaca gcctccaaag ggaatttctg caggaagaga    1200
cagtacctgg tgtgggaagt ccctgtgcag ccctatgtgc ttcaagctga atggctggga    1260
ctggctggga gagcaggatc acatcctttc ttaaaaagac aaacagaagg tagtgtgtga    1320
ccttgctgta tttactatt acgcgttgtt gttcagtggc atacctca acggggatat       1380 ggagagctat ttccccaacc ctcgctgctg gaccctgatc tggggttttc ctgtagctta    1440
agcggtgcca actgcttaag tgattgtaga atcagtaagg ctggaaaaga ccacagatca    1500
ttaagtccaa ctgtcagccc catccccacc gcgcccactg tcactcagtg ccacatccac    1560
gcatttcttg aacatctcca gggacagtga ctccacccgt caccagctgt gcttcagagc    1620
aggcagggtg acagtctcag tgccagttgc atcctgctga agagcttaac agtgcagttt    1680
aacaacggac tgatttgttg atgtggttgc tgaatcagta cgttgagatg tcactaaact    1740
ttttggagat taatttcagg atggaacaca ttcttaaccc tgaaaccagc cttgatttg    1800 ggcttggcat ttgcagaatt tgcaggaaaa gattgtttgg gaacagatga atggaattc     1860 caccaaacag aaaattaaca cttacaccag tttgagtctg tcttcgttc gatatttctt     1920 aagaatctca tcatcctccc tgctcttgga ccagtgctgc tgacaggagg tggaggatca    1980
tcagggtcag catcctcagc atctagggat gtgcactatg tgtgatggtg acactttaga    2040
gaactgcttt gattccccag ggctttccct ctcttccatg cagggctcac tatcagccct    2100
gaaagtccaa ctttctgaac ttccagcacc gtctgctcct ggtaggctgt tccatagagg    2160
ccacagggac tgtagccagg catgaccttt tcccagccgt gctctgaatc cagcactggt    2220
```

```
ggctgggagg cagctct                                                    2237
```

<210> SEQ ID NO 6
<211> LENGTH: 190
<212> TYPE: DNA
<213> ORGANISM: artificial sequence
<220> FEATURE:
<223> OTHER INFORMATION: Nucleic acid sequence of a human growth hormone
      3' UTR.

<400> SEQUENCE: 6

```
gggtggcatc cctgtgaccc ctccccagtg cctctcctgg ccctggaagt tgccactcca     60
gtgcccacca gccttgtcct aataaaatta agttgcatca ttttgtctga ctaggtgtcc    120
ttctataata ttatggggtg gaggggggtg gtatggagca aggggcaagt tgggaagaca    180
acctgtaggg                                                           190
```

<210> SEQ ID NO 7
<211> LENGTH: 215
<212> TYPE: PRT
<213> ORGANISM: Artificial Sequence
<220> FEATURE:
<223> OTHER INFORMATION: Protein sequence of vascular endothelial growth
      factor

<400> SEQUENCE: 7

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg
    210                 215
```

<210> SEQ ID NO 8
<211> LENGTH: 782
<212> TYPE: DNA
<213> ORGANISM: artificial sequence

```
<220> FEATURE:
<223> OTHER INFORMATION: Nucleic acid sequence of a plasmid pUC-18
      origin of replicaiton

<400> SEQUENCE: 8
tcttccgctt cctcgctcac tgactcgctg cgctcggtcg ttcggctgcg gcgagcggta      60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180 ttttccata  ggctccgccc ccctgacgag catcacaaaa atcgacgctc aagtcagagg    240
tggcgaaacc cgacaggact ataaagatac caggcgtttc ccctggaag  ctccctcgtg    300 cgctctcctg ttccgaccct gccgcttacc ggatacctgt ccgcctttct ccttcggga    360 agcgtggcgc tttctcatag ctcacgctgt aggtatctca gttcggtgta ggtcgttcgc    420
tccaagctgg gctgtgtgca cgaaccccc  gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720 ggttttttg  tttgcaagca gcagattacg cgcagaaaaa aaggatctca agaagatcct    780
tt                                                                    782

<210> SEQ ID NO 9
<211> LENGTH: 5
<212> TYPE: DNA
<213> ORGANISM: artificial sequence
<220> FEATURE:
<223> OTHER INFORMATION: This is a NEO ribosomal binding site

<400> SEQUENCE: 9 tcctc                                                                   5
```

INSULIN-LIKE GROWTH FACTOR (IGF-I) PLASMID-MEDIATED SUPPLEMENTATION FOR THERAPEUTIC APPLICATIONS

RELATED APPLICATIONS

This application claims priority to U.S. Provisional Patent Application Ser. No. 60/454,079, entitled "Insulin-Like Growth Factor (IGF-I) Plasmid-Mediated Supplementation For therapeutic Applications," filed on Mar. 12, 2003, the entire content of which is hereby incorporated by reference.

BACKGROUND

The present invention pertains to endocrinology, medicine, and cell biology. More specifically, this invention relates to the endogenous stimulation of production of insulin-like growth factor I ("IGF-I") in a subject at a level greater than non-treated subjects. Administration of DNA encoding IGF-I helps enhance angiogenesis and myogenesis. It also upregulates angiogenic factors, upregulates angiopoietins, and treats complications of diabetes.

IGF-I has important growth promoting and metabolic effects and is expressed in virtually every tissue of the body. The highest expression is found in the liver. The effects of liver-derived and systemically secreted IGF-I are predominantly endocrine, while locally produced IGF-I in peripheral tissues has more of an autocrine or paracrine effect. Recent studies have been aimed to elucidate the role and effects of systemically or locally produced IGF-I. Data in the literature suggests that the liver-derived IGF-I is important for carbohydrate- and lipid-metabolism and for the regulation of GH-secretion at the pituitary level. Furthermore, it regulates adult axial skeletal growth and cortical radial growth while it is not required for appendicular skeletal growth, which is linked to locally-derived IGF-I (Sjogren et al., 1999; Sjogren et al., 2002).

The GHRH-GH-IGF-I production pathway is composed of a series of interdependent genes whose products are required for normal growth, development, regeneration and repair (Caroni et al., 1994). The pathway genes include: (1) ligands, such as growth hormone ("GH") and IGF-I; (2) transcription factors such as prophet of Pit-1, or prop 1, and Pit-1; (3) agonists and antagonists, such as growth hormone releasing hormone ("GHRH") and somatostatin ("SS"), respectively; and (4) receptors, such as the GHRH receptor ("GHRH-R") and the GH receptor ("GH-R"). These genes are expressed in different organs and tissues, including the hypothalamus, pituitary, liver, and bone.

IGF-I is a 70 amino acid polypeptide with extensive structural homology to insulin (49%) and IGF-II (61%). Hormonally, IGF-I is regulated as part of the GHRH/GH axis. GHRH, secreted by the hypothalamus, stimulates release of GH by the anterior pituitary. GH subsequently stimulates production of IGF-I in the liver and other tissues. IGF-I provides negative feedback in this axis by directly inhibiting GH release from the pituitary and indirectly by inducing somatostatin ("SS") expression by the hypothalamus (Vance, 1990). The possibility of a direct regulatory role of this axis with respect to any autocrine or endocrine effects of IGF-I remains to be proven. IGFs were originally thought to be liver-derived mediators of GH action, but now it is known that they are synthesized and secreted from many cell types, including muscle or bone (Florini et al., 1991). This factor mediates many of the growth-promoting effects of GH in postnatal animals by binding to the type I IGF receptor ("IGF-R"). In animal studies, administration of GH to hypophysectomized rats resulted in a significant increase in IGF-I mRNA in skeletal muscle. Implantation of GH secreting cells in non-growing rats caused a seven-fold increase in IGF-I mRNA and a 50% increase in the mass of the gastrocnemius muscles (Kelly et al., 1990). Increased expression of IGF-I genes by passive mechanical stretch or acute exercise shows a correspondence between muscle hypertrophy and IGFs (Vandenburgh et al., 1991). Targeted over-expression of IGF-I in skeletal muscle in transgenic animals enhances muscle growth (Coleman et al., 1995; Goldspink, 1999). Thus, IGF-I seems to be important in the hormonal regulation of skeletal muscle growth.

IGF-I provides an attractive candidate for therapeutic approaches on muscle and heart. IGF-I was shown to play an important role in the growth and regeneration of peripheral nerves and skeletal muscle, and it was investigated as a treatment for neuromuscular disorders (Cheng et al., 1996; Florini et al., 1993). In addition, expression of IGF-I in skeletal muscle is increased coincident with stretch-induced myofiber overloading and hypertrophy (Goldspink, 1999) and muscle regeneration following injury (Kasemkijwattana et al., 1998; Menetrey et al., 2000). Treatment with exogenous IGF-I protein reduces muscle degeneration and atrophy in dystrophic mice (De Luca et al., 1999; Hsu et al., 1997).

In addition to its role in myogenesis and nerve regeneration, IGF-I is also a potential angiogenic factor. Angiogenesis, the formation of neo-vessels from the endothelium of pre-existing vessels, plays an essential role in embryonic development and tissue repair (Folkman, 1995). Neo-vessels form in response to stimulation by soluble angiogenic factors, which regulate endothelial migration, proliferation, survival, and proteolytic activity (Folkman and Klagsbrun, 1987). The most well-studied factors described to date, vascular endothelial growth factor ("VEGF"), fibroblast growth factor ("bFGF") and the angiopoietins (ANG-1, ANG-2), have emerged as critical regulators of the angiogenic process (Davis et al., 2003; Horvath et al., 2002). These molecules promote neo-vessel formation and morphogenesis by cooperating closely through a carefully orchestrated sequence of angioregulatory events (Peters, 1998; Veikkola et al., 2000). Current therapeutic angiogenesis strategy by using angiogenic growth factors had some success in treating ischemic disease, as peripheral diabetic disease, diabetic retinopathy or age-related macular degeneration (major causes of blindness in the western world), accelerate healing, as well as cardiac ischemic disease (Silvestre and Levy, 2002). As many as 10 million people in the USA have peripheral arterial disease ("PAD") with more than 10% prevalence in people over 60 years old. Generally, men have a higher prevalence of PAD than women. The risk factors for PAD are similar to those for coronary artery disease ("CAD") and cerebrovascular disease ("CBVD"), but diabetes and cigarette smoking have a particularly strong association with PAD (Beckman et al., 2002; Criqui 2001; Fowler et al., 2002).

IGF-I may be an initiator of the angiogenic process. IGF-I receptors have been shown to be present on endothelial cells of bone (Fiorelli et al., 1994; Fiorelli et al., 1996), retina (Spoerri et al., 1998), and aorta (Kobayashi and Kamata, 2002). IGF-I has also been shown to induce the expression of VEGF mRNA on retinal pigment epithelial cells (Punglia et al., 1997), osteoblasts (Akeno et al., 2002; Goad et al., 1996), vascular endothelial cells (Miele et al., 2000), and in a variety of tumor cells (Bermont et al., 2000; Reinmuth et al., 2002; Wu et al., 2002). IGF-I induces cell migration and tubular formation of cultured bovine retinal endothelial cells and human endothelial cells in vitro (Castellon et al., 2002; Shigematsu et al., 1999). Increased branching of aged cultured micro-vessels is enhanced by IGF-I (Arthur et al., 1998).

IGF-I acts as a vasoactive factor by inhibiting vessel contraction, via stimulation of nitric oxide production (Walsh et al., 1996). During muscle regeneration, angiogenesis is induced in order to vascularize the growing muscle. IGF-I induces muscle satellite cell proliferation and differentiation in vivo (Rabinovsky et al., 2003) and it is known that IGF-I induces VEGF expresssion in satellite cells. Therefore, IGF-I initiates the angiogenic pathways that occur in injured muscle.

In additon to inducing aniogenesis in skeletal muscle, studies suggest that IGF-I may also induce aniogenesis in the heart. Studies show that IGF-I is capable of inducing a hypertrophic response in the heart by stimulating cardiac myocytes and fibroblasts to initiate a variety of processes associated with hypertrophy. IGF-I's activities were demonstrated in both in vitro and in vivo model systems. In cultured neonatal ventricular myocytes, the addition of IGF-I induces DNA synthesis (Kajstura et al., 1994; Kardami, 1990), the transcription of several genes associated with hypertrophy and hyperplasia, including myosin light chain-2, troponin and α-skeletal actin (Ito et al., 1993), and in vitro increased myofibril production (Donath et al., 1994; Donath et al., 1997). In vivo, IGF-I and its receptor are upregulated in cardiomyocytes of experimentally infarcted ventricles. This may be followed by DNA replication and mitotic division of a portion of the remaining cardiomyocytes (Reiss et al., 1994). IGF-I protects against apoptosis in cultured and primary cardiomyocytes (Wang et al., 1998b; Wang et al., 1998a) and in a mouse model of ischemic injury (Buerke et al., 1995). A transgenic mouse with increased IGF-I serum levels exhibits cardiomyocyte hyperplasia but no hypertrophy (Reiss et al., 1996). IGF-I and GH have been shown to improve cardiac performance in both experimental cardiac failure (Duerr et al., 1996) and that developed in human patients (Donath et al., 1998). Consequently, IGF-I and GH are seriously considered as potential therapeutic agents for situations in which hypertrophy and/or hyperplasia of cardiomyocytes would be desirable, such as following myocardial infarction or in hypocontracting cardiomyopathies (Lombardi et al., 1997). Adequate vascularization of the myocardium in this case is critical.

Although previous research demonstrated that IGF-I has potential for treatment of different conditions, systemic administration of IGF-I protein may require frequent dosing and elicit numerous side effects. For instance, recombinant IGF-I given to diabetic patients resulted in adverse effects such as edema and tachycardia (Jabri et al., 1994). Increased serum IGF-I levels may also accelerate the progression of diabetic nephropathy (Zhuang et al., 1996) and proliferative retinopathy (Glazner et al., 1994). In contrast to systemic delivery of IGF-I protein, non-viral IGF-I gene delivery targeted to skeletal muscle offers the potential to provide sustained and localized expression of IGF-I with infrequent administration and with minimal systemic side effects (Alila et al., 1997).

During the aging process, mammals lose up to a third of their skeletal muscle mass and strength. The injection of a recombinant adeno-associated virus directing over-expression of IGF-I in differentiated muscle fibers promotes an average increase of 15% in muscle mass and a 14% increase in strength in young adult mice, and prevents aging-related muscle changes in elderly adult mice, resulting in a 27% increase in strength as compared with uninjected aged muscles. Muscle mass and fiber-type distributions are maintained at levels similar to those in young adults. These effects may primarily be due to stimulation of muscle regeneration via the activation of satellite cells by IGF-I (Barton-Davis et al., 1998).

Muscle injuries are a challenging problem in traumatology, and the most frequent occurrence in sports medicine. In mice, massive muscle regeneration occurs in the first 2 weeks post injury that is subsequently followed by the development of muscle fibrosis. Growth factors, as bFGF, IGF-I, and NGF are capable of stimulating myoblast proliferation and differentiation in vitro and improving the healing of the injured muscle in vivo. Adenoviruses have been used to mediate direct and ex vivo gene transfer of these growth factors in the injured muscle (Kasemkijwattana et al., 1998). Liposome IGF-I gene transfer accelerates wound healing in burned rats and attenuates deleterious side effects associated with high levels of IGF-I. Rats receiving weekly subcutaneous injections of liposomes and IGF-I constructs exhibited the most rapid wound re-epithelialization and greatest increase in body weight and gastrocnemius muscle protein content (Jeschke et al., 1999). Intramuscular injection of a plasmid encoding human IGF-I ("hIGF-I") and engineered to restrict expression to skeletal muscle produced sustained local concentrations of biologically active hIGF-I. When normal rats received a single intramuscular injection of plasmids formulated as a complex with polyvinylpyrrolidone ("PVP"), the results showed that hIGF-I mRNA and hIGF-I protein were detectable in the injected muscles for the duration of the study. Biological activity of hIGF-I was determined by immunodetection of a nerve-specific growth-associated protein, GAP43, an indicator of motor neuron sprouting (Alila et al., 1997).

Gene transfer into skeletal muscle holds promise for the treatment of a variety of serum protein deficiencies, muscular dystrophies, and chronic ischemic limb syndromes. It is currently being developed as a method for the production, secretion and delivery of physiologically active proteins as hormones and may ultimately be applied to the treatment of several diseases (MacColl et al., 1999). The past few years have seen the development of new and improved vectors for programming recombinant gene expression in skeletal muscle. Important advances include first, novel plasmid DNA, adenovirus, and adeno-associated virus vectors that can be used to express stably therapeutic levels of recombinant proteins in the skeletal muscle of immunocompetent hosts and second, the development of vector systems that enable regulated and tissue-specific transgene expression in skeletal muscle in vivo.

Direct plasmid DNA gene transfer is currently the basis of many emerging nucleic acid therapy strategies and thus does not require viral genes or lipid particles (Aihara and Miyazaki, 1998; Muramatsu et al., 2001). Skeletal muscle is the target tissue of choice, because muscle fiber has a long life span and can be transduced by circular DNA plasmids that express over months or years in an immunocompetent host (Davis et al., 1993; Tripathy et al., 1996).

Recently, the delivery of specific genes to somatic tissue in a manner that can correct inborn or acquired deficiencies and imbalances was proven to be possible (Herzog et al., 2001; Song et al., 2001; Vilquin et al., 2001). Gene-based drug delivery offers a number of advantages over the administration of recombinant proteins. These advantages include the conservation of native protein structure, improved biological activity, avoidance of systemic toxicities, and avoidance of infectious and toxic impurities. In addition, nucleic acid vector therapy allows for prolonged exposure to the protein in the therapeutic range, because the newly secreted protein is present continuously in the blood circulation. In a few cases, the relatively low expression levels achieved after simple plasmid injection are sufficient to reach physiologically acceptable levels of bioactivity of secreted peptides, especially for vaccine purposes (Danko and Wolff, 1994; Tsurumi et al., 1996).

The primary limitation of using recombinant protein is the limited availability of protein after each administration. Nucleic acid vector therapy using injectable DNA plasmid vectors overcomes this, because a single injection into the patient's skeletal muscle permits physiologic expression for extensive periods of time (WO 99/05300 and WO 01/06988). Injection of the vectors promotes the production of enzymes and hormones in animals in a manner that more closely mimics the natural process.

In a plasmid-based expression system, a non-viral gene vector may be composed of a synthetic gene delivery system in addition to the nucleic acid encoding a therapeutic gene product. In this way, the risks associated with the use of most viral vectors can be avoided, including the expression of viral proteins that can induce immune responses against target tissues and the possibility of DNA mutations or activations of oncogenes. The non-viral expression vector products generally have low toxicity due to the use of "species-specific" components for gene delivery, which minimizes the risks of immunogenicity generally associated with viral vectors. Additionally, no integration of plasmid sequences into host chromosomes has been reported in vivo to date, so that this type of nucleic acid vector therapy should neither activate oncogenes nor inactivate tumor suppressor genes. As episomal systems residing outside the chromosomes, plasmids have defined pharmacokinetics and elimination profiles, leading to a finite duration of gene expression in target tissues.

Among the non-viral techniques for gene transfer in vivo, the direct injection of plasmid DNA into muscle is simple, inexpensive, and safe. However, the use of directly injectable DNA plasmid vectors has been limited in the past. The inefficient DNA uptake into muscle fibers after simple direct injection has led to relatively low expression levels (Prentice et al., 1994; Wells et al., 1997). In addition, the duration of the transgene expression has been short (Wolff et al., 1990). The most successful previous clinical applications have been confined to vaccines (Danko and Wolff, 1994; Tsurumi et al., 1996). A vector system for the delivery and controlled expression of recombinant IGF-I genes was previously described in U.S. patent application Ser. No. 09/861,101. This vector system included a 5' flanking region with a naturally-occurring promoter, a linker region providing a site for insertion of a nucleic acid sequence and connecting the 5' flanking region to the nucleic acid sequence, a nucleic acid sequence encoding IGF-I, and a 3' flanking region. Administration of the vector system involved direct or intravenous injection and was shown to improve nerve regeneration, treat muscle atrophy, treat diabetes, treat osteoporosis, and improve livestock.

Efforts have been made to enhance the delivery of plasmid DNA to cells by physical means including electroporation, sonoporation, and pressure. Administration by electroporation involves the application of a pulsed electric field to create transient pores in the cellular membrane without causing permanent damage to the cell. It thereby allows for the introduction of exogenous molecules (Smith and Nordstrom, 2000). By adjusting the electrical pulse generated by an electroporetic system, nucleic acid molecules can travel through passageways or pores in the cell that are created during the procedure. U.S. Pat. No. 5,704,908 describes an electroporation apparatus for delivering molecules to cells at a selected location within a cavity in the body of a patient. These pulse voltage injection devices are also described in U.S. Pat. Nos. 5,439,440 and 5,702,384, and PCT WO 96/12520, 96/12006, 95/19805, and 97/07826.

Recently, significant progress to enhance plasmid delivery in vivo and subsequently to achieve physiological levels of a secreted protein was obtained using the electroporation technique. Electroporation has been used very successfully to transfect tumor cells after injection of plasmid (Lucas et al., 2002; Matsubara et al., 2001) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Previous studies using growth hormone releasing hormone (GHRH) showed that plasmid therapy with electroporation is scalable and represents a promising approach to induce production and regulated secretion of proteins in large animals and humans (Draghia-Akli et al., 1999; Draghia-Akli et al., 2002). Electroporation also has been extensively used in rodents and other small animals (Bettan et al., 2000; Yin and Tang, 2001). It has been observed that the electrode configuration affects the electric field distribution, and subsequent results (Gehl et al., 1999; Miklavcic et al., 1998). Preliminary experiments indicated that for a large animal model, needle electrodes give consistently better reproducible results than external caliper electrodes.

The ability of electroporation to enhance plasmid uptake into the skeletal muscle has been well documented, as described above. In addition, plasmid formulated with poly-L-glutamate ("PLG") or polyvinylpyrrolidone ("PVP") has been observed to increase plasmid transfection and consequently expression of the desired transgene. The anionic polymer sodium PLG could enhance plasmid uptake at low plasmid concentrations, while reducing any possible tissue damage caused by the procedure. PLG is a stable compound and resistant to relatively high temperatures (Dolnik et al., 1993). PLG has been previously used to increase stability in vaccine preparations (Matsuo et al., 1994) without increasing their immunogenicity. It also has been used as an anti-toxin after antigen inhalation or exposure to ozone (Fryer and Jacoby, 1993). In addition, plasmid formulated with PLG or PVP has been shown to increase gene transfection and consequently gene expression to up to 10 fold in the skeletal muscle of mice, rats and dogs (Fewell et al., 2001; Mumper et al., 1998). PLG has been used to increase stability of anti-cancer drugs (Li et al., 2000) and as "glue" to close wounds or to prevent bleeding from tissues during wound and tissue repair (Otani et al., 1996; Otani et al., 1998).

Although not wanting to be bound by theory, PLG increases the transfection of the plasmid during the electroporation process, not only by stabilizing the plasmid DNA, and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, a process that substantially increases the transfection efficiency. Furthermore, PLG will prevent the muscle damage associated with in vivo plasmid delivery (Draghia-Akli et al., 2002a) and will increase plasmid stability in vitro prior to injection.

Although there are references in the art directed to electroporation of eukaryotic cells with linear DNA (McNally et al., 1988; Neumann et al., 1982; Toneguzzo et al., 1988; Aratani et al., 1992; Nairn et al., 1993; Xie and Tsong, 1993; Yorifuji and Mikawa, 1990), these examples illustrate transfection into cell suspensions, cell cultures, and the like, and the transfected cells are not present in a somatic tissue.

U.S. Pat. No. 4,956,288 is directed to methods for preparing recombinant host cells containing high copy number of a foreign DNA by electroporating a population of cells in the presence of the foreign DNA, culturing the cells, and killing the cells having a low copy number of the foreign DNA.

In summary, increased angiogenesis and myogenesis in a treated subject were previously restricted in scope. The related art has shown that it is possible to improve these different conditions in a limited capacity utilizing recombinant protein technology, but these treatments have some significant drawbacks. It has also been shown that nucleic acid expression constructs that encode recombinant proteins are viable solutions to the problems of frequent injections and high cost of traditional recombinant therapy. Unfortunately, each plasmid construct for a given recombinant protein must be evaluated individually, because the related art does not teach one skilled in the art to accurately predict how changes in structure (e.g. amino-acid sequences) will lead to changed functions (e.g. increased or decreased stability) of a recombinant protein. Therefore, the beneficial effects of nucleic acid expression constructs that encode expressed proteins can only be ascertained through direct experimentation. There is a need in the art for expanded treatments for subjects with a disease by utilizing nucleic acid expression constructs that are delivered into a subject and express stable therapeutic proteins in vivo.

SUMMARY

One embodiment of the present invention relates to a method for stimulating endogenous production of insulin-like growth factor I ("IGF-I") in a subject at a level greater than non-treated subjects through plasmid-mediated gene supplementation. An effective amount of a vector, including a synthetic myogenic promoter, a nucleotide sequence, and a 3' untranslated region, is introduced into cells of the subject. The nucleotide sequence encodes IGF-I or a functional biological equivalent thereof. When the nucleotide sequence is introduced and expressed in the specific cells of the subject (e.g. somatic cells, stem cells, or germ cells), endogenous production of IGF-I is increased. By delivering the nucleic acid expression construct into cells of the subject, angiogenesis and myogenesis may be enhanced, and muscular and vascular complications of diabetes may be treated.

Another embodiment of the present invention relates to elements of the nucleic acid expression construct. For example, the construct includes a synthetic myogenic promoter, an IGF-I or functional biological equivalent, and a 3' untranslated region ("3'UTR") that are operatively linked. A preferred embodiment of the nucleic acid expression construct is substantially free of a viral backbone. The encoded functional biological equivalent of IGF-I is a polypeptide having similar or improved biological activity when compared to the native IGF-I polypeptide. When the nucleic acid sequence is delivered into the specific cells of the subject, tissue specific and constitutive expression of IGF-I is achieved.

The present invention also relates to the application of a nucleotide sequence that upregulates angiogenic factors, such as VEGF and VEGF receptors (FLK-1 and FLT-1), upregulates angiopoietins (ANG-1 and ANG-2), and promotes angiogenesis. The nucleotide sequence may be regulated by a muscle-specific promoter into muscle tissue and may be administered using electroporation techniques. The preferred method to deliver the nucleic acid sequence with the constitutive promoter and the encoding sequence of IGF-I or the biological equivalent thereof is directly into the cells of the subject by the process of in vivo electroporation. Electroporation may involve externally supplied electrodes, or in the case of needles, internally supplied electrodes to aid in the inclusion of desired nucleotide sequences into the cells of a subject while the cells are within a tissue of the subject.

In a further specific embodiment, the 3' untranslated region comprises a 3' untranslated region of the skeletal alpha actin gene or the 3' untranslated region of human growth hormone. In another specific embodiment, the vector is introduced into said cells of said animal by electroporation, through a viral vector, or in conjunction with a carrier. The nucleic acid construct may also be introduced to the cells with a transfection-facilitating polypeptide, which may be charged and may be poly-L-glutamate. In an additional specific embodiment, the animal is a human, a pet animal, a farm animal, a food animal, or a work animal. In a further specific embodiment, the animal is a human, pig, cow, sheep, goat or chicken. In an additional specific embodiment, the vector is a plasmid, a viral vector, a liposome, or a cationic lipid. In another specific embodiment, the vector is introduced into the animal in a single administration. In another specific embodiment, a ligand is administered to the animal for induction of IGF-I expression.

Other and further objects, features and advantages would be apparent and eventually more readily understood by reading the following specification and by reference to the accompanying drawings forming a part thereof, or any examples of the presently preferred embodiments of the invention given for the purpose of the disclosure.

DETAILED DESCRIPTION

Figure 1:
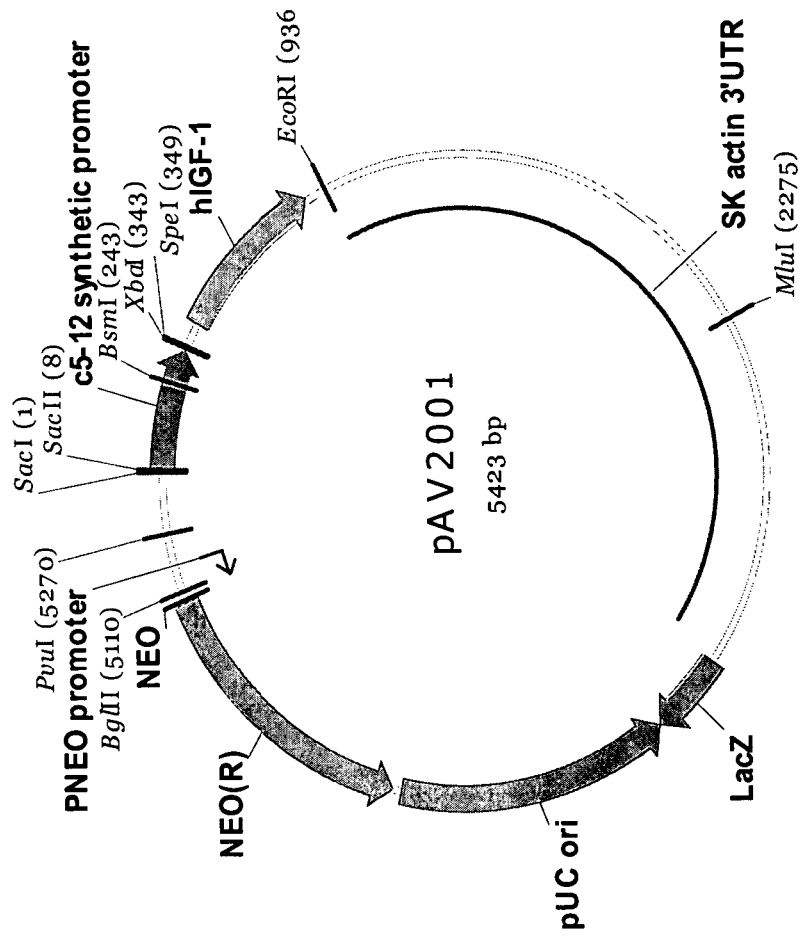
FIG. 1 illustrates the vector pAV2001 (SEQ ID NO.: 1), or pSP-IGF-I-SK3'UTR, which includes the 3'UTR of skeletal alpha actin.

It will be readily apparent to one skilled in the art that various substitutions and modifications may be made in the invention disclosed herein without departing from the scope and spirit of the invention.

The term "a" or "an" as used herein in the specification may mean one or more. As used herein in the claim(s), when used in conjunction with the word "comprising," the words "a" or "an" may mean one or more than one. As used herein "another" may mean at least a second or more.

The term "analog" as used herein includes any mutant of IGF-I, or synthetic or naturally occurring peptide fragments of IGF-I.

The term "angiogenesis" as used herein is defined as formation of new blood vessels from the endothelium of pre-existing vessels.

The term "cassette" as used herein is defined as one or more transgene expression vectors.

The term "cell-transfecting pulse" as used herein is defined as a transmission of a force which results in transfection of a vector, such as a linear DNA fragment, into a cell. In some embodiments, the force is from electricity, as in electroporation, or the force is from vascular pressure.

The term "coding region" as used herein refers to any portion of the DNA sequence that is transcribed into messenger RNA (mRNA) and then translated into a sequence of amino acids characteristic of a specific polypeptide.

The term "a conservative amino acid substitution" as used herein refers to a replacement of one amino acid residue with a different residue having similar biochemical characteristics, such as size, charge, and polarity vs. non-polarity. Such conservative amino acid groupings are well defined in the art, and can be found in most basic biochemistry textbooks.

The term "delivery" or "delivering" as used herein is defined as a means of introducing a material into a tissue, a subject, a cell or any recipient, by means of chemical or biological process, injection, mixing, electroporation, sonoporation, or combination thereof, either under or without pressure.

The term "DNA fragment" or "nucleic acid expression construct" as used herein refers to a substantially double stranded DNA molecule. Although the fragment may be generated by any standard molecular biology means known in the art, in some embodiments the DNA fragment or expression construct is generated by restriction digestion of a parent DNA molecule. The terms "expression vector," "expression cassette," or "expression plasmid" can also be used interchangeably. Although the parent molecule may be any standard molecular biology DNA reagent, in some embodiments the parent DNA molecule is a plasmid.

The term "donor-subject" as used herein refers to any species of the animal kingdom wherein cells have been removed and maintained in a viable state for any period of time outside the subject.

The term "donor-cells" as used herein refers to any cells that have been removed and maintained in a viable state for any period of time outside the donor-subject.

The term "electroporation" as used herein refers to a method that utilized electric pulses to deliver a nucleic acid sequence into cells.

The terms "electrical pulse" and "electroporation" as used herein refer to the administration of an electrical current to a tissue or cell for the purpose of taking up a nucleic acid molecule into a cell. A skilled artisan recognizes that these terms are associated with the terms "pulsed electric field" "pulsed current device" and "pulse voltage device." A skilled artisan recognizes that the amount and duration of the electrical pulse is dependent on the tissue, size, and overall health of the recipient subject, and furthermore knows how to determine such parameters empirically.

The term "encoded IGF-I" as used herein is a biologically active polypeptide of insulin-like growth factor-I.

The term "functional biological equivalent" of IGF-I as used herein is a polypeptide that has a distinct amino acid sequence from a wild type IGF-I polypeptide while simultaneously having similar or improved biological activity when compared to the IGF-I polypeptide. The functional biological equivalent may be naturally occurring or it may be modified by an individual. A skilled artisan recognizes that the similar or improved biological activity as used herein refers to facilitating and/or releasing IGF-I and stimulating angiogenesis. Methods known in the art to engineer such a sequence include site-directed mutagenesis.

The term "growth hormone releasing hormone" ("GHRH") as used herein is defined as a hormone that facilitates or stimulates release of growth hormone, and in a lesser extent other pituitary hormones, as prolactin.

The term "growth hormone" ("GH") as used herein is defined as a hormone that relates to growth and acts as a chemical messenger to exert its action on a target cell. In a specific embodiment, the growth hormone is released by the action of growth hormone releasing hormone.

The term "insulin-like growth factor-I" (IGF-I") as used herein is defined as a hormone that related to growth, regeneration, embryonic development and tissue repair. In a specific embodiment, the insulin-like growth factor-I is released by the action of growth hormone.

The term "GeneSwitch®" (a registered trademark of Valentis, Inc.; Burlingame, Calif.) as used herein refers to the technology of a mifepristone-inducible heterologous nucleic acid sequences encoding regulator proteins, IGF-I biological equivalent or combination thereof. A skilled artisan recognizes that antiprogesterone agent alternatives to mifepristone are available, including onapristone, ZK112993, ZK98734, and 5α-pregnane-3,2-dione.

The term "heterologous nucleic acid sequence" as used herein is defined as a DNA sequence comprising differing regulatory and expression elements.

The term "modified cells" as used herein is defined as the cells from a subject that have an additional nucleic acid sequence introduced into the cell.

The term "modified-donor-cells" as used herein refers to any donor-cells that have had a IGF-I-encoding nucleic acid sequence delivered.

The term "molecular switch" as used herein refers to a molecule that is delivered into a subject that can regulate transcription of a gene.

The term "myogenic promoter" as used herein refers to a nucleic acid sequence that is operably linked to a heterologous coding sequence having expression control activity in myogenic tissue.

The term "nucleic acid expression construct" as used herein refers to any type of genetic construct comprising a nucleic acid coding for a RNA capable of being transcribed. The term "expression vector" can also be used interchangeably herein. In specific embodiments, the nucleic acid expression construct comprises: a promoter; a nucleotide sequence of interest; and a 3' untranslated region; wherein the promoter, the nucleotide sequence of interest, and the 3' untranslated region are operatively linked; and in vivo expression of the nucleotide sequence of interest is regulated by the promoter.

The term "operatively linked" as used herein refers to elements or structures in a nucleic acid sequence that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The term "poly-L-glutamate ("PLG")" as used herein refers to a biodegradable polymer of L-glutamic acid that is suitable for use as a vector or adjuvant for DNA transfer into cells with or without electroporation.

The term "post-injection" as used herein refers to a time period following the introduction of a nucleic acid cassette that contains heterologous nucleic acid sequence encoding IGF-I or a biological equivalent thereof into the cells of the subject and allowing expression of the encoded gene to occur while the modified cells are within the living organism.

The term "plasmid" as used herein refers generally to a construction comprised of extra-chromosomal genetic material, usually of a circular duplex of DNA that can replicate independently of chromosomal DNA. Plasmids, or fragments thereof, may be used as vectors. Plasmids are double-stranded DNA molecules that occur or are derived from bacteria and (rarely) other microorganisms. However, mitochondrial and chloroplast DNA, yeast killer and other cases are commonly excluded.

The term "plasmid mediated gene supplementation" as used herein refers a method to allow a subject to have prolonged exposure to a therapeutic range of a therapeutic protein by utilizing a nucleic acid expression construct in vivo.

The term "pulse voltage device," or "pulse voltage injection device" as used herein relates to an apparatus that is capable of causing or causes uptake of nucleic acid molecules into the cells of an organism by emitting a localized pulse of electricity to the cells. The cell membrane then destabilizes, forming passageways or pores. Conventional devices of this type are calibrated to allow one to select or adjust the desired voltage amplitude and the duration of the pulsed voltage. The primary importance of a pulse voltage device is the capability of the device to facilitate delivery of compositions of the invention, particularly linear DNA fragments, into the cells of the organism.

The term "plasmid backbone" as used herein refers to a sequence of DNA that typically contains a bacterial origin of replication, and a bacterial antibiotic selection gene, which are necessary for the specific growth of only the bacteria that are transformed with the proper plasmid. However, there are plasmids, called mini-circles, that lack both the antibiotic resistance gene and the origin of replication (Darquet et al., 1997; Darquet et al., 1999; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is that the plasmid backbone does not contain viral nucleotide sequences.

The term "promoter" as used herein refers to a sequence of DNA that directs the transcription of a gene. A promoter may direct the transcription of a prokaryotic or eukaryotic gene. A promoter may be "inducible," initiating transcription in response to an inducing agent or, in contrast, a promoter may be "constitutive," whereby an inducing agent does not regulate the rate of transcription. A promoter may be regulated in a tissue-specific or tissue-preferred manner, such that it is only active in transcribing the operable linked coding region in a specific tissue type or types.

The term "replication element" as used herein comprises nucleic acid sequences that will lead to replication of a plasmid in a specified host. One skilled in the art of molecular biology will recognize that the replication element may include but is not limited to a selectable marker gene promoter, a ribosomal binding site, a selectable marker gene sequence, and a origin of replication.

The term "residual linear plasmid backbone" as used herein comprises any fragment of the plasmid backbone that is left at the end of the process making the nucleic acid expression plasmid linear.

The term "recipient-subject" as used herein refers to any species of the animal kingdom wherein modified-donor-cells can be introduced from a donor-subject.

The term "regulator protein" as used herein refers to any protein that can be used to control the expression of a gene.

The terms "subject" or "animal" as used herein refers to any species of the animal kingdom. In preferred embodiments, it refers more specifically to humans and domesticated animals used for: pets (e.g. cats, dogs, etc.); work (e.g. horses, etc.); food (cows, chicken, fish, lambs, pigs, etc); and all others known in the art.

The term "tissue" as used herein refers to a collection of similar cells and the intercellular substances surrounding them. A skilled artisan recognizes that a tissue is an aggregation of similarly specialized cells for the performance of a particular function. For the scope of the present invention, the term tissue does not refer to a cell line, a suspension of cells, or a culture of cells. In a specific embodiment, the tissue is electroporated in vivo. A skilled artisan recognizes that there are four basic tissues in the body: 1) epithelium; 2) connective tissues, including blood, bone, and cartilage; 3) muscle tissue; and 4) nerve tissue. In a specific embodiment, the methods and compositions are directed to transfer of DNA into a muscle tissue by electroporation.

The term "therapeutic element" as used herein comprises nucleic acid sequences that will lead to an in vivo expression of an encoded gene product. One skilled in the art of molecular biology will recognize that the therapeutic element may include, but is not limited to, a promoter sequence, a transgene, a poly A sequence, or a 3' or 5' UTR.

The term "transfects" as used herein refers to introduction of a nucleic acid into a eukaryotic cell. In some embodiments, the cell is not a plant tissue or a yeast cell.

The term "vascular endothelial growth factor" ("VEGF") as used herein refers to a growth factor that promotes angiogenesis and vasculogenesis, and is involved in the maturation of blood vessels.

The term "vector" as used herein refers to any vehicle that delivers a nucleic acid into a cell or organism. Examples include plasmid vectors, viral vectors, liposomes, or cationic lipids.

The term "viral backbone" as used herein refers to a nucleic acid sequence that does not contain a promoter, a gene, and a 3' poly A signal or an untranslated region, but contains elements including, but not limited to, site-specific genomic integration Rep, inverted terminal repeats ("ITRs"), and the binding site for the tRNA primer for reverse transcription. It may also contain a nucleic acid sequence component that induces a viral immunogenicity response when inserted in vivo, allow integration, affect specificity and activity of tissue specific promoters, cause transcriptional silencing, or pose safety risks to the subject.

The term "vascular pressure pulse" refers to a pulse of pressure from a large volume of liquid to facilitate uptake of a vector into a cell. A skilled artisan recognizes that the amount and duration of the vascular pressure pulse is dependent on the tissue, size, and overall health of the recipient animal, and furthermore knows how to determine such parameters empirically.

The term "vector" as used herein refers to a construction comprised of genetic material designed to direct transformation of a targeted cell by delivering a nucleic acid sequence into that cell. A vector may contain multiple genetic elements positionally and sequentially oriented with other necessary elements such that an included nucleic acid cassette can be transcribed and when necessary translated in the transfected cells. These elements are operatively linked. The term "expression vector" refers to a DNA plasmid that contains all of the information necessary to produce a recombinant protein in a heterologous cell.

One aspect of the current invention pertains to a method useful for increasing endogenous IGF-I production and consequently angiogenesis in an animal. A preferred embodiment includes delivering a nucleic acid expression construct that encodes an insulin-like growth factor-I ("IGF-I") or functional biological equivalent thereof into a tissue of the subject. The preferred means for delivering the nucleic acid expression construct is by electroporation. The nucleic acid expression construct may also be delivered in a single administration. In a preferred embodiment, the nucleic acid expression construct is delivered into somatic cells, stem cells, or germ cells of the subject. The cells may also be diploid cells. Delivery of the nucleic acid construct initiates expression of the encoded IGF-I or functional biological equivalent thereof. The encoded IGF-I or functional biological equivalent thereof is then expressed in tissue specific cells of the subject, which may be muscle cells. The encoded IGF-I is a biologically active polypeptide, and the encoded functional biological equivalent of IGF-I is a polypeptide engineered to contain a distinct amino acid sequence while simultaneously having similar or improved biological activity when compared to the IGF-I polypeptide. In a preferred embodiment, a ligand for a regulator of IGF-I is administered with the nucleic acid expression construct. The subject in this invention may be a human, a pet animal, a farm animal, a food animal, or a work animal.

Specific elements of the nucleic acid expression construct of this invention are also described. For example, the construct comprises a synthetic myogenic promoter, a sequence encoding IGF-I or a functional biological equivalent, and a 3' untranslated region ("3'UTR") that are operatively linked. In specific embodiments, the 3' UTR of the nucleic acid expression construct is a human growth hormone 3'UTR or skeletal alpha actin 3'UTR. The nucleic acid expression construct of this invention is a construct that is substantially free of a viral backbone. A transfection-facilitating vector system may also be used for delivery of the nucleic acid expression construct. In preferred embodiments, the transfection-facilitating vector system can be a plasmid, a viral vector, a liposome, or a cationic lipid. In another specific embodiment the nucleic acid expression construct comprises SEQ ID NO: 1 or SEQ ID NO: 2. In additional specific embodiments, the nucleic acid expression construct may also include a transfection-facilitating polypeptide. The transfection-facilitating polypeptide may be charged and is preferably poly-L-glutamate.

Specific embodiments of this invention are also directed toward stimulating myogenesis in a subject by delivering the nucleic acid expression construct into cells of the subject. Additional embodiments are directed to upregulation of angiogenic factors, such as VEGF, VEGF receptors (FLK-1 and FLT-1), and the angiopoietins (ANG-1 and ANG-2) through delivery of the nucleic acid expression construct. Further embodiments include methods for treating the muscular and vascular complications of diabetes.

The use of plasmid mediated therapy to expedite or augment collateral vessel development holds great promise in the treatment of limb and myocardial ischemia. A new strategy for therapeutic angiogenesis uses IGF-I plasmid mediated therapy. Injection of a vector encoding IGF-I under the control of a muscle synthetic promoter, followed by the 3'UTR of the skeletal alpha actin gene (SP-IGF-I-SK3'UTR), followed by electroporation into the tibialis anterior muscle of mice results in induction of VEGF and VEGF receptor, FLK-1I/KDR. Treatment of diabetic muscles results in a significant improvement of muscle perfusion. Thus IGF-I can be used in a non-viral therapy paradigm to induce angiogenesis, in vivo.

The treatment of injured muscle with IGF-I also induces the muscle differentiation pathway by inducing MyoD and myogenin expression. In a previous study using IGF-I transgenic mice (Rabinovsky et al., 2003) it was shown that IGF-I induces satellite cell activation and differentiation. Recent studies have also shown that nerve injury to IGF-I transgenic mice results in the induction of satellite expression of VEGF. Therefore, the activation of satellite cells by IGF-I results in both induction of muscle cell differentiation as well as angiogenesis, illustrating the multiple effects of IGF-I in its role in the overall wound healing process.

The effect of IGF-I plasmid mediated therapy on both VEGF and VEGF receptor expression suggests that IGF-I can amplify the angiogenic effects of VEGF. Previous in vitro experiments show that IGF-I can induce VEGF receptor FKL-1/KDR protein expression on coronary vessel endothelial cells (Rabinovsky at el., manuscript in preparation). Additionally, it has been shown that IGF-I also up-regulates the angiopoietins, ANG-1 and ANG-2, in an IGF-I transgenic model (Rabinovsky at el., manuscript in preparation). These molecules are critical in the maturation of newly formed vessels. Therefore, the results of in vitro experiments and in vivo transgenic and plasmid mediated therapy studies show that IGF-I acts on diverse targets within the angiogenic pathway.

The functional and physiological role of IGF-I plasmid mediated therapy on inducing angiogenesis has been studied in a diabetic ischemic model. Results showed that IGF-I plasmid mediated therapy can augment angiogenesis in the diabetic ischemic limb. The detrimental effects of diabetes on peripheral blood flow are well documented and the cost to the patient and health care system is high. IGF-I plasmid mediated therapy can have a significant clinical role in improving blood flow in patients with peripheral arterial diseases and diabetic neuropathies and microangiopathies.

The plasmid supplementation approach to induce endogenous IGF-I production determining upregulation of angiogenic factors, such as VEGF, VEGF receptors (FLK-1 and FLT-1), and the angiopoietins (ANG-1 and ANG-2) offers advantages over the limitations of directly injecting recombinant IGF-I or VEGF protein. Expression of novel biological equivalents of IGF-I can be directed by an expression plasmid controlled by a synthetic muscle-specific promoter. Expression of such IGF-I or biological equivalent thereof elicits high IGF-I levels in subjects that have had the encoding sequences delivered into the cells of the subject by intramuscular injection and in vivo electroporation. Electroporation involves placing a plurality of electrodes in a selected tissue, then delivering the nucleic acid expression construct to the selected tissue in an area that interposes the plurality of electrodes, and applying a cell-transfecting pulse (e.g. electrical) to the selected tissue in an area of the selected tissue where the nucleic acid expression construct was delivered. However, the cell-transfecting pulse need not be an electrical pulse. A vascular pressure pulse can also be utilized. Although in vivo electroporation is the preferred method of introducing the heterologous nucleic acid encoding system into the cells of the subject, other methods exist and should be known by a person skilled in the art (e.g. electroporation, lipofectamine, calcium phosphate, ex vivo transformation, direct injection, gene gun, DEAE dextran, sonication loading, receptor mediated transfection, microprojectile or gold particle bombardment, etc.). For example, it may also be possible to introduce the nucleic acid sequence that encodes the IGF-I or functional biological equivalent thereof directly into the cells of the subject by first removing the cells from the body of the subject or donor, maintaining the cells in culture, then introducing the nucleic acid encoding system by a variety of methods (e.g. electroporation, lipofectamine, calcium phosphate, ex vivo transformation, direct injection, DEAE dextran, sonication loading, receptor mediated transfection, microprojectile bombardment, etc.), and finally reintroducing the modified cells into the original subject or other host subject (the ex vivo method). The IGF-I sequence can be cloned into an adenovirus vector or an adeno-associated vector and delivered by simple intramuscular injection, or intravenously or intra-arterially. Plasmid DNA carrying the IGF-I sequence can be complexed with cationic lipids or liposomes and delivered intramuscularly, intravenously or subcutaneous.

Administration as used herein refers to the route of introduction of a vector or carrier of DNA into the body. Administration can be directly to a target tissue or by targeted delivery to the target tissue after systemic administration. In particular, the present invention can be used for treating disease by administration of the vector to the body in order to establish controlled expression of any specific nucleic acid sequence within tissues at certain levels that are useful for plasmid mediated supplementation. The preferred means for administration of vector and use of formulations for delivery are described above.

Muscle cells have the unique ability to take up DNA from the extracellular space after simple injection of DNA particles as a solution, suspension, or colloid into the muscle. Expression of DNA by this method can be sustained for several months. DNA uptake in muscle cells is further enhanced by utilizing in vivo electroporation.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. The characteristics of the complex formed with the vector (size, charge, surface characteristics, composition) determine the bioavailability of the vector within the body. Other elements of the formulation function as ligands that interact with specific receptors on the surface or interior of the cell. Other elements of the formulation function to enhance entry into the cell, release from the endosome, and entry into the nucleus.

Delivery can also be through use of DNA transporters. DNA transporters refer to molecules which bind to DNA vectors and are capable of being taken up by epidermal cells. DNA transporters contain a molecular complex capable of non-covalently binding to DNA and efficiently transporting the DNA through the cell membrane. It is preferable that the transporter also transport the DNA through the nuclear membrane. See, e.g., the following applications all of which (including drawings) are hereby incorporated by reference herein: (1) Woo et al., U.S. Pat. No. 6,150,168 entitled: "A DNA Transporter System and Method of Use;" (2) Woo et al., PCT/US93/02725, entitled "A DNA Transporter System and method of Use", filed Mar. 19, 1993; (3) Woo et al., U.S. Pat. No. 6,177,554 "Nucleic Acid Transporter Systems and Methods of Use;" (4) Szoka et al., U.S. Pat. No. 5,955,365 entitled "Self-Assembling Polynucleotide Delivery System;" and (5) Szoka et al., PCT/US93/03406, entitled "Self-Assembling Polynucleotide Delivery System", filed Apr. 5, 1993.

Another method of delivery involves a DNA transporter system. The DNA transporter system consists of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine. One element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Administration may also involve lipids. The lipids may form liposomes which are hollow spherical vesicles composed of lipids arranged in unilamellar, bilamellar, or multilamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblasts genetically engineered to express recombinant human growth hormone can secrete the growth hormone into the animal's blood. Secretion of the incorporated gene can be sustained over periods up to 3 months.

Myoblasts eventually differentiate and fuse to existing muscle tissue. Because the cell is incorporated into an existing structure, it is not just tolerated but nurtured. Myoblasts can easily be obtained by taking muscle tissue from an individual who needs plasmid-mediated supplementation and the genetically engineered cells can also be easily put back without causing damage to the patient's muscle. Similarly, keratinocytes may be used to delivery genes to tissues. Large numbers of keratinocytes can be generated by cultivation of a small biopsy. The cultures can be prepared as stratified sheets and, when grafted to humans, will generate epidermis which continues to improve in histotypic quality over many years. The keratinocytes are genetically engineered while in culture by transfecting the keratinocytes with the appropriate vector. Although keratinocytes are separated from the circulation by the basement membrane dividing the epidermis from the dermis, human keratinocytes secrete into circulation the protein produced.

Delivery may also involve the use of viral vectors. For example, an adenoviral vector may be constructed by replacing the E1 region of the virus genome with vector elements including a promoter, 5'UTR, 3'UTR and nucleic acid cassette and introducing this recombinant genome into 293 cells which will package this gene into an infectious virus particle. Viruses from this cell may then be used to infect tissue ex vivo or in vivo to introduce the vector into tissues leading to expression of the gene in the nucleic acid cassette.

Although not wanting to be bound by theory, it is believed that in order to provide an acceptable safety margin for the use of such heterologous nucleic acid sequences in humans, a regulated gene expression system must possess low levels of basal expression of IGF-I and still retain a high ability to induce. Thus, target gene expression can be regulated by incorporating molecular switch technology. By combining the powerful electroporation DNA delivery method with regulable IGF-I, or its biological equivalent, encoded by nucleic acid sequences, a therapy can be utilized that will enhance IGF-I production, and as a consequence enhance angiogenesis.

I. Vectors

The term "vector" is used to refer to a carrier nucleic acid molecule into which a nucleic acid sequence can be inserted for introduction into a cell wherein, in some embodiments, it can be replicated. A nucleic acid sequence can be native to the animal, or it can be "exogenous," which means that it is foreign to the cell into which the vector is being introduced or homologous to a sequence in the cell but in a position within the host cell nucleic acid in which the sequence is ordinarily not found. Vectors include plasmids, cosmids, viruses (bacteriophage, animal viruses, and plant viruses), linear DNA fragments, and artificial chromosomes (e.g., YACs), although in a preferred embodiment the vector contains substantially no viral sequences. One of skill in the art would be well equipped to construct a vector through standard recombinant techniques.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possible translation of an operatively linked coding sequence in a particular host cell. In addition to control sequences that govern transcription and translation, vectors and expression vectors may contain nucleic acid sequences that serve other functions as well and are described infra.

II. Plasmid Vectors

In certain embodiments, a linear DNA fragment from a plasmid vector is contemplated for use to transfect a eukaryotic cell, particularly a mammalian cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. The plasmid pBR322 contains genes for ampicillin and tetracycline resistance and thus provides easy means for identifying transformed cells. The pBR plasmid, or other microbial plasmid or phage, must also contain or be modified to contain, for example, promoters which can be used by the microbial organism for expression of its own proteins. A skilled artisan recognizes that any plasmid in the art may be modified for use in the methods of the present invention. In a specific embodiment, for example, a GHRH vector used for the therapeutic applications is derived from pBlueScript KS+ and has a kanamycin resistance gene.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S-transferase ("GST") soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally between 2 and 24 hours, the cells are collected by centrifugation and washed to remove residual media.

III. Promoters and Enhancers

A promoter is a control sequence that is a region of a nucleic acid sequence at which initiation and rate of transcription of a gene product are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant, synthetic or heterologous promoter, which refers to a promoter that is not normally associated with a nucleic acid sequence in its natural environment. A recombinant, synthetic or heterologous enhancer refers also to an enhancer not normally associated with a nucleic acid sequence in its natural environment. Such promoters or enhancers may include promoters or enhancers of other genes, promoters or enhancers isolated from any other virus or prokaryotic or eukaryotic cell, and promoters or enhancers not "naturally occurring," i.e., containing different elements of different transcriptional regulatory regions and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 1 and 2 list non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

| Promoter and/or Enhancer | |
|---|---|
| Promoter/Enhancer | Relevant References |
| β-Actin | (Kawamoto et al., 1988; Kawamoto et al., 1989) |
| Muscle Creatine Kinase (MCK) | (Horlick and Benfield, 1989; Jaynes et al., 1988) |
| Metallothionein (MTII) | (Inouye et al., 1994; Narum et al., 2001; Skroch et al., 1993) |
| Albumin | (Pinkert et al., 1987; Tronche et al., 1989) |
| β-Globin | (Tronche et al., 1990; Trudel and Costantini, 1987) |
| Insulin | (German et al., 1995; Ohlsson et al., 1991) |
| Rat Growth Hormone | (Larsen et al., 1986) |
| Troponin I (TN I) | (Lin et al., 1991; Yutzey and Konieczny, 1992) |
| Platelet-Derived Growth Factor (PDGF) | (Pech et al., 1989) |
| Duchenne Muscular Dystrophy | (Klamut et al., 1990; Klamut et al., 1996) |
| Cytomegalovirus (CMV) | (Boshart et al., 1985; Dorsch-Hasler et al., 1985) |
| Synthetic muscle specific promoters (c5-12, c1-28) | (Draghia-Akli et al., 1999; Draghia-Akli et al., 2002; Li et al., 1999) |

TABLE 2

| Element/Inducer | |
|---|---|
| Element | Inducer |
| MT II | Phorbol Ester (TFA) |
| | Heavy metals |
| MMTV (mouse mammary tumor virus) | Glucocorticoids |
| β-Interferon | Poly(rI)x/Poly(rc) |
| Adenovirus 5 E2 | E1A |
| Collagenase | Phorbol Ester (TPA) |
| Stromelysin | Phorbol Ester (TPA) |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2κb | Interferon |
| HSP70 | E1A, SV40 Large T Antigen |
| Proliferin | Phorbol Ester-TPA |
| Tumor Necrosis Factor α | PMA |
| Thyroid Stimulating Hormone α Gene | Thyroid Hormone |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Liu et al., 2000; Tsumaki et al., 1998), DIA dopamine receptor gene (Lee et al., 1997), insulin-like growth factor II (Dai et al., 2001; Wu et al., 1997), and human platelet endothelial cell adhesion molecule-1 (Almendro et al., 1996).

In a preferred embodiment, a synthetic muscle promoter is utilized, such as SPc5-12 (SEQ ID NO.: 3) (Li et al., 1999), which contains a proximal serum response element ("SRE") from skeletal α-actin, multiple MEF-2 sites, MEF-1 sites, and TEF-1 binding sites, and greatly exceeds the transcriptional potencies of natural myogenic promoters. The uniqueness of such a synthetic promoter is a significant improvement over, for instance, issued patents concerning a myogenic promoter and its use (e.g. U.S. Pat. No. 5,374,544) or systems for myogenic expression of a nucleic acid sequence (e.g. U.S. Pat. No. 5,298,422). In a preferred embodiment, the promoter utilized in the invention does not get shut off or reduced in activity significantly by endogenous cellular machinery or factors. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information ("NCBI") GenBank database or the NCBI PubMed site. A skilled artisan is aware that these databases may be utilized to obtain sequences or relevant literature related to the present invention. Because changes can be made to specific promoters, such as modifications to binding sites and enhancers, a preferred myogenic promoter comprises a nucleic acid sequence that is at least 85% identical to SEQ ID NO.: 3.

IV. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry site ("IRES") elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picomavirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. An example ribosomal binding site is illustrated in SEQ ID NO.: 8. Multiple genes can be efficiently expressed using a single promoter/enhancer to transcribe a single message (see U.S. Pat. Nos. 5,925,565 and 5,935,819, each herein incorporated by reference).

V. Multiple Cloning Sites

Vectors can include a MCS, which is a nucleic acid region that contains multiple restriction enzyme sites, any of which can be used in conjunction with standard recombinant technology to digest the vector (see, for example, (Carbonelli et al., 1999; Cocea, 1997; Levenson et al., 1998) incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

VI. Restriction Enzymes

In some embodiments of the present invention, a linear DNA fragment is generated by restriction enzyme digestion of a parent DNA molecule. The term "restriction enzyme digestion" of DNA as used herein refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Restriction enzymes are used to ensure plasmid integrity and correctness.

VII. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

VIII. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues ("polyA") to the 3' end of the transcript. RNA molecules modified with this polyA tail appear to be more stable and are translated more efficiently.

Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to the termination sequences of genes, such as the bovine growth hormone terminator, or viral termination sequences, such as the SV40 terminator. In certain embodiments, the termination signal may be a lack of transcribable or translatable sequence, such as due to a sequence truncation.

IX. Polyadenylation Signals

In expression, particularly eukaryotic expression, one will typically include a polyadenylation signal to effect proper polyadenylation of the transcript (e.g. SEQ ID NO.: 5, or SEQ ID NO.: 6). The nature of the polyadenylation signal is not believed to be crucial to the successful practice of the invention, and any such sequence may be employed. Preferred embodiments include the SV40 polyadenylation signal, skeletal alpha actin 3'UTR or the human or bovine growth hormone polyadenylation signal, which is convenient and known to function well in various target cells. Other embodiments include the 3'UTR having a nucleic acid sequence that is at least 85% identical to SEQ ID NO.: 5 from a skeletal alpha actin gene, or at least 85% identical to SEQ ID NO.: 6 from a human growth hormone gene. Polyadenylation may increase the stability of the transcript or may facilitate cytoplasmic transport.

X. Origins of Replication

In order to propagate a vector in a host cell, it may contain one or more origins of replication sites (often termed "ori"), which is a specific nucleic acid sequence at which replication is initiated (e.g. SEQ ID NO.: 8). Alternatively, an autonomously replicating sequence ("ARS") can be employed if the host cell is yeast.

XI. Selectable and Screenable Markers

In certain embodiments of the invention, cells containing a nucleic acid construct of the present invention may be identified in vitro or in vivo by including a marker in the expression vector. Such markers confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants. For example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers, including screenable markers such as GFP, whose basis is calorimetric analysis, are also contemplated. Alternatively, screenable enzymes such as herpes simplex virus thymidine kinase ("tk") or chloramphenicol acetyltransferase ("CAT") may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

XII. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding and other methods known in the art.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules, after the cells have been exposed to electric pulses. There are conduits through cell walls which under normal circumstances maintain a resting transmembrane potential of ca. 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes, are imposed on them. The protocols used for electroporation are defined in terms of the resulting field intensities, according to the formula $E=V/d$, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes, because the flow of ions is not necessary to create an electric field. Although not wanting to be bound by theory, it is the current that is necessary for successful electroporation, not electric field per se.

During electroporation, the heat produced is the product of the inter-electrode impedance, the square of the current, and the pulse duration. Heat is produced during electroporation in tissues and can be derived as the product of the inter-electrode current, voltage and pulse duration. The protocols currently described for electroporation are defined in terms of the resulting field intensity E, which is dependent on short voltage pulses of unknown current. Accordingly, the resistance or heat generated in a tissue cannot be determined, which leads to varied success with different pulsed voltage electroporation protocols with predetermined voltages. Although not wanting to be bound by theory, the nature of the voltage pulse to be generated is determined by the nature of the tissue, the size of the selected tissue, and the distance between electrodes. It is desirable that the voltage pulse be as homogenous as possible and of the correct amplitude. Excessive field strength results in the lysing of cells, whereas a low field strength results in reduced efficacy of electroporation. Some electroporation devices utilize the distance between electrodes to calculate the electric field strength and predetermined voltage pulses for electroporation. This reliance on knowing the distance between electrodes is a limitation to the design of electrodes. Because the programmable current pulse controller will determine the impedance in a volume of tissue between two electrodes, the distance between electrodes is not a critical factor for determining the appropriate electrical current pulse. Therefore, an alternate needle electrode array design would be one that is non-symmetrical. In addition, one skilled in the art can imagine any number of suitable symmetrical and non-symmetrical needle electrode arrays. The depth of each individual electrode within an array and in the desired tissue could be varied with comparable results. In addition, multiple injection sites for the macromolecules could be added to the needle electrode array.

The ability to limit heating of cells across electrodes can increase the effectiveness of any given electroporation voltage pulsing protocol. For example, the prior art teaches an array of six needle electrodes utilizing a predetermined voltage pulse across opposing electrode pairs. This situation sets up a centralized pattern during an electroporation event in an area where congruent and intersecting overlap points develop. Excessive heating of cells and tissue along the electroporation path will kill the cells and limit the effectiveness of the protocol. However, symmetrically arranged needle electrodes without opposing pairs can produce a decentralized pattern during an electroporation event in an area where no congruent electroporation overlap points can develop. It is preferable to use an electrode system for electroporation havin a configuration of pin electrodes whereby the electroporation pulse is directed between two or more electrodes such that the direct line between any two electrodes does not pass through the center of the injected macromolecule. This is to minimize the number of cells that are under energized and thus not electroporated and the number of cells which are over energized and thus destroyed while at the same time maximizing the number of cells that lie between these extremes which are adequately energized and thus electroporated.

Controlling the current flow between electrodes allows one to determine the relative heating of cells. Thus, it is the current that determines the subsequent effectiveness of any given pulsing protocol and not the voltage across the electrodes. Predetermined voltages do not produce predetermined currents, and the usefulness of the technique is limited without a means to determine the exact dosage of current. This problem may be overcome by using a constant-current system, which effectively controls the dosage of electricity delivered to the cells in the inter-electrode space by precisely controlling the ionic flux that impinges on the conduits in the cell membranes. The advantage of a constant-current system is that it can be prevented from attaining an amplitude at which the cells are destroyed. In a predetermined voltage system, the current can attain a destructive intensity, and the operator cannot prevent that from happening. In a constant-current system, the current is preset under a threshold level where cell death does not occur. The exact setting of the current is dependent on the electrode configuration, and it must be determined experimentally. However, once the proper level has been determined, cell survival is assured from case to case. The precise dosage of electricity to tissues can be calculated as the product of the current level, the pulse length and the number of pulses delivered. These factors can be determined by the operator and do not vary with the characteristics of different tissues or variations of the electrode impedance from case to case. Thus, controlling and maintaining the current in the tissue between two electrodes under a threshold will allow one to vary the pulse conditions, reduce cell heating, create less cell death, and incorporate macromolecules into cells more efficiently when compared to predetermined voltage pulses. Furthermore, owing to the inherent repeatability of the constant-current system, effective protocols for electroporation can be developed.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Construction Of DNA Vectors

Figure 2:
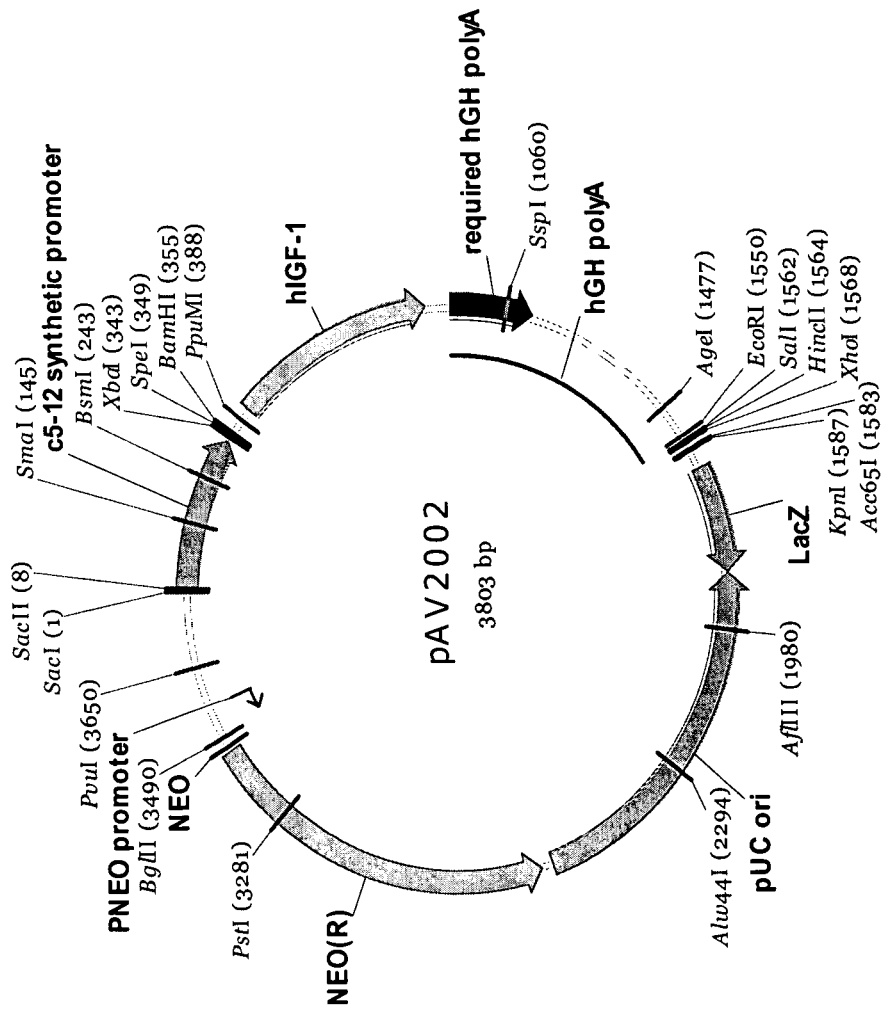
FIG. 2 illustrates the vector pAV2002 (SEQ ID NO.: 2), or pSP-IGF-I-GH3'UTR, which includes the 3'UTR of human growth hormone.

In order to determine endogenous IGF-I production by the skeletal muscle cells it was first necessary to design several IGF-I constructs. Briefly, the plasmid vectors contained the muscle specific synthetic promoter SPc5-12 (SEQ ID NO.: 3) (Li et al., 1999) attached to a IGF-I cDNA fragment. Although the SPc5-12 promoter was utilized in this specific embodiment of this invention, other myogenic promoters are equally useful as expression control sequences. An NcoI/HindIII fragment of a SIS II plasmid (Coleman et al., 1995), containing the IGF-I cDNA and the skeletal alpha actin 3'UTR, was cloned into the NcoI/KpnI sites of pSP-HV-GHRH (Draghia-Akli et al., 1999) to generate pSP-IGF-I-SK3'UTR (pAV2001-SEQ ID NO.: 1). This vector, pAV2001 (SEQ ID NO.: 1), is shown in FIG. 1, and preferred embodiments include nucleic acid sequences that are at least 90% identical to SEQ ID NO. 1. To generate pSP-IGF-I-GH3'UTR (pAV2002-SEQ ID NO.: 2), the NcoI/BamHI blunt fragment was cloned in between the NcoI/HindIII blunt sites of pSP-HV-GHRH. This vector, pAV2002 (SEQ ID NO.: 2), is shown in FIG. 2, and preferred embodiments include nucleic acid sequences that are at least 90% identical to SEQ ID NO. 2. Although not wanting to be bound by theory, the stimulation of angiogenesis and myogenesis are determined ultimately by the levels of hormones in the general circulation and/or locally in the muscle fiber. Several different plasmids that encoded amino acid sequences of IGF-I (SEQ ID NO.: 4) with different promoters and 3'ends or functional biological equivalent thereof were used in these experiments.

The pSP plasmids described and used above do not contain polylinker or a skeletal alpha-actin promoter. Furthermore, these plasmids were introduced by muscle injection, followed by in vivo electroporation, as described below.

In terms of "functional biological equivalents", it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Functional biological equivalents are thus defined herein as those proteins (and polynucleotides) in which selected amino acids (or codons)

may be substituted. A peptide comprising a functional biological equivalent of IGF-I (SEQ ID NO.: 4) is a polypeptide that is engineered to contain distinct amino acid sequences while simultaneously having similar or improved biological activity when compared to IGF-I (SEQ ID NO.: 4). Thus, in one embodiment of the encoded IGF-I or functional biological equivalent thereof has an amino acid sequence of SEQ ID NO: 4, or SEQ ID NO.: 4 with conservative amino acid substitutions. In another embodiment, a preferred IGF-I peptide comprises an amino acid sequence that is at least 85% identical to SEQ ID NO.: 4, wherein the biological activity is preserved or enhance. For example, one biological activity of IGF-I is to stimulate angiogenesis in a subject.

Constructs were compared in vivo in animal experiments to establish the level of expression and functionality.

EXAMPLE 2

Material and Methods for Animal Studies

Figure 3:
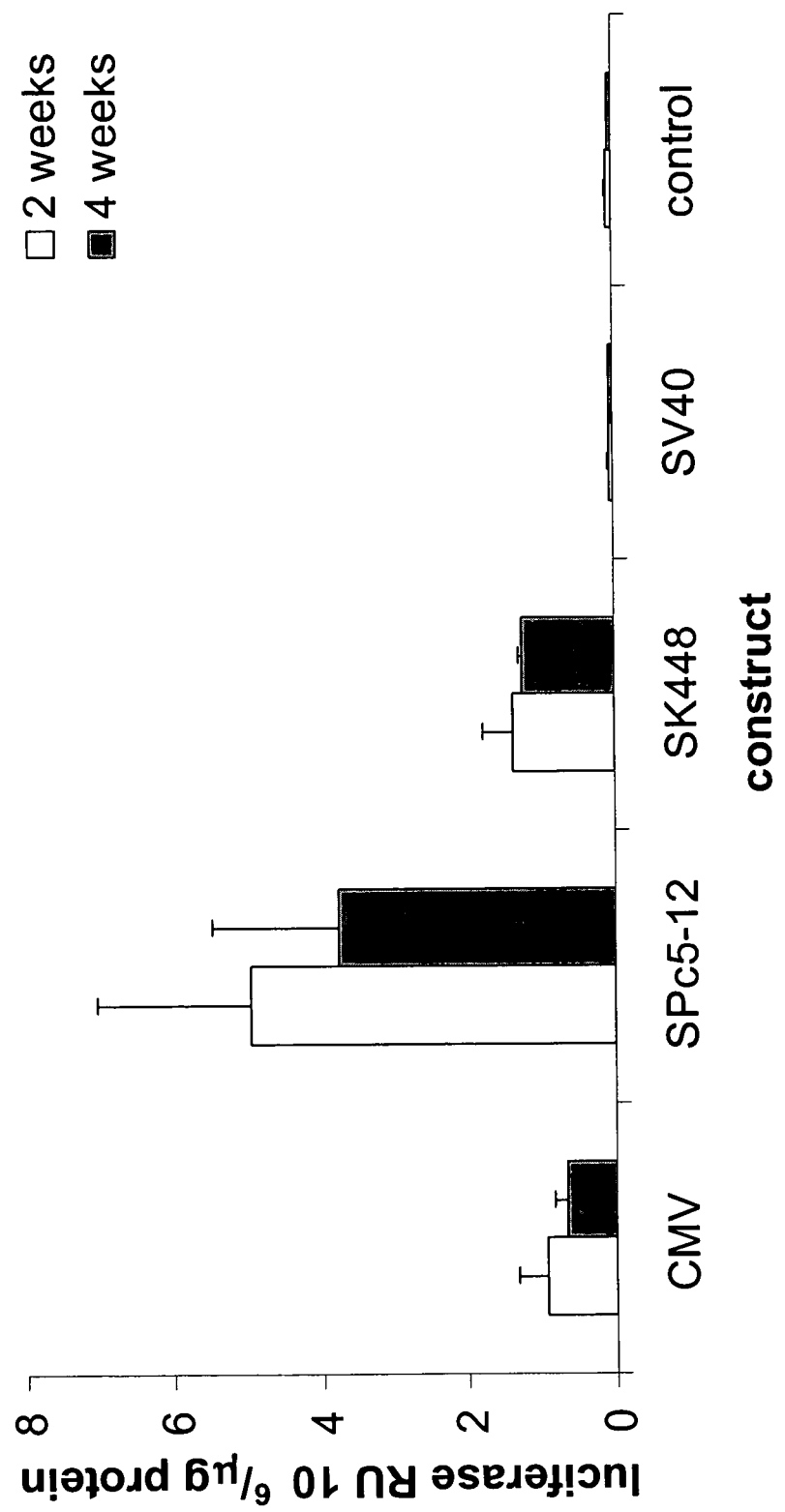
FIG. 3 shows the in vivo expression and activity of synthetic promoter SPc5-12 (SEQ ID NO.: 3).

Intramuscular injection of plasmid DNA in adult mice. In vivo activity of the synthetic promoter SPc5-12 (SEQ ID NO.: 3) was compared with the activity of the skeletal alpha actin promoter (natural muscle specific promoter), cytomegalovirus promoter (strong ubiquitous promoter), and the simian virus 40 (SV40) promoter. Plasmid preparations of SPc5-12, SK448, CMV and SV40-luciferase were diluted in PBS pH=7.4 to 1 mg/ml. ICR male mice (Harlem Laboratories, TX) were anesthetized with 0.5 ml/kg of a combination of ketamine (42.8 mg/ml), xylazine (8.2 mg/ml) and acepromazine (0.7 mg/ml). Fifty micrograms of plasmid in 25 µl sterile PBS was injected directly into the anterior tibialis of mice. At 1, 2 and 4 weeks after the injection, the injected muscle was snap frozen in liquid nitrogen. Muscles were homogenized in PBS, pH=7.4 containing 0.2% Triton x-100 and protease inhibitors: leupeptin, 0.7 µg/ml, pepstatin 10 µg/ml and aprotinin 2 µg/ml (Boehringer Mannheim, Indianapolis, Ind.). Muscle extracts were centrifuged at 10,000×g for 30 minutes at 4° C. and the supernatant recovered. Protein assays were performed using Bio-Rad Protein Assay (Bio-Rad Laboratories, Hercules, Calif.) and luciferase activity was measured. At each time point, 6-15 animals were used for each construct. The experiments were repeated twice. Results are shown in FIG. 3. At 2 and 4 weeks after direct intramuscular injection the SPc5-12 (SEQ ID NO.: 3) promoter had a 3-5 fold higher expression than that of the SK448 promoter and 6-8 times greater than that of the CMV promoter. The SV40 promoter was 100 fold less active (n≧8 animals/construct).

The plasmid can also be formulated prior to injection with an effective concentration of transfection-facilitating polypeptide in order to increase plasmid stability and diminish muscle damage that may occur during the electroporation procedure. The transfection-facilitating polypeptide is preferably charged and is most preferably poly-L-glutamate ("PLG"). The ratio in moles of the transfection-facilitating polypeptide to the nucleic acid expression construct should be 1,200 moles or less, and more preferably 1 mole, of transfection-facilitating polypeptide per mole of the nucleic acid expression construct. The average molecular weight of the transfection-facilitating polypeptide should be about 400 to about 30,000 Da, more preferably about 10,900 Da. In a previous study (Draghia-Akli et al., 2002a), it was shown that although naked plasmid showed some expression, all groups with the nucleic acid expression vector associated with PLG showed significantly higher serum levels of transgene product ($p<0.05$). When muscle samples from animals from each group were analyzed histologically, mice that received the plasmid construct coated with 0.01 mg/mL PLG had the least inflammation associated with the delivery procedure.

Figure 4:
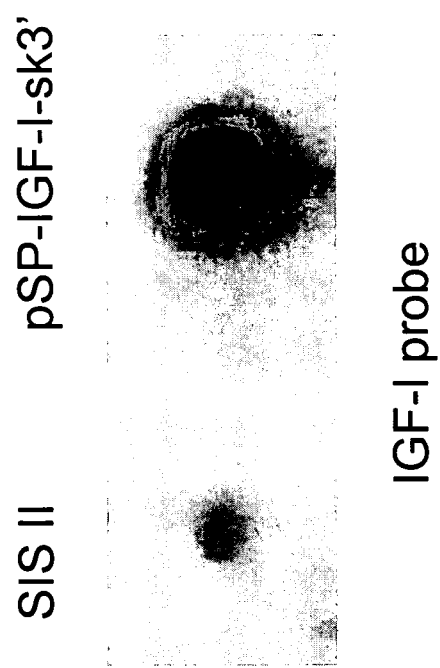
FIG. 4 shows a Northern blot analysis of IGF-I expression.

Northern blot analysis. Three weeks after injection of 5 µg of either SIS II construct or pSP-IGF-I-SK3'UTR (pAV2001-SEQ ID NO.: 1) construct into tibialis anterior muscle of adult mice, the mice were killed, injected muscles were snap frozen, and RNA was collected and run in a Northern blot assay. 10-20 µg of total RNA was DNase I treated (Gibco BRL), size separated in 1.5% agarose-formaldehyde gel and transferred to Gene Screen nylon membrane (DuPont Research Products, Boston, Mass.). The membranes were hybridized with IGF-I cDNA probes P labeled by random priming (Ready-to-Go DNA labeling kit, Pharmacia Biotech, Piscataway, N.J.). Hybridization was carried out at 45° C. in a solution which contained 50% formamide, 5×SSPE, 5xDenhardts, 1% SDS, 200 µg/ml sheared salmon sperm DNA. Membranes were washed twice for 10 minutes in 2×SSPE/1% SDS at room temperature and twice for 30 minutes in 0.2×SSPE/1% SDS at 68° C. Blots were subsequently exposed to X-ray film (Kodak X-Omat AR; Eastman Kodak, Rochester, N.Y.) at −80° C. with intensifying screens. As shown in FIG. 4, the construct pSP-IGF-I-SK3'UTR (pAV2001-SEQ ID NO.: 1) driven by the muscle specific SPc5-12 (SEQ ID NO.: 3) promoter had a 10-fold higher expression in the injected muscle comopared to SIS II construct.

The Diabetic Model. Female ICR mice were used in this study. To induce diabetes, mice were treated with streptozotocin ("STZ"), administered intraperitoneally five consecutive days at 55 mg/kg/day. Typically, approximately 80% of the animals became diabetic (glucose>300 mg/dL). Those animals not reaching this level were excluded from the study.

Nerve Injury Paradigm. Mice were anesthetized with Avertin (0.2 mL/10 g body weight, injected intra-peritoneally in a 1.25% solution). To induce nerve crush injury, sciatic nerve exposed mid-thigh was crushed 2 mm distal to the sciatic notch with Dumonts #5 forceps for 30 seconds. The wound was closed with sterile clips and the mice were placed on a warming pad for 1 hour or until the animals awoke. The contralateral side, left intact, was used as a control.

Femoral Artery/Vein Ligation. To test the ability of pSP-IGF-I-SK3'UTR (pAV2001-SEQ ID NO.: 1) to enhance angiogenesis in the diabetic state, a femoral artery ligation/angiogenesis assay was performed. ICR female mice were made diabetic by STZ injections as described. The mice were kept in the diabetic state for 2 months. The mice were anesthetized with Avertin (0.2 mL/10 g body weight, injected intra-peritoneally in a 1.25% solution) and the femoral artery and vein were exposed. The femoral artery and vein were ligated with 6-0 silk suture at the femoral ligament and just proximal to the epigastric vein and artery. The vessel was then cauterized between the two ligatures. The femoral nerve was kept intact in all procedures. The wound was closed with 6-0 silk sutures. After ligation, groups of mice were either injected in the tibialis anterior muscle of the ligated side with 120 µg pSP-IGF-I-SK3'UTR (pAV2001-SEQ ID NO.: 1) or distilled water. After 2 weeks, the muscle was analyzed for real time flow by Doppler Perfusion imaging, described below.

Dopper Analysis. A Doppler perfusion imager (LDI-2 Laser Doppler Imager; Moor Instruments, Wilmington, Del.) was employed to determine real time flow after femoral ligation in diabetic animals. An initial Doppler image was performed 24 hours after the femoral ligation to determine that flow to the tibialis anterior muscle was decreased. After 2 weeks post ligation, animals were anesthetized as described and Doppler imaging was performed. Tibialis anterior muscle from the ligated and non-ligated sides was imaged simultaneously to avoid differences in muscle temperature and moisture between animals. These parameters affect flow rates.

Chemiluminescence Enzyme-linked Immunosorbant Assay ("CELISA"). Muscle was homogenized in RIPA buffer (1×PBS, 1% NP-40, 0.5% sodium deoxycholate, 0.1% SDS) with a complete protease inhibitor cocktail (Roche, Indianapolis, Ind.), and protein was assayed using BCA reagent (Pierce, Rockford, Ill.). To prepare 96-well ELISA plates (Ninc Maxicoat, Nalge Nunc International, Rochester, N.Y.), wells were coated with 50 µl of nitrocellulose (HAFT Membranes, Millipore, Bedford, Mass.) which was solubilized for 2 hours in methanol and centrifuged at 5000×g. Wells were treated for 15 minutes at room temperature, the solution was removed and the wells were allowed to dry. The wells were coated with 50 µl of protein samples, diluted to 0.1 mg/mL in distilled $H_2O$, and allowed to dry overnight in a laminar flow hood, then washed twice in PBS. Anti-mouse monoclonal antibodies myogenin, MyoD F5D, (DAKO Corporation, Carpinteria, Calif.), VEGF (Santa Cruz, Calif.) and FLK-1 (Santa Cruz, Calif.), were biotinylated using a DAKO ARK kit (Dako Corporation, Carpinteria, Calif.) according to the manufacturers instructions. Rabbit Polyclonal antibody FLT-1 (Santa Cruz, Calif.) was also employed. Incubations were performed overnight at 4° C. at antibody concentrations of 1.25-5.00 µg/mL in 50 µl volumes. Plates were washed 3 times for 15 minutes each in PBS/Tween (0.1%). For FLT-1, plates were treated with biotinylated goat anti-rabbit IgG (1 µg/mL; Jackson ImmunoResearch) and incubated for 1 hour at room temperature. After washing, all wells were then incubated with 1 µg/mL streptavidin-peroxidase (Jackson ImmunoResearch) for 1 hour at room temperature. After washing, ECL chemiluminescence reagent (Amersham) was diluted 1:2 in PBS and 50 µL was added to the wells and luminescence was quantified on a Perkin Elmer HTS 7000 Plus Bioassay reader with HT 2.0 software using an integration time of 500 msec and a gain of 100.

Immunohistochemistry. Tibialis anterior muscle was fixed in 4% paraformaldehyde for 2 hours, then switched to 20% sucrose/PBS and incubated overnight. The tissue was embedded in OCT resin, and tissues were cut to 7-10 microns in a cryostat. Sections were quenched by a 10 minute incubation with 3% peroxide in PBS, pH 7.4. After 3 washes, sections were incubated overnight at 4° C. with either 2.5 µg/mL of biotinylated monoclonal antibody to VEGF and FLK-1 or polyclonal antibody FLT-1, diluted in PBS. After washing, sections were reacted with 2 µg/mL of biotinylated goat anti-rabbit IgG for 1 hour at room temperature. After washing, all sections were treated with 2 µg/mL streptavidin-HRP for 1 hour at room temperature. After washing 3 times in PBS, sections were reacted with diaminobenzidine chromogen/$H_2O_2$ for 5-30 minutes, and then washed in distilled $H_2O$. Mounting media (Shandon Immu-Mount; Shandon, Pittsburgh, Pa.) was applied and the sections were cover-slipped.

Statistical Analysis. For CELISA analysis, replicate samples for each group were assayed in quadruplicate. The values are expressed as percent control of water treated non-injured muscle (defined as 100%). The percent values were averaged and the data is presented as the mean+/−SEM (n=3/group). Comparisons between experimental groups were analyzed by non-paired one tailed Student's t-test. P values less than 0.05 were designed as statistically significant. In all studies, three separate experiments were performed.

One skilled in the art readily appreciates that the present invention is well adapted to carry out the objectives and obtain the ends and advantages mentioned as well as those inherent therein. IGF-I, analogs, plasmids, vectors, pharmaceutical compositions, treatments, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

EXAMPLE 3

Localization of IGF-I and its Consequences

Initial experiments were done to assess the expression of IGF-I expressed by different muscle-specific plasmid constructs. The plasmids pSP-IGF-I-SK3'UTR (pAV2001-SEQ ID NO.: 1) and pSP-IGF-I-GH3'UTR (pAV2002-SEQ ID NO.: 2) were compared in vivo with the SIS II and SIG constructs previously described (see U.S. Pat. Nos. 5,298,422; 5,756,264; and 5,925,564). Expression from the new constructs was 3-5 fold higher than the previously described constructs. Furthermore, the localization of the IGF-I (SEQ ID NO.: 4) product was important for differential local effects.

Figure 5:
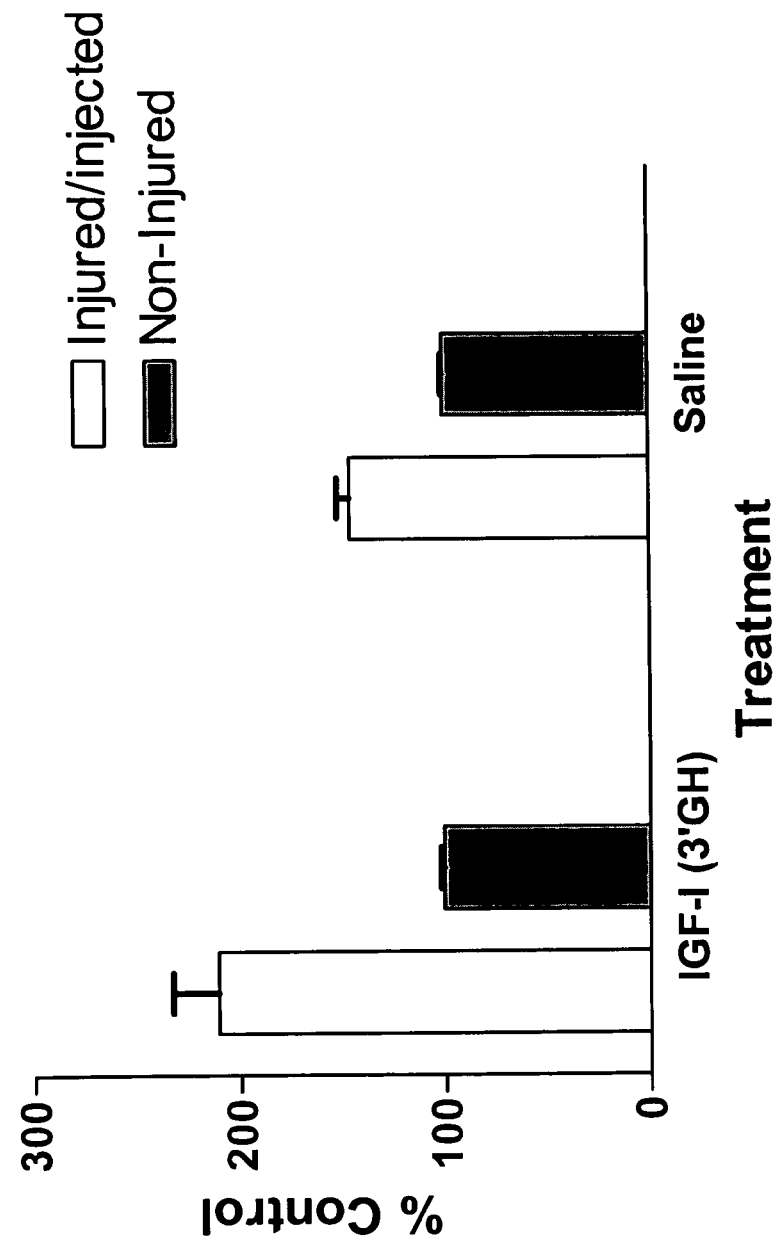
FIG. 5 shows expression of FLK-1/KDR as a result of injection of the pSP-IGF-I-GH3'UTR (pAV2002-SEQ ID NO.: 2) construct. Data are presented as the percent control of contralateral non-injured muscle from IGF-I and water injected mice.

Localization of IGF-I Product. FLK-1 is a high-affinity tyrosine receptor for VEGF signaling pathways that induces endothelial cell proliferation and migration. Experiments were done to determine the effects of IGF-I plasmid mediated supplementation using a construct that stimulates the secretion of the transgene product into the general circulation on FLK-1 expression after a nerve injury. The sciatic nerve of ICR-I female mice was crushed mid thigh. Afterwards, 120 µg of pSP-IGF-I-GH3'UTR (pAV2002-SEQ ID No.: 2) diluted in distilled water was injected in the tibialis anterior in a volume of 30 µl. The muscle was then electroporated at 220V/cm, 20 msec, and 3 pulses, positive and reverse polarity, each. In control mice, 30 µl of distilled water was injected into injured muscle and electroporated as above. After 3 days, the muscle of IGF-I and water-injected mice was analyzed with CELISA. The results shown in FIG. 5 indicate that IGF-I plasmid mediated supplementation using a construct that stimulates the secretion of the transgene product into the general circulation enhances at a low level the expression of FLK-1/KDR in skeletal muscle.

Figure 6:
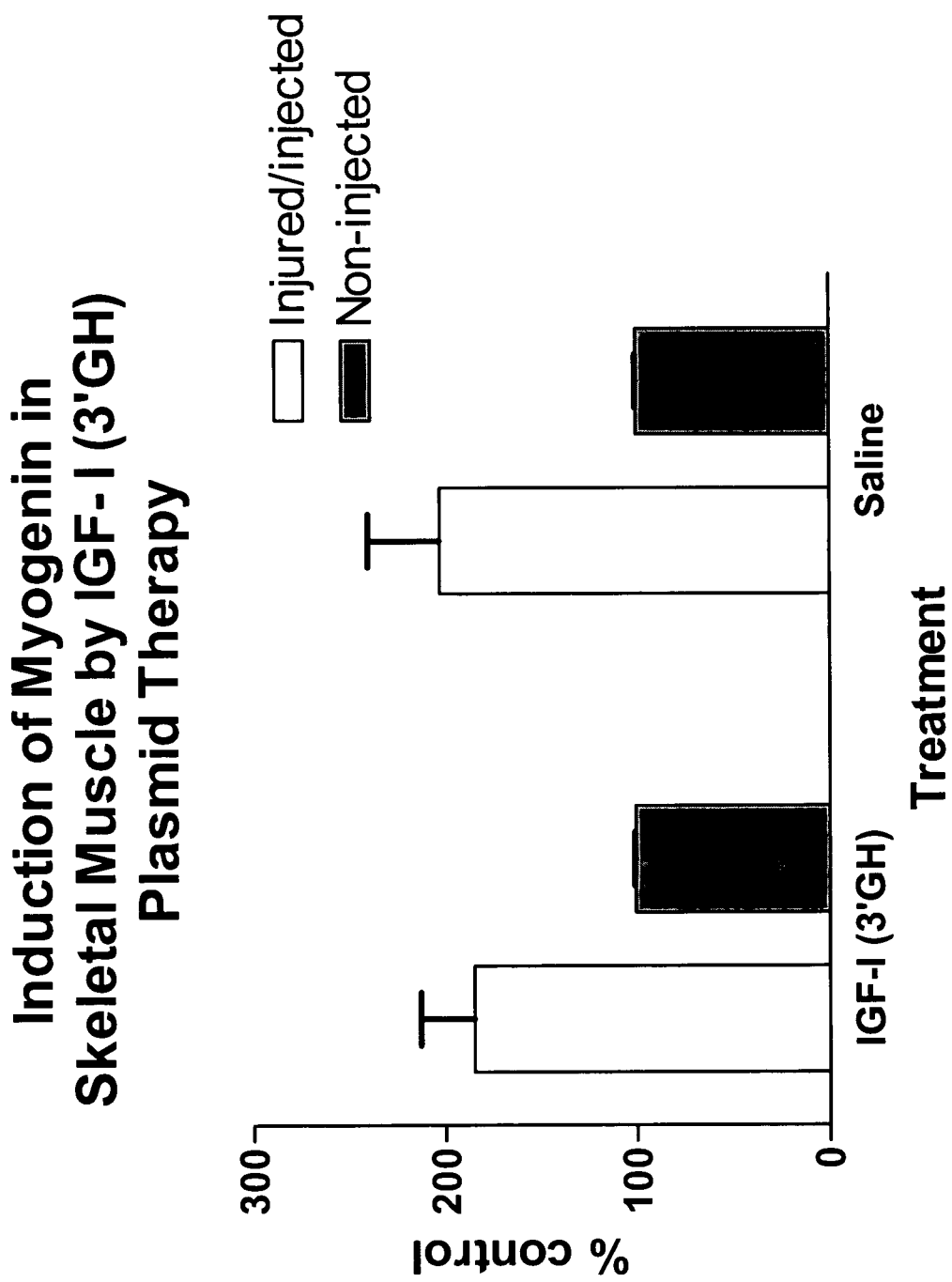
FIG. 6 shows expression of myogenin as a result of injection of the pSP-IGF-I-GH3'UTR (pAV2002-SEQ ID NO.: 2) construct. Data is presented as the percent control of contralateral non-injured muscle from IGF-I and water injected mice.

Additional experiments were done to determine the effects of IGF-I plasmid mediated supplementation using a construct that stimulates the secretion of the transgene product into the general circulation myogenin expression after a nerve injury. The sciatic nerve of ICR-I female mice was crushed mid thigh. Afterwards, 120µg of pSP-IGF-I-GH3'UTR (pAV2002- SEQID No.: 2), diluted in distilled water was injected in the tibialis anterior in a volume of 30µl. The muscle was then electroporated at 220V/cm, 20 msec, and 3 pulses, positive and reverse polarity, each. In control mice, 30µl of distilled water was injected into injured muscle and electroporated as above. After 3 days, the muscle of IGF-I and water-injected mice was analyzed with CELISA. The results shown in FIG. 6 indicate that IGF-I plasmid mediated supplementation using a construct that stimulates the secretion of the transgene product into the general circulation does not affect myogenin expression in the treated muscle.

While IGF-I secreted from the muscle fibers (with the pSP-IGF-I-GH3'UTR (pAV2002-SEQ ID NO.: 2) construct) determined stimulation of angiogenesis only, increased intracellular IGF-I in the muscle fibers (with the pSP-IGF-I-SK3'UTR (pAV2001-SEQ ID NO.: 1) construct) determined stimulation of both angiogenesis and myogenesis. As both angiogenesis and myogenesis are needed post-trauma, further experiments were conducted using the pSP-IGF-I-SK3'UTR (pAV2001-SEQ ID NO.: 1) plasmid construct.

Figure 7:
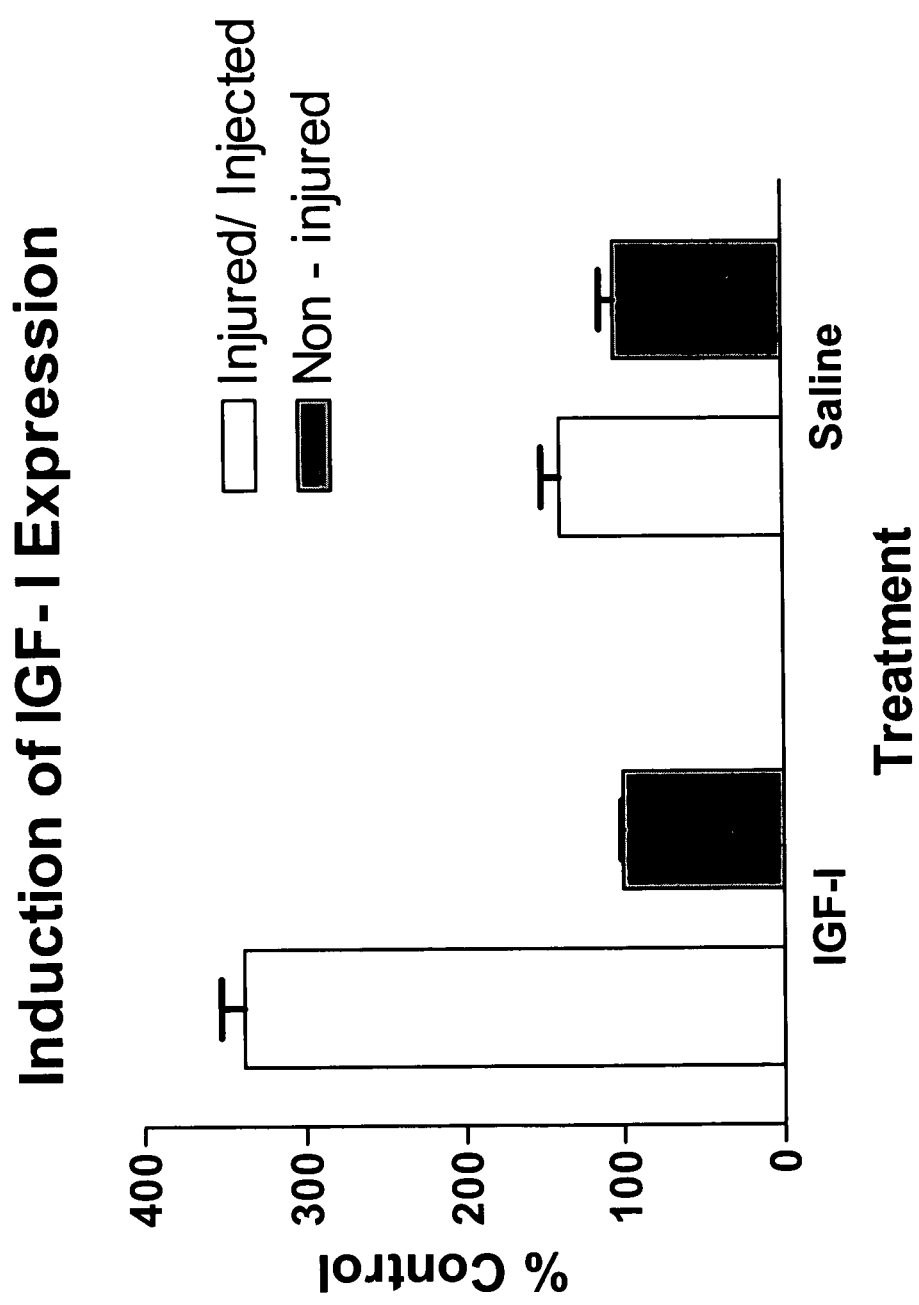
FIG. 7 shows the induction of IGF-I expression in the tibialis anterior muscle of mice after IGF-I gene injection. Data is presented as the percent of control contralateral non-injured muscle from IGF-I and water injected mice. *$P<0.05$ in IGF-I injected vs. water injected muscle (n=3/group).

Induction of IGF-I expression in injured tibialis anterior muscle after IGF-I gene injection. The sciatic nerve of ICR-I female mice was crushed mid thigh. Afterwards, 120 µg of pSP-IGF-I-SK3'UTR (pAV2001-SEQ ID NO.: 1) diluted in distilled water was injected in the tibialis anterior muscle in a volume of 30 µl. The muscle was then electroporated using conditions of at 220V/cm, 20 msec, and 3 pulses (positive and reverse polarity, each). In control mice, 30 µl of distilled water was injected into the injured muscle and electroporated as above. After 3 days, mice treated with IGF-I and water-injected mice were analyzed with CELISA. As shown in FIG. 7, water-injected muscle showed a 0.35 fold increase in IGF-I expression, compared to non-injured muscle. This increase is a normal response to nerve injury that initiates muscle and nerve regeneration. In contrast, muscle injected with pSP-IGF-I-SK3'UTR (pAV2001-SEQ ID NO.: 1) plasmid resulted in a 2.5-fold increase in IGF-I expression, compared to water-injected muscle. These results show that IGF-I plasmid mediated supplementation results in a significant increase in IGF-I protein over controls.

EXAMPLE 4

IGF-I Induces Angiogenesis and Myogenesis in the Damaged Muscle

The induction of muscle differentiation and angiogenesis are linked through the differentiation of muscle stem (satellite) cells following an injury (Lescaudron et al., 1999). The muscles of IGF-I transgenic mice were previously shown to undergo enhanced satellite cell proliferation and differentiation after a nerve injury (Rabinovsky et al., 2003). MyoD and myogenin are muscle regulatory factors that have a central role in the activation and differentiation of muscle satellite cells (Rantanen et al., 1995). MyoD functions in determining the myogenic fate of satellite cells, whereas myogenin appears to function in terminal muscle cell differentiation (Andres and Walsh, 1996; Montarras et al., 1991).

Figure 8:
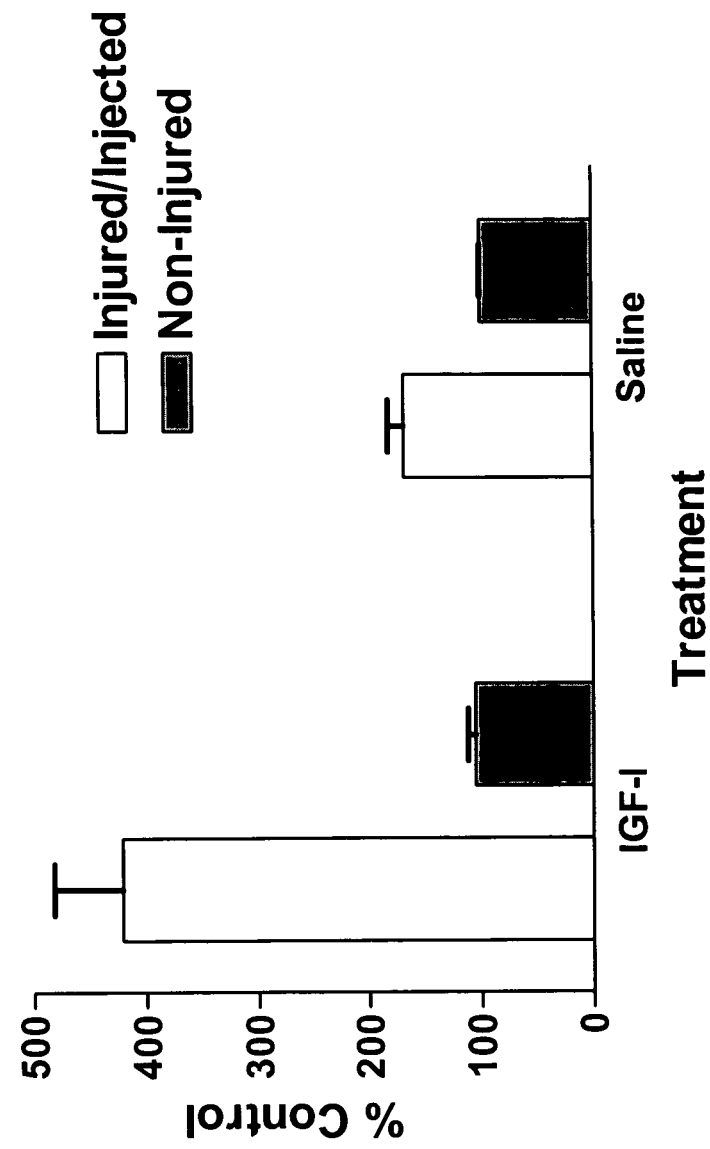
FIG. 8 shows the expression of MyoD in the tibialis anterior muscle of mice. Data is presented as the percent control of contralateral non-injured muscle from IGF-I and water injected mice. *$P<0.05$ in IGF-I injected vs. water injected muscle (n=3/group).

Induction of MyoD expression in injured tibialis anterior muscle after IGF-I gene injection. The sciatic nerve of ICR-I female mice was crushed mid thigh. Afterwards, 120 µg of pSP-IGF-I-SK3'UTR (pAV2001-SEQ ID NO.: 1), diluted in distilled water was injected in the tibialis anterior in a volume of 30 µl. The muscle was then electroporated at 220V/cm, 20 msec, and 3 pulses, positive and reverse polarity, each. In control mice, 30 µl of distilled water was injected into injured muscle and electroporated as above. After 3 days, the muscle of IGF-I and water-injected mice was analyzed with CELISA. As shown in FIG. 8, there is a 1.5-fold increase in MyoD expression in water-injected muscles. This reflects the baseline differentiation response of satellite cells to a nerve injury. In contrast, muscle injected with pSP-IGF-I-SK3'UTR (pAV2001-SEQ ID NO.: 1) exhibited a 3.5-fold increased in MyoD expression after injury.

Figure 9:
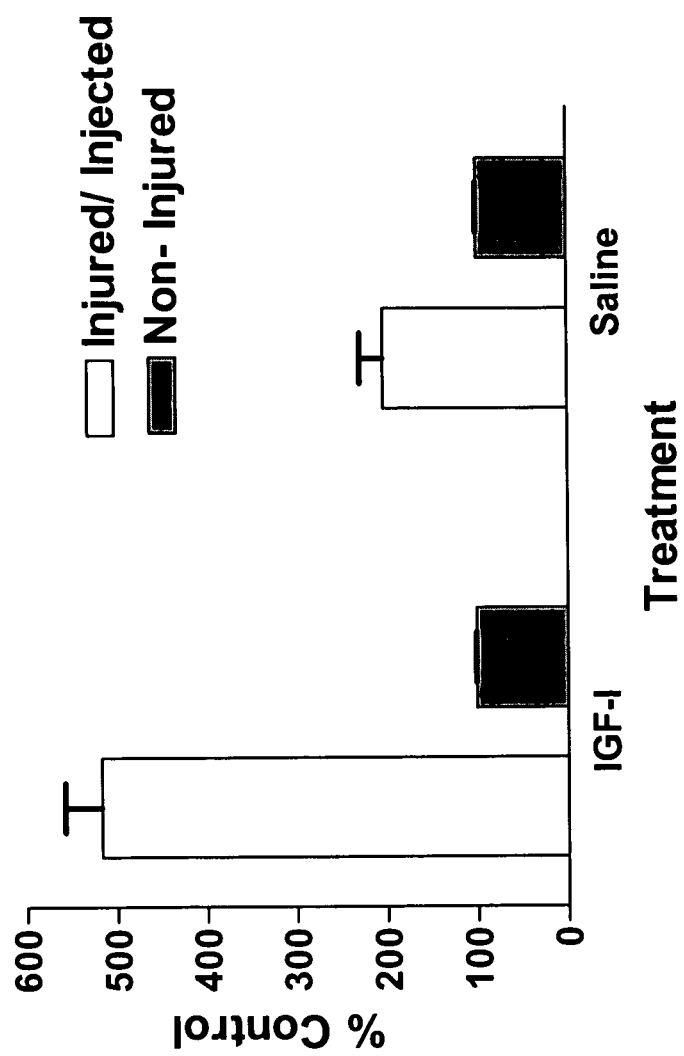
FIG. 9 shows the expression of myogenin in tibialis anterior muscle. Data is presented as the percent control of contralateral non-injured muscle from IGF-I and water injected mice. *P<0.05 in IGF-I injected vs. water injected muscle (n=3/group).

Induction of myogenin expression in injured tibialis anterior muscle after IGF-I gene injection. The sciatic nerve of ICR-I female mice was crushed mid thigh. Afterwards, 120 µg of pSP-IGF-I-SK3'UTR (pAV2001-SEQ ID NO.: 1) diluted in distilled water was injected in the tibialis anterior in a volume of 30 µl . The muscle was then electroporated at 220V/cm, 20 msec, and 3 pulses, positive and reverse polarity, each. In control mice, 30 µl of distilled water was injected into injured muscle and electroporated as above. After 3 days, the muscle of IGF-I and water-injected mice was analyzed with CELISA. As shown in FIG. 9, IGF-I injected muscle exhibited a 5-fold increase in myogenin expression. In contrast, water-injected muscle exhibited a 2-fold increase in myogenin expression. These results show that IGF-I plasmid mediated therapy intensifies the muscle regeneration pathways after a nerve injury, by accelerating the myogenic differentiation pathway.

Nerve injury to IGF-I transgenic mice has been shown to induce angiogenesis in skeletal muscle. VEGF (SEQ ID NO.7) is a potent endothelial proliferation factor which is induced in response to hypoxia and tissue injury, stimulating neo-vascularization in accordance with increasing metabolic demands of growing tissue. Upon injury to the muscle, angiogenesis in induced to re-vascularize the regenerated muscle. The expression of VEGF is critical for the proliferation, differentiation and chemotaxis of endothelial cells (Flamme et al., 1995; Leung et al., 1989), which is an initiating event of the angiogenic process.

Figure 10:
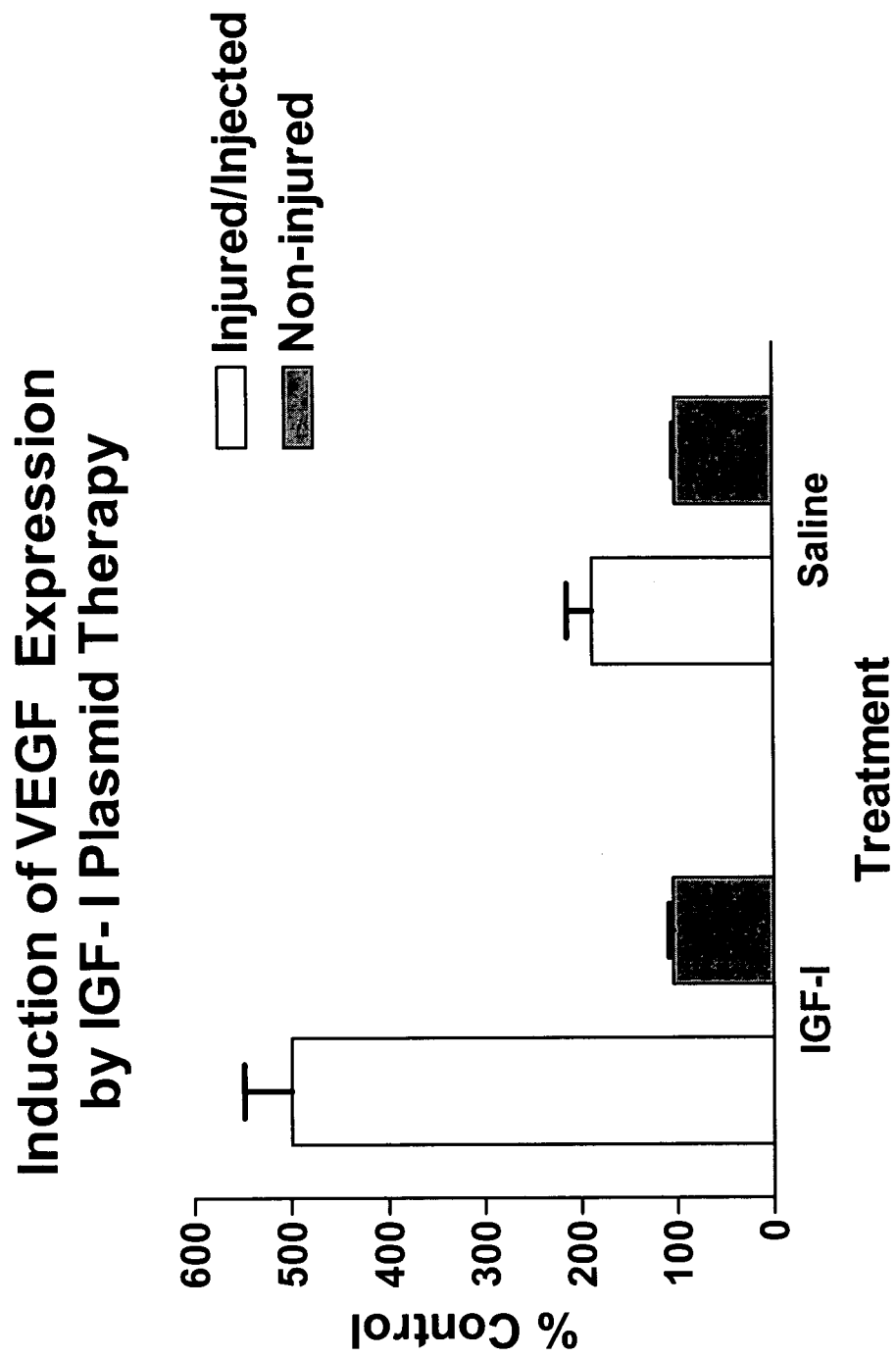
FIG. 10 shows the expression of VEGF in tibialis anterior muscle. Data is presented as the percent control of contralateral non-injured muscle from IGF-I and water injected mice. *P<0.05 in IGF-I injected vs. water injected muscle (n=3/group).

Induction of VEGF expression in injured tibialis anterior muscle after IGF-I gene injection. The sciatic nerve of ICR-I female mice was crushed mid thigh. Afterwards, 120 µg of pSP-IGF-I-SK3'UTR (pAV2001-SEQ ID NO.: 1) diluted in distilled water was injected in the tibialis anterior in a volume of 30 µl. The muscle was then electroporated at 220V/cm, 20 msec, and 3 pulses, positive and reverse polarity, each. In control mice, 30 µl of distilled water was injected into injured muscle and electroporated as above. After 3 days, the muscle of IGF-I and water-injected mice was analyzed with CELISA. As shown in FIG. 10, VEGF protein expression increased 3.5 fold in IGF-1-treated muscles. In contrast, VEGF expression was increased only 1.4 fold in water-treated muscle. The results show that IGF-I plasmid mediated supplementation induces the initiation of the angiogenic pathway in muscle after a nerve injury by induction of VEGF expression.

Furthermore, VEGF immuno-reactivity is localized to satellite cells and is increased significantly in IGF-I-injected muscle. Three days after nerve injury, muscles were fixed at 4% paraformaldehyde, cryo-sectioned to 10 microns, and stained with monoclonal antibody to VEGF. VEGF is up-regulated in muscle satellite cells and potentially in newly forming vessels. In contrast, VEGF-positive cells are only minimally detectable at this time point. VEGF receptors FLK-1 and FLT-1, major mediators of angiogenesis, are also stimulated by this method.

Figure 11:
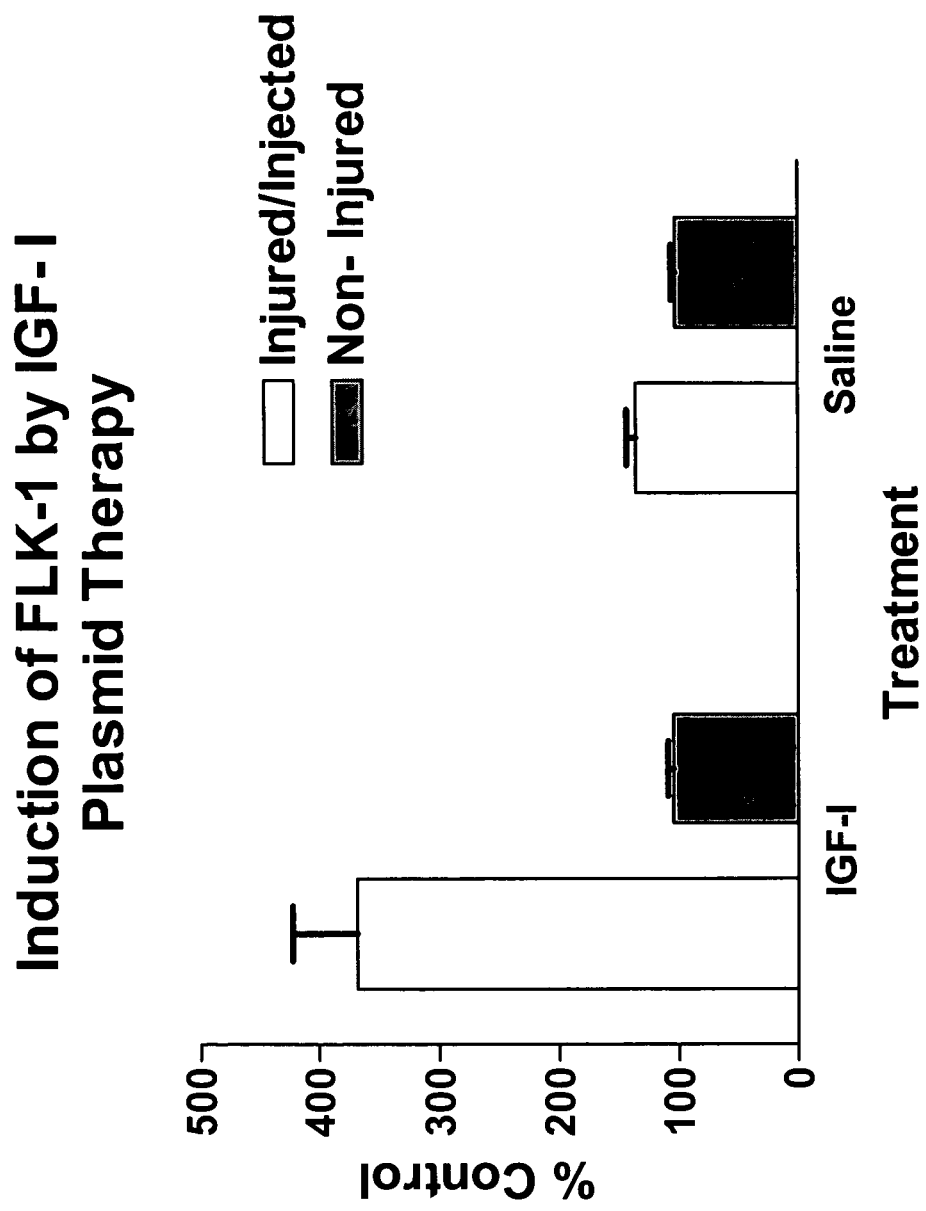
FIG. 11 shows the expression of FLK-1/KDR in tibialis anterior muscle. Data is presented as the percent control of contralateral non-injured muscle from IGF-I and water injected mice. *P<0.05 in IGF-I injected vs. water injected muscle (n=3/group).

Induction of FLK-1/KDR expression in injured tibialis anterior muscle after IGF-I gene injection. The sciatic nerve of ICR-I female mice was crushed mid thigh. Afterwards, 120 µg of pSP-IGF-I-SK3'UTR (pAV2001-SEQ ID NO.: 1), diluted in distilled water was injected in the tibialis anterior in a volume of 30 µl. The muscle was then electroporated at 220V/cm, 20 msec, and 3 pulses, positive and reverse polarity, each. In control mice, 30 µl of distilled water was injected into injured muscle and electroporated as above. After 3 days, the muscle of IGF-I and water-injected mice was analyzed with CELISA. The results shown in FIG. 11 indicate that IGF-I plasmid mediated supplemetation enhances the expression of FLK-1/KDR in skeletal muscle, which drives endothelial cell proliferation and migration.

Induction of FLT-1 expression in injured tibialis anterior muscle after IGF-I gene injection. Expression of FLT-1 represents the VEGF signaling pathways that induces vessel sprouting. Experiments were done to determine the effects of IGF-I plasmid mediated supplemetation on FLT-1 expression after a nerve injury. The sciatic nerve of ICR-I female mice was crushed mid thigh. Afterwards, 120 µg of pSP-IGF-I-SK3'UTR (pAV2001-SEQ ID NO.: 1), diluted in distilled water was injected in the tibialis anterior in a volume of 30 µl.

Figure 12:
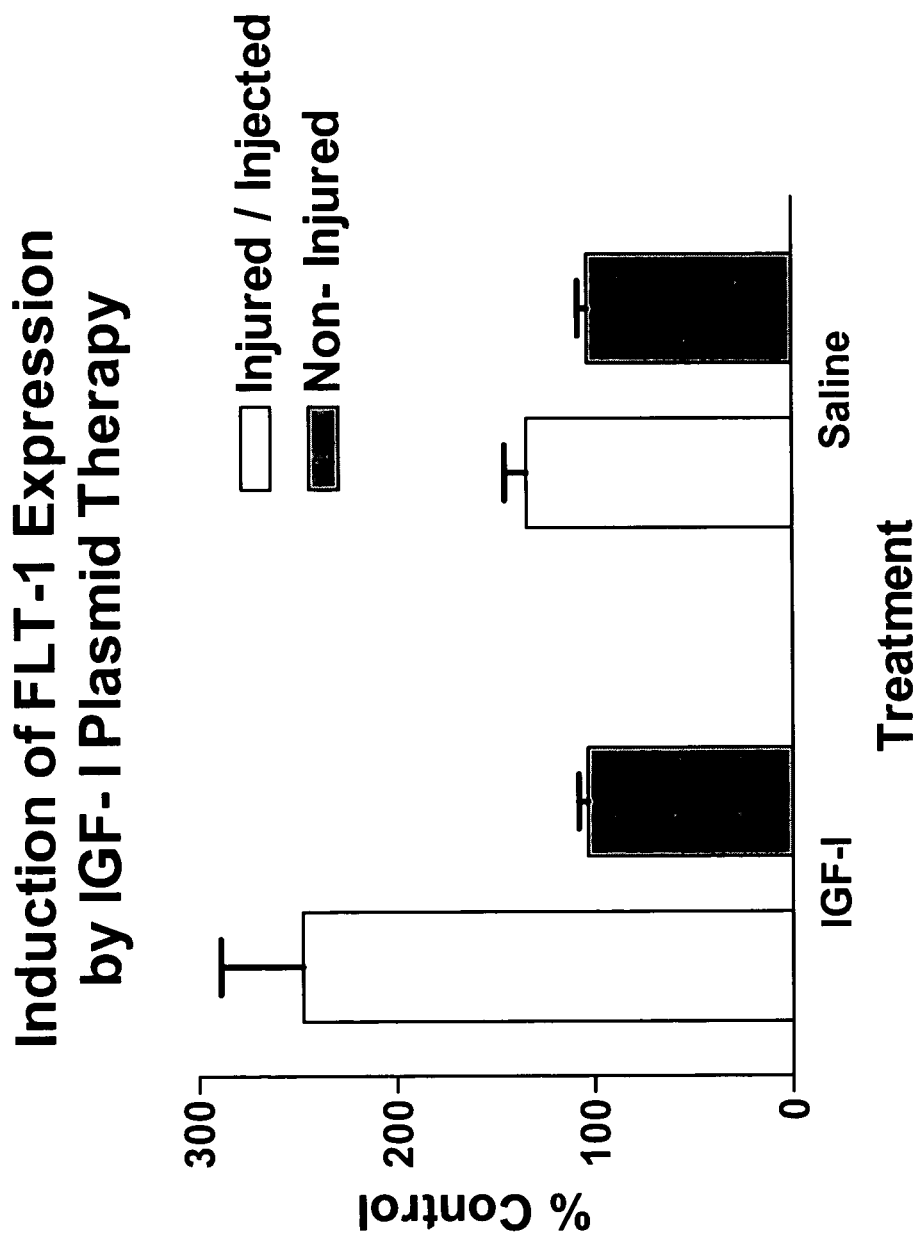
FIG. 12 shows the expression of FLT-1 in tibialis anterior muscle. Data is presented as the percent control of contralateral non-injured muscle from IGF-I and water injected mice. *P<0.05 in IGF-I injected vs. water injected muscle (n=3/group).

The muscle was then electroporated at 220V/cm, 20 msec, and 3 pulses, positive and reverse polarity, each. In control mice, 30 μl of distilled water was injected into injured muscle and electroporated as above. After 3 days, the muscle of IGF-I and water-injected mice was analyzed with CELISA. The results shown in FIG. 12 indicate that IGF-I plasmid mediated supplementation enhances the expression of FLT-1 in skeletal muscle, a receptor pathway that serves to induce sprouting of newly formed vessels.

The functional ability of IGF-I to induce angiogenesis was assessed in a diabetic model. Diabetes is a major risk factor for cardiovascular diseases (Meigs et al., 1997; Meigs et al., 2002). In the case of peripheral artery disease, hospital mortality, length of hospitalization, and complications resulting from surgery, and limb amputations are all increased in the presence of diabetes (Bagust et al., 2002; Currie et al., 1998). Early in the course of diabetes, intracellular hyperglycemia causes endothelial dysfunction and hemodynamic abnormalities. With time, endothelial cells are lost through apoptosis pathways and arteriole and capillary occlusion lead to microvascular rarefaction. This sequence of events leads to the formation of non-healing limb ulcers and limits the benefit of revascularization (Bagust et al., 2002). Collateralization is insufficient to overcome the loss of blood flow through occluded arteries in patients with peripheral vascular disease, and the problem is exacerbated in diabetics in whom collateralization is depressed (Feener and King, 1997; Rivard et al., 1999). This leads to severe pain due to lump ischemia and often loss of a limb. The mechanisms that hinder rapid revascularization in diabetic patients remain poorly understood, but angioblast mis-regulation, death, or dysfunction may contribute to the severe course of peripheral and cardiovascular complications seen.

Figure 13:
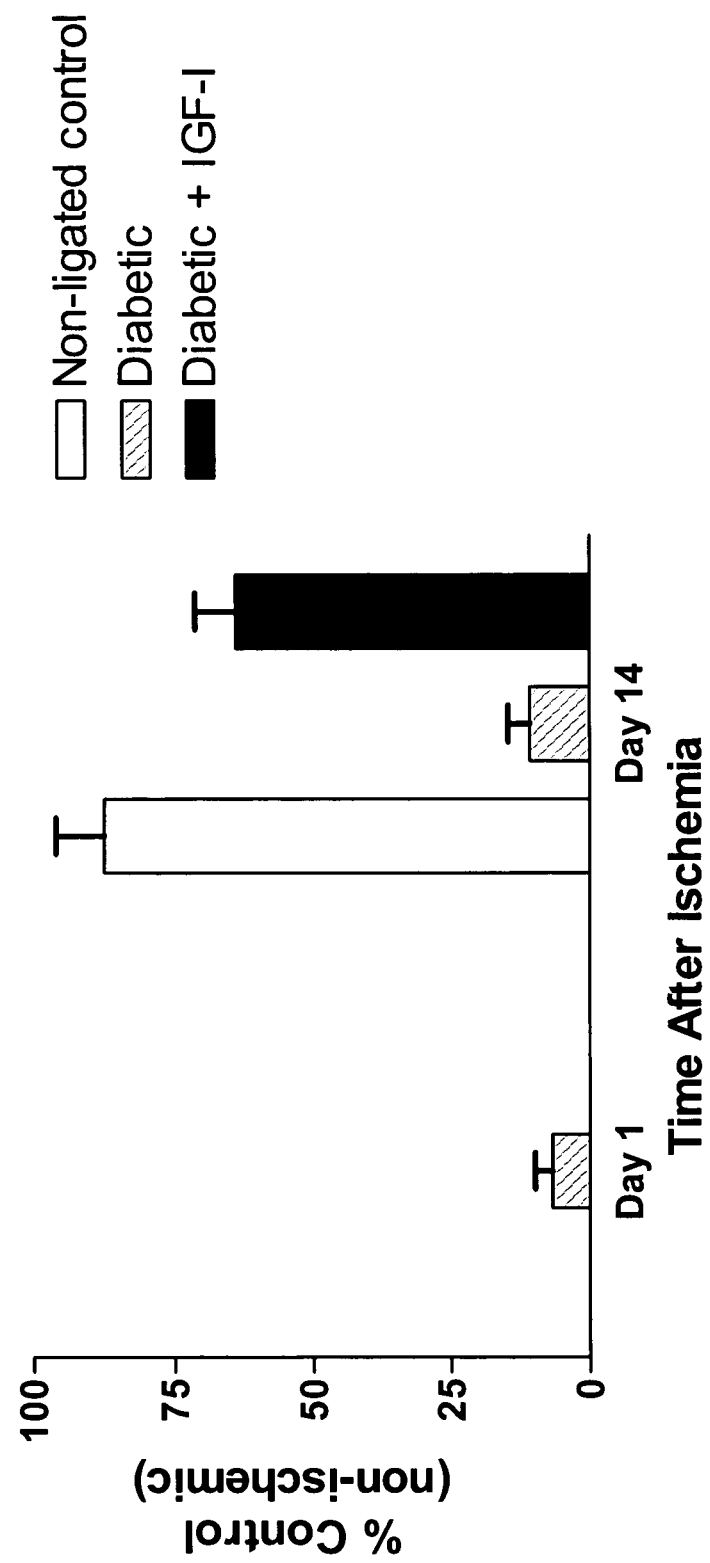
FIG. 13 shows the quantitation of angiogenic response of diabetic tibialis muscle to IGF-I plasmid mediated supplementation after femoral vessel ligation. Values are expressed as the percent control of non-ischemic tibialis anterior muscle (contralateral side) of IGF-I or water-treated muscles. *P<0.05 in IGF-I treatment vs. water treatment (n=3/group).

Given the potential therapeutic role of IGF-I in promoting angiogenesis, a diabetic femoral arterial occlusion model was employed to determine if IGF-I plasmid mediated therapy can reverse diabetic microangiopathy. Real time flow was assessed by Laser Doppler Imaging. One time point at 24 hours post-ligation was performed to ensure ligation was complete. Blood flow to the tibialis anterior muscle was severely diminished 24 hours after femoral artery occlusion, showing that blood flow was severely restricted in the model. Two weeks after surgery, flow to the tibialis anterior muscle was still severely compromised in water-injected muscles. In contrast, as shown in FIG. 13, IGF-I-treated muscle showed significant improvement in muscle blood flow. The flow rate was nearly 70% of normal tibialis blood flow. These results show that IGF-I plasmid mediated hormonal supplementation can be used to treat peripheral arterial disease in the diabetic state.

References Cited

The following references, to the extent that they provide exemplary procedural or other details supplementary to those set forth herein, are specifically incorporated herein by reference.

U.S. Patent Documents

U.S. Pat. No. 4,683,202 issued on Jul. 28, 1987 with Mullis listed as inventor.
U.S. Pat. No. 4,956,288 issued on Sep. 11, 1990 with Barsoum listed as inventor.
U.S. Pat. No. 5,298,422 issued on Mar. 29, 1994 with Schwartz, et al. listed as inventors.
U.S. Pat. No. 5,374,544 issued on Dec. 20, 1994 with Schwartz, et al. listed as inventors.
U.S. Pat. No. 5,384,253 issued on Jan. 24, 1995 with Krzyzek, et al. as inventors.
U.S. Pat. No. 5,439,440 issued on Aug. 8, 1995 with Hofmann listed as inventor.
U.S. Pat. No. 5,702,384 issued on Dec. 30, 1997 with Umeyama, et al. listed as inventors.
U.S. Pat. No. 5,704,908 issued on Jan. 6, 1998 with Hofmann, et al. listed as inventors.
U.S. Pat. No. 5,756,264 issued on May 26, 1998 with Schwartz, et al. listed as inventors.
U.S. Pat. No. 5,925,564 issued on Jul. 20, 1999 with Schwartz, et al. listed as inventors.
U.S. Pat. No. 5,925,565 issued on Jul. 20, 1999 with Berlioz, et al. listed as inventors.
U.S. Pat. No. 5,928,906 issued on Jul. 27, 1999 with Koster, et al. listed as inventors.
U.S. Pat. No. 5,935,819 issued on Aug. 10, 1999 with Eichner, et al. listed as inventors.
U.S. Pat. No. 5,955,365 issued on Sep. 21, 1999 with Szoka, et al. listed as inventors.
U.S. Pat. No. 6,150,168 issued on Nov. 21, 2000 with Woo, et al. listed as inventors.
U.S. Pat. No. 6,177,554 issued on Jan. 23, 2001 with Woo, et al. listed as inventors.

Other Publications

AIHARA, H. and J. Miyazaki. 1998. Gene transfer into muscle by electroporation in vivo. Nat. Biotechnol. 16:867-870.

AKENO, N., J. Robins, M. Zhang, M. F. Czyzyk-Krzeska, and T. L. Clemens. 2002. Induction of vascular endothelial growth factor by IGF-I in osteoblast-like cells is mediated by the PI3K signaling pathway through the hypoxia-inducible factor-2alpha. Endocrinology 143:420-425.

ALILA, H., M. Coleman, H. Nitta, M. French, K. Anwer, Q. Liu, T. Meyer, J. Wang, R. Mumper, D. Oubari, S. Long, J. Nordstrom, and A. Rolland. 1997. Expression of biologically active human insulin-like growth factor-I following intramuscular injection of a formulated plasmid in rats. Hum. Gene Ther. 8:1785-1795.

ALMENDRO, N., T. Bellon, C. Rius, P. Lastres, C. Langa, A. Corbi, and C. Bernabeu. 1996. Cloning of the human platelet endothelial cell adhesion molecule-1 promoter and its tissue-specific expression. Structural and functional characterization. J. Immunol. 157:5411-5421.

ANDRES, V. and K. Walsh. 1996. Myogenin expression, cell cycle withdrawal, and phenotypic differentiation are temporally separable events that precede cell fusion upon myogenesis. J. Cell Biol. 132:657-666.

ARATANI, Y., R. Okazaki, and H. Koyama. 1992. End extension repair of introduced targeting vectors mediated by homologous recombination in mammalian cells. Nucleic Acids Res. 20:4795-4801.

ARTHUR, W. T., R. B. Vernon, E. H. Sage, and M. J. Reed. 1998. Growth factors reverse the impaired sprouting of microvessels from aged mice. Microvasc. Res. 55:260-270.

BAGUST, A., P. K. Hopkinson, L. Maslove, and C. J. Currie. 2002. The projected health care burden of Type 2 diabetes in the UK from 2000 to 2060. Diabet. Med. 19 Suppl 4:1-5.:1-5.

BARTON-DAVIS, E. R., D. I. Shoturma, A. Musaro, N. Rosenthal, and H. L. Sweeney. 1998. Viral mediated expression of insulin-like growth factor I blocks the aging-related loss of skeletal muscle function [In Process Citation]. Proc. Natl. Acad. Sci. U.S. A. 95:15603-15607.

BECKMAN, J. A., Creager, M. A., Libby, P., 2002. Diabetes and atherosclerosis: epidemiology, pathophysiology, and management. JAMA 287, 2570-2581.

BERMONT, L., F. Lamielle, S. Fauconnet, H. Esumi, A. Weisz, and G. L. Adessi. 2000. Regulation of vascular endothelial growth factor expression by insulin-like growth factor-I in endometrial adenocarcinoma cells. Int. J. Cancer 85:117-123.

BETTAN, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.

BOSHART, M., F. Weber, G. Jahn, K. Dorsch-Hasler, B. Fleckenstein, and W. Schaffner. 1985. A very strong enhancer is located upstream of an immediate early gene of human cytomegalovirus. Cell 41:521-530.

BUERKE, M., T. Murohara, C. Skurk, C. Nuss, K. Tomaselli, and A. M. Lefer. 1995. Cardioprotective effect of insulin-like growth factor I in myocardial ischemia followed by reperfusion. Proc. Natl. Acad. Sci. U.S. A 92:8031-8035.

CARBONELLI, D. L., E. Corley, M. Seigelchifer, and J. Zorzopulos. 1999. A plasmid vector for isolation of strong promoters in *Escherichia coli*. FEMS Microbiol. Lett. 177: 75-82.

CARONI, P., C. Schneider, M. C. Kiefer, and J. Zapf. 1994. Role of muscle insulin-like growth factors in nerve sprouting: suppression of terminal sprouting in paralyzed muscle by IGF-binding protein 4. J. Cell Biol. 125:893-902.

CASTELLON, R., H. K. Hamdi, I. Sacerio, A. M. Aoki, M. C. Kenney, and A. V. Ljubimov. 2002. Effects of angiogenic growth factor combinations on retinal endothelial cells. Exp. Eye Res. 74:523-535.

CHANDLER, S. D., A. Mayeda, J. M. Yeakley, A. R. Krainer, and X. D. Fu. 1997. RNA splicing specificity determined by the coordinated action of RNA recognition motifs in SR proteins. Proc. Natl. Acad. Sci. U.S. A 94:3596-3601.

CHENG, H. L., A. Randolph, D. Yee, P. Delafontaine, G. Tennekoon, and E. L. Feldman. 1996. Characterization of insulin-like growth factor-I and its receptor and binding proteins in transected nerves and cultured Schwann cells. J. Neurochem. 66:525-536.

COCEA, L. 1997. Duplication of a region in the multiple cloning site of a plasmid vector to enhance cloning-mediated addition of restriction sites to a DNA fragment. Biotechniques 23:814-816.

COLEMAN, M. E., F. DeMayo, K. C. Yin, H. M. Lee, R. Geske, C. Montgomery, and R. J. Schwartz. 1995. Myogenic vector expression of insulin-like growth factor I stimulates muscle cell differentiation and myofiber hypertrophy in transgenic mice. J. Biol. Chem. 270:12109-12116.

CRIQUI, M. H., 2001. Peripheral arterial disease—epidemiological aspects. Vasc. Med. 6, 3-7.

CURRIE, C. J., C. L. Morgan, and J. R. Peters. 1998. The epidemiology and cost of inpatient care for peripheral vascular disease, infection, neuropathy, and ulceration in diabetes. Diabetes Care 21:42-48.

DAI, B., H. Wu, E. Holthuizen, and P. Singh. 2001. Identification of a novel cis element required for cell density-dependent down-regulation of insulin-like growth factor-2 P3 promoter activity in Caco2 cells. J. Biol. Chem. 276: 6937-6944.

DANKO, I. and J. A. Wolff. 1994. Direct gene transfer into muscle. [Review]. Vaccine 12:1499-1502.

DARQUET, A. M., B. Cameron, P. Wils, D. Scherman, and J. Crouzet. 1997. A new DNA vehicle for nonviral gene delivery: supercoiled minicircle. Gene Ther. 4:1341-1349.

DARQUET, A. M., R. Rangara, P. Kreiss, B. Schwartz, S. Naimi, P. Delaere, J. Crouzet, and D. Scherman. 1999. Minicircle: an improved DNA molecule for in vitro and in vivo gene transfer. Gene Ther. 6:209-218.

DAVIS, H. L., R. G. Whalen, and B. A. Demeneix. 1993. Direct gene transfer into skeletal muscle in vivo: factors affecting efficiency of transfer and stability of expression. Human Gene Therapy 4:151-159.

DAVIS, S., N. Papadopoulos, T. H. Aldrich, P. C. Maisonpierre, T. Huang, L. Kovac, A. Xu, R. Leidich, E. Radziejewska, A. Rafique, J. Goldberg, V. Jain, K. Bailey, M. Karow, J. Fandl, S. J. Samuelsson, E. Ioffe, J. S. Rudge, T. J. Daly, C. Radziejewski, and G. D. Yancopoulos. 2003. Angiopoietins have distinct modular domains essential for receptor binding, dimerization and superclustering. Nat. Struct. Biol. 10:38-44.

DE LUCA, A., S. Piemo, C. Camerino, D. Cocchi, and D.C. Camerino. 1999. Higher content of insulin-like growth factor-I in dystrophic mdx mouse: potential role in the spontaneous regeneration through an electrophysiological investigation of muscle function. Neuromuscul. Disord. 9:11-18.

DOLNIK, V., M. Novotny, and J. Chmelik. 1993. Electromigration behavior of poly-(L-glutamate) conformers in concentrated polyacrylamide gels. Biopolymers 33:1299-1306.

DONATH, M. Y., M. A. Gosteli-Peter, C. Hauri, E. R. Froesch, and J. Zapf. 1997. Insulin-like growth factor-I stimulates myofibrillar genes and modulates atrial natriuretic factor mRNA in rat heart. Eur. J. Endocrinol. 137:309-315.

DONATH, M. Y., G. Sutsch, X. W. Yan, B. Piva, H. P. Brunner, Y. Glatz, J. Zapf, F. Follath, E. R. Froesch, and W. Kiowski. 1998. Acute cardiovascular effects of insulin-like growth factor I in patients with chronic heart failure. J. Clin. Endocrinol. Metab 83:3177-3183.

DONATH, M. Y., J. Zapf, M. Eppenberger-Eberhardt, E. R. Froesch, and H. M. Eppenberger. 1994. Insulin-like growth factor I stimulates myofibril development and decreases smooth muscle alpha-actin of adult cardiomyocytes. Proc. Natl. Acad. Sci. U.S.A 91:1686-1690.

DORSCH-HASLER, K., G. M. Keil, F. Weber, M. Jasin, W. Schaffner, and U. H. Koszinowski. 1985. A long and complex enhancer activates transcription of the gene coding for the highly abundant immediate early mRNA in murine cytomegalovirus. Proc. Natl. Acad. Sci. U.S. A 82:8325-8329.

DRAGHIA-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

DRAGHIA-Akli, R., A. S. Khan, K. K. Cummings, D. Parghi, R. H. Carpenter, and P. A. Brown. 2002a. Electrical Enhancement of Formulated Plasmid Delivery in Animals. Technology in Cancer Research & Treatment 1:365-371.

DRAGHIA-Akli, R., P. B. Malone, L. A. Hill, K. M. Ellis, R. J. Schwartz, and J. L. Nordstrom. 2002. Enhanced animal growth via ligand-regulated GHRH myogenic-injectable vectors. FASEB J. 16:426-428.

DUERR, R. L., M. D. McKiman, R. D. Gim, R. G. Clark, K. R. Chien, and J. Ross, Jr. 1996. Cardiovascular effects of insulin-like growth factor-I and growth hormone in chronic left ventricular failure in the rat. Circulation 93:2188-2196.

FEENER, E. P. and G. L. King. 1997. Vascular dysfunction in diabetes mellitus. Lancet 350 Suppl 1:SI9-13.:SI9-13.

FEWELL, J. G., F. MacLaughlin, V. Mehta, M. Gondo, F. Nicol, E. Wilson, and L. C. Smith. 2001. Gene therapy for the treatment of hemophilia B using PINC-formulated plasmid delivered to muscle with electroporation. Mol. Ther. 3:574-583.

FIORELLI, G., L. Formigli, O. S. Zecchi, F. Gori, A. Falchetti, A. Morelli, A. Tanini, S. Benvenuti, and M. L. Brandi. 1996. Characterization and function of the receptor for IGF-I in human preosteoclastic cells. Bone 18:269-276.

FIORELLI, G., C. Orlando, S. Benvenuti, F. Franceschelli, S. Bianchi, P. Pioli, A. Tanini, M. Serio, F. Bartucci, and M. L. Brandi. 1994. Characterization, regulation, and function of specific cell membrane receptors for insulin-like growth factor I on bone endothelial cells. J Bone Miner. Res. 9:329-337.

FLAMME, I., G. Breier, and W. Risau. 1995. Vascular endothelial growth factor (VEGF) and VEGF receptor 2 (flk-1) are expressed-during vasculogenesis and vascular differentiation in the quail embryo. Dev. Biol. 169:699-712.

FLORINI, J. R., D. Z. Ewton, K. A. Magri, and F. J. Mangiacapra. 1993. IGFs and muscle differentiation. Adv. Exp. Med. Biol. 343:319-26:319-326.

FLORINI, J. R., K. A. Magri, D. Z. Ewton, P. L. James, K. Grindstaff, and P. S. Rotwein. 1991. "Spontaneous" differentiation of skeletal myoblasts is dependent upon autocrine secretion of insulin-like growth factor-II. J. Biol. Chem. 266:15917-15923.

FOLKMAN, J. 1995. Angiogenesis in cancer, vascular, rheumatoid and other disease. Nat. Med. 1:27-31.

FOLKMAN, J. and M. Klagsbrun. 1987. Angiogenic factors. Science 235:442-447.

FOWLER, B., Jamrozik, K., Norman, P., Allen, Y., 2002. Prevalence of peripheral arterial disease: persistence of excess risk in former smokers. Aust. N. Z. J Public Health 26, 219-224.

FRYER, A. D. and D. B. Jacoby. 1993. Effect of inflammatory cell mediators on M2 muscarinic receptors in the lungs. Life Sci. 52:529-536.

GEHL, J., T. Skovsgaard, and L. M. Mir. 1998. Enhancement of cytotoxicity by electropermeabilization: an improved method for screening drugs. Anticancer Drugs 9:319-325.

GEHL, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

GERMAN, M., S. Ashcroft, K. Docherty, H. Edlund, T. Edlund, S. Goodison, H. Imura, G. Kennedy, O. Madsen, D. Melloul, and. 1995. The insulin gene promoter. A simplified nomenclature. Diabetes 44:1002-1004.

GLAZNER, G. W., A. E. Morrison, and D. N. Ishii. 1994. Elevated insulin-like growth factor (IGF) gene expression in sciatic nerves during IGF-supported nerve regeneration. Brain Res. Mol. Brain Res. 25:265-272.

GOAD, D. L., J. Rubin, H. Wang, A. H. Tashjian, Jr., and C. Patterson. 1996. Enhanced expression of vascular endothelial growth factor in human SaOS-2 osteoblast-like cells and murine osteoblasts induced by insulin-like growth factor I. Endocrinology 137:2262-2268.

GOLDSPINK, G. 1999. Changes in muscle mass and phenotype and the expression of autocrine and systemic growth factors by muscle in response to stretch and overload. J. Anat. 194:323-334.

HELLER, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

HERZOG, R. W., J. D. Mount, V. R. Arruda, K. A. High, and C. D. Lothrop, Jr. 2001. Muscle-directed gene transfer and transient immune suppression result in sustained partial correction of canine hemophilia B caused by a null mutation. Mol. Ther. 4:192-200.

HORLICK, R. A. and P. A. Benfield. 1989. The upstream muscle-specific enhancer of the rat muscle creatine kinase gene is composed of multiple elements. Mol. Cell Biol. 9:2396-2413.

HORVATH, K. A., J. Doukas, C. Y. Lu, N. Belkind, R. Greene, G. F. Pierce, and D. A. Fullerton. 2002. Myocardial functional recovery after fibroblast growth factor 2 gene therapy as assessed by echocardiography and magnetic resonance imaging. Ann. Thorac. Surg. 74:481-486.

HSU, H. H., M. M. Zdanowicz, V. R. Agarwal, and P. W. Speiser. 1997. Expression of myogenic regulatory factors in normal and dystrophic mice: effects of IGF-I treatment. Biochem. Mol. Med. 60:142-148.

INOUYE, C., P. Remondelli, M. Karin, and S. Elledge. 1994. Isolation of a cDNA encoding a metal response element binding protein using a novel expression cloning procedure: the one hybrid system. DNA Cell Biol. 13:731-742.

INOUYE, S., A. Nakazawa, and T. Nakazawa. 1985. Determination of the transcription initiation site and identification of the protein product of the regulatory gene xylR for xyl operons on the TOL plasmid. J. Bacteriol. 163:863-869.

ITO, H., M. Hiroe, Y. Hirata, M. Tsujino, S. Adachi, M. Shichiri, A. Koike, A. Nogami, and F. Marumo. 1993. Insulin-like growth factor-I induces hypertrophy with enhanced expression of muscle specific genes in cultured rat cardiomyocytes. Circulation 87:1715-1721.

JABRI, N., D. S. Schalch, S. L. Schwartz, J. S. Fischer, M. S. Kipnes, B. J. Radnik, N.J. Turman, V. S. Marcsisin, and H. P. Guler. 1994. Adverse effects of recombinant human insulin-like growth factor I in obese insulin-resistant type II diabetic patients. Diabetes 43:369-374.

JAYNES, J. B., J. E. Johnson, J. N. Buskin, C. L. Gartside, and S. D. Hauschka. 1988. The muscle creatine kinase gene is regulated by multiple upstream elements, including a muscle-specific enhancer. Mol. Cell Biol. 8:62-70.

JESCHKE, M. G., R. E. Barrow, H. K. Hawkins, K. Yang, R. L. Hayes, B. J. Lichtenbelt, J. R. Perez-Polo, and D. N. Herndon. 1999. IGF-I gene transfer in thermally injured rats. Gene Ther. 6:1015-1020.

KAJSTURA, J., W. Cheng, K. Reiss, and P. Anversa. 1994. The IGF-I-IGF-I receptor system modulates myocyte proliferation but not myocyte cellular hypertrophy in vitro. Exp. Cell Res. 215:273-283.

Kardami, E. 1990. Stimulation and inhibition of cardiac myocyte proliferation in vitro. Mol. Cell Biochem. 92:129-135.

Kasemkijwattana, C., J. Menetrey, G. Somogyl, M. S. Moreland, F. H. Fu, B. Buranapanitkit, S. C. Watkins, and J. Huard. 1998. Development of approaches to improve the healing following muscle contusion. Cell Transplant. 7:585-598.

KAWAMOTO, T., K. Makino, H. Niwa, H. Sugiyama, S. Kimura, M. Amemura, A. Nakata, and T. Kakunaga. 1988. Identification of the human beta-actin enhancer and its binding factor. Mol. Cell Biol. 8:267-272.

KAWAMOTO, T., K. Makino, S. Orita, A. Nakata, and T. Kakunaga. 1989. DNA bending and binding factors of the human beta-actin promoter. Nucleic Acids Res. 17:523-537.

KELLY, P. J., J. A. Eisman, M. C. Stuart, N. A. Pocock, P. N. Sambrook, and T. H. Gwinn. 1990. Somatomedin-C, physical fitness, and bone density. J. Clin. Endocrinol. Metab. 70:718-723.

KLAMUT, H. J., L. O. Bosnoyan-Collins, R. G. Worton, P. N. Ray, and H. L. Davis. 1996. Identification of a transcriptional enhancer within muscle intron 1 of the human dystrophin gene. Hum. Mol. Genet. 5:1599-1606.

KLAMUT, H. J., S. B. Gangopadhyay, R. G. Worton, and P. N. Ray. 1990. Molecular and functional analysis of the muscle-specific promoter region of the Duchenne muscular dystrophy gene. Mol. Cell Biol. 10: 193-205.

KOBAYASHI, T. and K. Kamata. 2002. Short-term insulin treatment and aortic expressions of IGF-I receptor and VEGF mRNA in diabetic rats. Am. J. Physiol Heart Circ. Physiol 283:H1761-H1768.

KRAUS, J., M. Woltje, N. Schonwetter, and V. Hollt. 1998. Alternative promoter usage and tissue specific expression of the mouse somatostatin receptor 2 gene. FEBS Lett. 428:165-170.

LAREYRE, J. J., T. Z. Thomas, W. L. Zheng, S. Kasper, D. E. Ong, M. C. Orgebin-Crist, and R. J. Matusik. 1999. A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274:8282-8290.

LARSEN, P. R., J. W. Harney, and D. D. Moore. 1986. Sequences required for cell-type specific thyroid hormone regulation of rat growth hormone promoter activity. J. Biol. Chem. 261:14373-14376.

LEE, S. H., W. Wang, S. Yajima, P. A. Jose, and M. M. Mouradian. 1997. Tissue-specific promoter usage in the D1A dopamine receptor gene in brain and kidney. DNA Cell Biol. 16:1267-1275.

Lesbordes, J. C., T. Bordet, G. Haase, L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11:1615-1625.

LESCAUDRON, L., E. Peltekian, J. Fontaine-Perus, D. Paulin, M. Zampieri, L. Garcia, and E. Parrish. 1999. Blood borne macrophages are essential for the triggering of muscle regeneration following muscle transplant. Neuromuscul. Disord. 9:72-80.

LEUNG, D. W., G. Cachianes, W. J. Kuang, D. V. Goeddel, and N. Ferrara. 1989. Vascular endothelial growth factor is a secreted angiogenic mitogen. Science 246:1306-1309.

LEVENSON, V. V., E. D. Transue, and I. B. Roninson. 1998. Internal ribosomal entry site-containing retroviral vectors with green fluorescent protein and drug resistance markers. Hum. Gene Ther. 9:1233-1236.

LI, C., S. Ke, Q. P. Wu, W. Tansey, N. Hunter, L. M. Buchmiller, L. Milas, C. Chamsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

LI, X., E. M. Eastman, R. J. Schwartz, and R. Draghia-Akli. 1999. Synthetic muscle promoters: activities exceeding naturally occurring regulatory sequences. Nat. Biotechnol. 17:241-245.

LIN, H., K. E. Yutzey, and S. F. Konieczny. 1991. Muscle-specific expression of the troponin I gene requires interactions between helix-loop-helix muscle regulatory factors and ubiquitous transcription factors. Mol. Cell Biol. 11:267-280.

LIU, Y., H. Li, K. Tanaka, N. Tsumaki, and Y. Yamada. 2000. Identification of an enhancer sequence within the first intron required for cartilage-specific transcription of the alpha2(XI) collagen gene. J. Biol. Chem. 275:12712-12718.

LOMBARDI, G., A. Colao, A. Cuocolo, S. Longobardi, C. Di Somma, F. Orio, B. Merola, E. Nicolai, and M. Salvatore. 1997. Cardiological aspects of growth hormone and insulin-like growth factor-I. J. Pediatr. Endocrinol. Metab 10:553-560.

LUCAS, M. L., L. Heller, D. Coppola, and R. Heller. 2002. IL-12 plasmid delivery by in vivo electroporation for the successful treatment of established subcutaneous B16.F10 melanoma. Mol. Ther. 5:668-675.

LUCAS, M. L., M. J. Jaroszeski, R. Gilbert, and R. Heller. 2001. In vivo electroporation using an exponentially enhanced pulse: a new waveform. DNA Cell Biol. 20:183-188.

MACCOLL, G. S., G. Goldspink, and P. M. Bouloux. 1999. Using skeletal muscle as an artificial endocrine tissue. J. Endocrinol. 162:1-9.

MACEJAK, D. G. and P. Sarnow. 1991. Internal initiation of translation mediated by the 5' leader of a cellular mRNA. Nature 353:90-94.

MATSUBARA, H., Y. Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

MATSUO, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

MCNALLY, M. A., J. S. Lebkowski, T. B. Okarma, and L. B. Lerch. 1988. Optimizing electroporation parameters for a variety of human hematopoietic cell lines. Biotechniques 6:882-886.

MEIGS, J. B., M. G. Larson, R. B. D'Agostino, D. Levy, M. E. Clouse, D. M. Nathan, P. W. Wilson, and C. J. O'Donnell. 2002. Coronary artery calcification in type 2 diabetes and insulin resistance: the framingham offspring study. Diabetes Care 25:1313-1319.

MEIGS, J. B., D. E. Singer, L. M. Sullivan, K. A. Dukes, R. B. D'Agostino, D. M. Nathan, E. H. Wagner, S. H. Kaplan, and S. Greenfield. 1997. Metabolic control and prevalent cardiovascular disease in non-insulin-dependent diabetes mellitus (NIDDM): The NIDDM Patient Outcome Research Team. Am. J. Med. 102:38-47.

MENETREY, J., C. Kasemkijwattana, C. S. Day, P. Bosch, M. Vogt, F. H. Fu, M. S. Moreland, and J. Huard. 2000. Growth factors improve muscle healing in vivo. J. Bone Joint Surg. Br. 82:131-137.

MIELE, C., J. J. Rochford, N. Filippa, S. Giorgetti-Peraldi, and E. Van Obberghen. 2000. Insulin and insulin-like growth factor-I induce vascular endothelial growth factor mRNA expression via different signaling pathways. J. Biol. Chem. 275:21695-21702.

MIKLAVCIC, D., K. Beravs, D. Semrov, M. Cemazar, F. Demsar, and G. Sersa. 1998. The importance of electric field distribution for effective in vivo electroporation of tissues. Biophys. J 74:2152-2158.

MONTARRAS, D., J. Chelly, E. Bober, H. Arnold, M. O. Ott, F. Gros, and C. Pinset. 1991. Developmental patterns in the expression of Myf5, MyoD, myogenin, and MRF4 during myogenesis. New Biol. 3:592-600.

MUMPER, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

MURAMATSU, T., S. Arakawa, K. Fukazawa, Y. Fujiwara, T. Yoshida, R. Sasaki, S. Masuda, and H. M. Park. 2001. In vivo gene electroporation in skeletal muscle with special reference to the duration of gene expression. Int. J. Mol. Med. 7:37-42.

NAIRN, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

NARUM, D. L., S. Kumar, W. O. Rogers, S. R. Fuhrmann, H. Liang, M. Oakley, A. Taye, B. K. Sim, and S. L. Hoffman. 2001. Codon optimization of gene fragments encoding Plasmodium falciparum merzoite proteins enhances DNA vaccine protein expression and immunogenicity in mice. Infect. Immun. 69:7250-7253.

NEUMANN, E., M. Schaefer-Ridder, Y. Wang, and P. H. Hofschneider. 1982. Gene transfer into mouse lyoma cells by electroporation in high electric fields. EMBO J. 1:841-845.

NOMOTO, S., Y. Tatematsu, T. Takahashi, and H. Osada. 1999. Cloning and characterization of the alternative promoter regions of the human LIMK2 gene responsible for alternative transcripts with tissue-specific expression. Gene 236:259-271.

OHLSSON, H., S. Thor, and T. Edlund. 1991. Novel insulin promoter- and enhancer-binding proteins that discriminate between pancreatic alpha- and beta-cells. Mol. Endocrinol. 5:897-904.

OTANI, Y., Y. Tabata, and Y. Ikada. 1996. Rapidly curable biological glue composed of gelatin and poly(L-glutamic acid). Biomaterials 17:1387-1391.

OTANI, Y., Y. Tabata, and Y. Ikada. 1998. Hemostatic capability of rapidly curable glues from gelatin, poly(L-glutamic acid), and carbodiimide. Biomaterials 19:2091-2098.

PECH, M., C. D. Rao, K. C. Robbins, and S. A. Aaronson. 1989. Functional identification of regulatory elements within the promoter region of platelet-derived growth factor 2. Mol. Cell Biol. 9:396-405.

PELLETIER, J. and N. Sonenberg. 1988. Internal initiation of translation of eukaryotic mRNA directed by a sequence derived from poliovirus RNA. Nature 334:320-325.

PETERS, K. G. 1998. Vascular endothelial growth factor and the angiopoietins: working together to build a better blood vessel. Circ. Res. 83:342-343.

PINKERT, C. A., D. M. Ornitz, R. L. Brinster, and R. D. Palmiter. 1987. An albumin enhancer located 10 kb upstream functions along with its promoter to direct efficient, liver-specific expression in transgenic mice. Genes Dev. 1:268-276.

POTTER, H., L. Weir, and P. Leder. 1984. Enhancer-dependent expression of human kappa immunoglobulin genes introduced into mouse pre-B lymphocytes by electroporation. Proc. Natl. Acad. Sci. U.S.A 81:7161-7165.

PRENTICE, H., R. A. Kloner, T. Prigozy, T. Christensen, L. Newman, Y. Li, and L. Kedes. 1994. Tissue restricted gene expression assayed by direct DNA injection into cardiac and skeletal muscle. Journal of Molecular & Cellular Cardiology 26:1393-1401.

PUNGLIA, R. S., M. Lu, J. Hsu, M. Kuroki, M. J. Tolentino, K. Keough, A. P. Levy, N. S. Levy, M. A. Goldberg, R. J. D'Amato, and A. P. Adamis. 1997. Regulation of vascular endothelial growth factor expression by insulin-like growth factor I. Diabetes 46:1619-1626.

RABINOVSKY, E. D., E. Gelir, S. Gelir, H. Lui, M. Kattash, F. J. DeMayo, S. M. Shenaq, and R. J. Schwartz. 2003. Targeted expression of IGF-I transgene to skeletal muscle accelerates muscle and motor neuron regeneration. FASEB J 17:53-55.

RANTANEN, J., T. Hurme, R. Lukka, J. Heino, and H. Kalimo. 1995. Satellite cell proliferation and the expression of myogenin and desmin in regenerating skeletal muscle: evidence for two different populations of satellite cells. Lab Invest 72:341-347.

REINMUTH, N., F. Fan, W. Liu, A. A. Parikh, O. Stoeltzing, Y. D. Jung, C. D. Bucana, R. Radinsky, G. E. Gallick, and L. M. Ellis. 2002. Impact of insulin-like growth factor receptor-1 function on angiogenesis, growth, and metastasis of colon cancer. Lab Invest 82:1377-1389.

REISS, K., W. Cheng, A. Ferber, J. Kajstura, P. Li, B. Li, G. Olivetti, C. J. Homcy, R. Baserga, and P. Anversa. 1996. Overexpression of insulin-like growth factor-1 in the heart is coupled with myocyte proliferation in transgenic mice. Proc. Natl. Acad. Sci. U.S.A 93:8630-8635.

REISS, K., J. Kajstura, X. Zhang, P. Li, E. Szoke, G. Olivetti, and P. Anversa. 1994. Acute myocardial infarction leads to upregulation of the IGF-I autocrine system, DNA replication, and nuclear mitotic division in the remaining viable cardiac myocytes. Exp. Cell Res. 213:463-472.

RIVARD, A., M. Silver, D. Chen, M. Kearney, M. Magner, B. Annex, K. Peters, and J. M. Isner. 1999. Rescue of diabetes-related impairment of angiogenesis by intramuscular gene therapy with adeno-VEGF. Am. J. Pathol. 154:355-363.

SHIGEMATSU, S., K. Yamauchi, K. Nakajima, S. Iijima, T. Aizawa, and K. Hashizume.
1999. IGF-I regulates migration and angiogenesis of human endothelial cells. Endocr. J 46 Suppl:S59-62.:S59-S62.

SILVESTRE, J. S., Levy, B. I., 2002. Angiogenesis therapy in ischemic disease. Arch. Mal Coeur Vaiss. 95, 189-196.

SJOGREN, K., J. O. Jansson, O. G. Isaksson, and C. Ohlsson. 2002. A transgenic model to determine the physiological role of liver-derived insulin-like growth factor I. Minerva Endocrinol. 27:299-311.

SJOGREN, K., J. L. Liu, K. Blad, S. Skrtic, O. Vidal, V. Wallenius, D. LeRoith, J. Tornell, O. G. Isaksson, J. O. Jansson, and C. Ohlsson. 1999. Liver-derived insulin-like growth factor I (IGF-I) is the principal source of IGF-I in blood but is not required for postnatal body growth in mice. Proc. Natl. Acad. Sci. U.S. A 96:7088-7092.

SKROCH, P., C. Buchman, and M. Karin. 1993. Regulation of human and yeast metallothionein gene transcription by heavy metal ions. Prog. Clin. Biol. Res. 380:113-28.:113-128.

SMITH, L. C. and J. L. Nordstrom. 2000. Advances in plasmid gene delivery and expression in skeletal muscle. Curr. Opin. Mol. Ther. 2:150-154.

SONG, S., J. Embury, P. J. Laipis, K. I. Berns, J. M. Crawford, and T. R. Flotte. 2001. Stable therapeutic serum levels of human alpha-i antitrypsin (AAT) after portal vein injection of recombinant adeno-associated virus (rAAV) vectors. Gene Ther. 8:1299-1306.

SOUBRIER, F., B. Cameron, B. Manse, S. Somarriba, C. Dubertret, G. Jaslin, G. Jung, C. L. Caer, D. Dang, J. M. Mouvault, D. Scherman, J. F. Mayaux, and J. Crouzet.

1999. pCOR: a new design of plasmid vectors for nonviral gene therapy. Gene Ther. 6:1482-1488.

SPOERRI, P. E., E. A. Ellis, R. W. Tamuzzer, and M. B. Grant. 1998. Insulin-like growth factor: receptor and binding proteins in human retinal endothelial cell cultures of diabetic and non-diabetic origin. Growth Horm. IGF. Res. 8:125-132.

TERADA, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J. Kidney Dis. 38:S50-S53.

TONEGUZZO, F., A. Keating, S. Glynn, and K. McDonald. 1988. Electric field-mediated gene transfer: characterization of DNA transfer and patterns of integration in lymphoid cells. Nucleic Acids Res. 16:5515-5532.

TRIPATHY, S. K., E. C. Svensson, H. B. Black, E. Goldwasser, M. Margalith, Hobart, P M, and J. M. Leiden. 1996. Long-term expression of erythropoietin in the systemic circulation of mice after intramuscular injection of a plasmid DNA vector. Proc. Natl. Acad. Sci. USA 93:10876-10880.

TRONCHE, F., A. Rollier, I. Bach, M. C. Weiss, and M. Yaniv. 1989. The rat albumin promoter: cooperation with upstream elements is required when binding of APF/HNF1 to the proximal element is partially impaired by mutation or bacterial methylation. Mol. Cell Biol. 9:4759-4766.

TRONCHE, F., A. Rollier, P. Herbomel, I. Bach, S. Cereghini, M. Weiss, and M. Yaniv. 1990. Anatomy of the rat albumin promoter. Mol. Biol. Med. 7:173-185.

TRUDEL, M. and F. Costantini. 1987. A 3' enhancer contributes to the stage-specific expression of the human beta-globin gene. Genes Dev. 1:954-961.

TSUMAKI, N., T. Kimura, K. Tanaka, J. H. Kimura, T. Ochi, and Y. Yamada. 1998. Modular arrangement of cartilage- and neural tissue-specific cis-elements in the mouse alpha2 (XI) collagen promoter. J. Biol. Chem. 273:22861-22864.

TSURUMI, Y., S. Takeshita, D. Chen, M. Kearney, S. T. Rossow, J. Passeri, J. R. Horowitz, J. F. Symes, and J. M. Isner. 1996. Direct intramuscular gene transfer of naked DNA encoding vascular endothelial growth factor augments collateral development and tissue perfusion [see comments]. Circulation 94:3281-3290.

TUR-KASPA, R., L. Teicher, B. J. Levine, A. I. Skoultchi, and D. A. Shafritz. 1986. Use of electroporation to introduce biologically active foreign genes into primary rat hepatocytes. Mol. Cell Biol. 6:716-718.

VANCE, M. L. 1990. Growth-hormone-releasing hormone. [Review] [52 refs]. Clinical Chemistry 36:415-420.

VANDENBURGH, H. H., P. Karlisch, J. Shansky, and R. Feldstein. 1991. Insulin and IGF-I induce pronounced hypertrophy of skeletal myofibers in tissue culture. Am. J. Physiol. 260:C475-C484.

VEIKKOLA, T., M. Karkkainen, L. Claesson-Welsh, and K. Alitalo. 2000. Regulation of angiogenesis via vascular endothelial growth factor receptors. Cancer Res. 60:203-212.

VILQUIN, J. T., P. F. Kennel, M. Patumeau-Jouas, P. Chapdelaine, N. Boissel, P. Delaere, J. P. Tremblay, D. Scherman, M. Y. Fiszman, and K. Schwartz. 2001. Electrotransfer of naked DNA in the skeletal muscles of animal models of muscular dystrophies. Gene Ther. 8:1097-1107.

WALSH, M. F., M. Barazi, G. Pete, R. Muniyappa, J. C. Dunbar, and J. R. Sowers. 1996. Insulin-like growth factor I diminishes in vivo and in vitro vascular contractility: role of vascular nitric oxide. Endocrinology 137:1798-1803.

WANG, L., W. Ma, R. Markovich, J. W. Chen, and P. H. Wang. 1998a. Regulation of cardiomyocyte apoptotic signaling by insulin-like growth factor I. Circ. Res. 83:516-522.

WANG, L., W. Ma, R. Markovich, W. L. Lee, and P. H. Wang. 1998b. Insulin-like growth factor I modulates induction of apoptotic signaling in H9C2 cardiac muscle cells. Endocrinology 139:1354-1360.

WELLS, K. E., J. Maule, R. Kingston, K. Foster, J. McMahon, E. Damien, A. Poole, and D. J. Wells. 1997. Immune responses, not promoter inactivation, are responsible for decreased long-term expression following plasmid gene transfer into skeletal muscle. FEBS Lett. 407:164-168.

WOLFF, J. A., R. W. Malone, P. Williams, W. Chong, G. Acsadi, A. Jani, Felgner, and PL. 1990. Direct gene transfer into mouse muscle in vivo. Science 247:1465-1468.

WU, H. K., J. A. Squire, Q. Song, and R. Weksberg. 1997. Promoter-dependent tissue-specific expressive nature of imprinting gene, insulin-like growth factor II, in human tissues. Biochem. Biophys. Res. Commun. 233:221-226.

WU, Y., S. Yakar, L. Zhao, L. Hennighausen, and D. LeRoith. 2002. Circulating insulin-like growth factor-I levels regulate colon cancer growth and metastasis. Cancer Res. 62:1030-1035.

XIE, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

YASUI, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J. Mol. Med. 8:489-494.

YIN, D. and J. G. Tang. 2001. Gene therapy for streptozotocin-induced diabetic mice by electroporational transfer of naked human insulin precursor DNA into skeletal muscle in vivo. FEBS Lett. 495:16-20.

YORIFUJI, T. and H. Mikawa. 1990. Co-transfer of restriction endonucleases and plasmid DNA into mammalian cells by electroporation: effects on stable transformation. Mutat. Res. 243:121-126.

YUTZEY, K. E. and S. F. Konieczny. 1992. Different E-box regulatory sequences are functionally distinct when placed within the context of the troponin I enhancer. Nucleic Acids Res. 20:5105-5113.

ZHAO-EMONET, J. C., O. Boyer, J. L. Cohen, and D. Klatzmann. 1998. Deletional and mutational analyses of the human CD4 gene promoter: characterization of a minimal tissue-specific promoter. Biochim. Biophys. Acta 1442:109-119.

ZHUANG, H. X., C. K. Snyder, S. F. Pu, and D. N. Ishii. 1996. Insulin-like growth factors reverse or arrest diabetic neuropathy: effects on hyperalgesia and impaired nerve regeneration in rats. Exp. Neurol. 140:198-205.

What is claimed:

1. A method for stimulating angiogenesis in a subject who has a muscle injury, comprising the steps of:
   injecting into muscle tissue of the injured muscle of the subject an isolated nucleic acid expression construct that is substantially free from a viral backbone; and
   electroporating the muscle tissue of the injured muscle after the nucleic acid expression construct has been delivered into the muscle tissue of the injured muscle of the subject; wherein the muscle tissue comprises cells; and
   the isolated nucleic acid expression construct comprises:
   a synthetic myogenic promoter consisting of SEQ ID NO.: 3;
   a nucleic acid sequence encoding an insulin-like growth factor I ("IGF-I"); and
   a 3' untranslated region (3'UTR);
   wherein the synthetic myogenic promoter, the nucleic acid sequence encoding IGF-I, and the 3'UTR are operably linked; whereby cells of the muscle tissue of the injured muscle of the subject take up the isolated nucleic acid expression construct and IGF-I is expressed, and angiogenesis is stimulated in the muscle tissue of the injured muscle of the subject.

2. The method of claim 1, wherein the 3'UTR comprises a nucleic acid sequence that is a skeletal alpha actin gene or a human growth hormone gene, and retains 3'UTR activity.

3. The method of claim 1, further comprising: mixing the isolated nucleic acid expression construct with a transfection-facilitating system before delivering the isolated nucleic acid expression construct into the muscle tissue of the injured muscle of the subject.

4. The method of claim 3, wherein the transfection-facilitating system is a liposome, or a cationic lipid.

5. The method of claim 1, wherein the isolated nucleic acid expression construct comprises a nucleic acid sequence encoding an amino acid sequence of SEQ ID NO.:4 and retains the function of inducing angiogenesis in muscle tissue.

6. The method of claim 1, wherein the isolated nucleic acid expression construct comprises Seq. ID NO. 1.

7. The method of claim 1, further comprising mixing the isolated nucleic acid expression construct with an effective concentration of a transfection polypeptide before delivering the isolated nucleic acid expression construct into muscle tissue of the injured muscle of the subject, wherein the transfection-facilitating polypeptide comprises a charged polypeptide.

8. The method of claim 7, wherein the transfection-facilitating polypeptide comprises poly-L-glutamate.

9. The method of claim 1, wherein the nucleic acid expression construct is delivered into the tissue of the subject via a single administration.

10. The method of claim 1, wherein the cells of the tissue are diploid cells.

11. The method of claim 1, wherein the subject is a human, a pet animal, a farm animal, a food animal, or a work animal.

12. The method of claim 1, wherein the 3'UTR comprises SEQ ID No.: 5 or SEQ ID No.: 6.

* * * * *